US012668636B2

(12) United States Patent
Binaschi et al.

(10) Patent No.: US 12,668,636 B2

(45) Date of Patent: Jun. 30, 2026

(54) PHARMACEUTICAL COMBINATIONS

(71) Applicant: BERLIN-CHEMIE AG, Berlin (DE)

(72) Inventors: Monica Binaschi, Rome (IT); Mario Bigioni, Rome (IT); Giuseppe Merlino, Rome (IT); Cecilia Simonelli, Florence (IT); Francesco Bertoni, Bellinzona (CH); Andrea Pellacani, Florence (IT)

(73) Assignee: BERLIN-CHEMIE AG, Berlin (DE)

( * ) Notice: Subject to any disclaimer, the term of this patent is extended or adjusted under 35 U.S.C. 154(b) by 0 days.

(21) Appl. No.: 19/227,795

(22) Filed: Jun. 4, 2025

(65) Prior Publication Data

US 2025/0297014 A1 Sep. 25, 2025

Related U.S. Application Data

(62) Division of application No. 17/735,880, filed on May 3, 2022, now Pat. No. 12,351,635, which is a division of application No. 16/492,559, filed as application No. PCT/EP2018/055939 on Mar. 9, 2018, now Pat. No. 11,365,258.

(30) Foreign Application Priority Data

Mar. 10, 2017 (GB) ...................................... 1703876

(51) Int. Cl.

| | |
|---|---|
| ***A61P 35/00*** | (2006.01) |
| ***A61K 31/519*** | (2006.01) |
| ***A61K 47/68*** | (2017.01) |
| ***C07K 16/28*** | (2006.01) |

(52) U.S. Cl.

CPC ........ *C07K 16/2851* (2013.01); *A61K 31/519* (2013.01); *A61K 47/68033* (2023.08); *A61K 47/6849* (2017.08); *A61P 35/00* (2018.01); *C07K 16/2887* (2013.01)

(58) Field of Classification Search

CPC ............ C07K 16/2851; C07K 16/2887; A61K 31/519; A61K 47/68033; A61K 47/6849; A61P 35/00

USPC ........................................................ 424/133.1

See application file for complete search history.

(56) References Cited

U.S. PATENT DOCUMENTS

| | | | |
|---|---|---|---|
| 3,691,016 | A | 9/1972 | Patel |
| 3,969,287 | A | 7/1976 | Jaworek et al. |
| 4,179,337 | A | 12/1979 | Davis et al. |
| 4,195,128 | A | 3/1980 | Hildebrand et al. |
| 4,229,537 | A | 10/1980 | Hodgins |
| 4,247,642 | A | 1/1981 | Hirohara et al. |
| 4,256,746 | A | 3/1981 | Miyashita et al. |
| 4,294,757 | A | 10/1981 | Asai |
| 4,301,144 | A | 11/1981 | Iwashita et al. |
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,330,440 | A | 5/1982 | Ayers et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,439,196 | A | 3/1984 | Higuchi |
| 4,447,224 | A | 5/1984 | Decant |
| 4,447,233 | A | 5/1984 | Mayfield |
| 4,450,254 | A | 5/1984 | Isley et al. |
| 4,475,196 | A | 10/1984 | La Zor |
| 4,486,194 | A | 12/1984 | Ferrara |
| 4,487,603 | A | 12/1984 | Harris |
| 4,496,689 | A | 1/1985 | Mitra |
| 4,522,811 | A | 6/1985 | Eppstein et al. |
| 4,596,556 | A | 6/1986 | Morrow et al. |
| 4,640,835 | A | 2/1987 | Shimizu et al. |
| 4,670,417 | A | 6/1987 | Iwasaki et al. |
| 4,790,824 | A | 12/1988 | Morrow et al. |
| 4,791,192 | A | 12/1988 | Nakagawa et al. |
| 4,816,397 | A | 3/1989 | Boss et al. |
| 4,816,567 | A | 3/1989 | Cabilly et al. |
| 4,880,935 | A | 11/1989 | Thorpe |
| 4,941,880 | A | 7/1990 | Burns |
| 5,064,413 | A | 11/1991 | McKinnon et al. |
| 5,122,368 | A | 6/1992 | Greenfield et al. |
| 5,208,020 | A | 5/1993 | Chari et al. |
| 5,312,335 | A | 5/1994 | McKinnon et al. |
| 5,347,548 | A | 9/1994 | Messerges et al. |

(Continued)

FOREIGN PATENT DOCUMENTS

| | | |
|---|---|---|
| CN | 106146663 A | 11/2016 |
| EP | 0 425 235 B1 | 9/1996 |

(Continued)

OTHER PUBLICATIONS

U.S. Appl. No. 12/631,508, filed Dec. 4, 2009, Chari et al.

(Continued)

*Primary Examiner* — Yan Xiao

(74) *Attorney, Agent, or Firm* — Foley & Lardner LLP

(57) ABSTRACT

The present disclosure relates generally to the fields of immunology and molecular biology. More specifically, provided herein are pharmaceutical combinations comprising (A) antibodies, or antigen-binding portions thereof, directed against LY75, and (B) a second anti-cancer entity; nucleic acids encoding antibody combinations; methods for preparing antibody combinations; and methods for the treatment of diseases, such as cancers mediated by LY75 expression or activity.

7 Claims, 31 Drawing Sheets

Specification includes a Sequence Listing.

(56) References Cited

U.S. PATENT DOCUMENTS

| | | | |
|---|---|---|---|
| 5,374,548 | A | 12/1994 | Caras |
| 5,383,851 | A | 1/1995 | McKinnon et al. |
| 5,399,163 | A | 3/1995 | Peterson et al. |
| 5,399,331 | A | 3/1995 | Loughrey et al. |
| 5,416,016 | A | 5/1995 | Low et al. |
| 5,416,064 | A | 5/1995 | Chari et al. |
| 5,530,101 | A | 6/1996 | Queen et al. |
| 5,585,089 | A | 12/1996 | Queen et al. |
| 5,622,929 | A | 4/1997 | Willner et al. |
| 5,693,761 | A | 12/1997 | Queen et al. |
| 5,693,762 | A | 12/1997 | Queen et al. |
| 5,736,137 | A | 4/1998 | Anderson et al. |
| 5,821,337 | A | 10/1998 | Carter et al. |
| 5,824,805 | A | 10/1998 | King et al. |
| 5,859,205 | A | 1/1999 | Adair et al. |
| 6,054,297 | A | 4/2000 | Carter et al. |
| 6,086,875 | A | 7/2000 | Blumberg et al. |
| 6,180,370 | B1 | 1/2001 | Queen et al. |
| 6,214,345 | B1 | 4/2001 | Firestone et al. |
| 6,331,415 | B1 | 12/2001 | Cabilly et al. |
| 6,407,213 | B1 | 6/2002 | Carter et al. |
| 6,441,163 | B1 | 8/2002 | Chari et al. |
| 6,737,056 | B1 | 5/2004 | Presta |
| 7,276,497 | B2 | 10/2007 | Chari et al. |
| 7,303,749 | B1 | 12/2007 | Chari |
| 7,368,565 | B2 | 5/2008 | Chari et al. |
| 7,514,444 | B2 | 4/2009 | Honigberg et al. |
| 7,521,541 | B2 | 4/2009 | Eigenbrot et al. |
| 7,601,354 | B2 | 10/2009 | Chari |
| 7,657,380 | B2 | 2/2010 | Lazar et al. |
| 7,670,600 | B2 | 3/2010 | Dall'Acqua et al. |
| 7,923,221 | B1 | 4/2011 | Cabilly et al. |
| 8,008,309 | B2 | 8/2011 | Honigberg et al. |
| 8,028,778 | B2 | 10/2011 | Luo et al. |
| 8,367,805 | B2 | 2/2013 | Chamberlain et al. |
| 8,476,284 | B2 | 7/2013 | Honigberg et al. |
| 8,497,277 | B2 | 7/2013 | Honigberg et al. |
| 8,697,711 | B2 | 4/2014 | Honigberg et al. |
| 8,703,780 | B2 | 4/2014 | Honigberg et al. |
| 8,735,403 | B2 | 5/2014 | Honigberg et al. |
| 8,754,090 | B2 | 6/2014 | Buggy et al. |
| 8,754,091 | B2 | 6/2014 | Honigberg et al. |
| 8,937,158 | B2 | 1/2015 | Lazar et al. |
| 8,957,079 | B2 | 2/2015 | Honigberg et al. |
| 8,999,999 | B2 | 4/2015 | Buggy et al. |
| 9,125,889 | B2 | 9/2015 | Buggy et al. |
| 9,181,257 | B2 | 11/2015 | Honigberg et al. |
| 9,296,753 | B2 | 3/2016 | Smyth et al. |
| 10,485,794 | B2 | 11/2019 | Seki |
| 2001/0035606 | A1 | 11/2001 | Schoen |
| 2004/0013210 | A1 | 1/2004 | Bollano et al. |
| 2005/0054832 | A1 | 3/2005 | Lazar et al. |
| 2005/0114037 | A1 | 5/2005 | Desjarlais et al. |
| 2005/0238649 | A1 | 10/2005 | Doronina et al. |
| 2006/0012032 | A1 | 1/2006 | Paulus et al. |
| 2006/0024298 | A1 | 2/2006 | Lazar et al. |
| 2006/0024317 | A1 | 2/2006 | Boyd et al. |
| 2006/0074008 | A1 | 4/2006 | Senter et al. |
| 2006/0235208 | A1 | 10/2006 | Lazar et al. |
| 2007/0148170 | A1 | 6/2007 | Desjarlais et al. |
| 2016/0257760 | A1 | 9/2016 | Terrett et al. |

FOREIGN PATENT DOCUMENTS

| | | | |
|---|---|---|---|
| EP | 1 391 213 | A1 | 2/2004 |
| EP | 1 616 572 | A1 | 1/2006 |
| EP | 2 550 975 | A1 | 1/2013 |
| JP | 2009-515861 | A | 4/2009 |
| JP | 2016-529245 | A | 9/2016 |
| WO | WO-92/11018 | | 7/1992 |
| WO | WO-94/11026 | A2 | 5/1994 |
| WO | WO-94/13804 | A1 | 6/1994 |
| WO | WO-00/09160 | A1 | 2/2000 |
| WO | WO-01/24763 | A2 | 4/2001 |
| WO | WO-02/16368 | A1 | 2/2002 |
| WO | WO-02/083180 | A1 | 10/2002 |
| WO | WO-02/098883 | A1 | 12/2002 |
| WO | WO-03/011161 | A1 | 2/2003 |
| WO | WO-2004/010957 | | 2/2004 |
| WO | WO-2004/026293 | A2 | 4/2004 |
| WO | WO-2004/043493 | A1 | 5/2004 |
| WO | WO-2004/103272 | A1 | 12/2004 |
| WO | WO-2005/112919 | A2 | 12/2005 |
| WO | WO-2006/034488 | A2 | 3/2006 |
| WO | WO-2006/110476 | A2 | 10/2006 |
| WO | WO-2007/018431 | A2 | 2/2007 |
| WO | WO-2007/054719 | A2 | 5/2007 |
| WO | WO-2007/059404 | A2 | 5/2007 |
| WO | WO-2007/089149 | A2 | 8/2007 |
| WO | WO-2008/104806 | A2 | 9/2008 |
| WO | WO-2009/017394 | A1 | 2/2009 |
| WO | WO-2009/061996 | A2 | 5/2009 |
| WO | WO-2009/087462 | A2 | 7/2009 |
| WO | WO-2010/062171 | A2 | 6/2010 |
| WO | WO-2013/020690 | A1 | 2/2013 |
| WO | WO-2014/072700 | A1 | 5/2014 |
| WO | WO-2015/017812 | A1 | 2/2015 |
| WO | WO-2015/052537 | A1 | 4/2015 |
| WO | WO-2016/167236 | A1 | 10/2016 |
| WO | WO-2016/172583 | A1 | 10/2016 |
| WO | WO-2016/200676 | A1 | 12/2016 |

OTHER PUBLICATIONS

Al-Tubuly et al., "Differential expression of gp200-MR6 molecule in benign hyperplasia and down-regulation in invasive carcinoma of the breast," Br. J. of Cancer, 1996, 74:1005-1011.

Al-Tubuly et al., "Inhibition of growth and enhancement of differentiation of colorectal carcinoma cell lines by Mab and IL-4," Int. J. Cancer, 1997, 71:605-611.

Badiee et al., "Enhanced delivery of immunoliposomes to human dendritic cells by targeting the multilectin receptor DEC-205," Vaccine, 2007, 25:4757-4766.

Brown et al., "Tolerance to single, but not multiple, amino acid replacements in antibody VH CDR2," Journal of Immmunology, 1996,156:3285-3291.

Camicia, R. et al., Novel drug targets for personalized precision medicine in relapsed/refractory diffuse large B-cell lymphoma: a comprehensive review, Molecular Cancer 14:207, Dec. 1, 2015, 62 pps., DO1: 10.1186/S12943-015-0474-2.

Chari, Ravi V.J., "Targeted cancer therapy: conferring specificity to cytotoxic drugs," Accounts of Chemical Research, Jan. 2008, 41(1):98-107.

Colman, P. M., "Effects of amino acid sequence changes on antibody-antigen interactions", Research in Immunology, 145(1), 1994, pp. 33-36.

Gaman et al., "The unexpected evolution of a case of diffuse large B-cell non-Hodgkin lymphoma" Rom J Morphol Embryol, 52(2), 2011, pp. 719-722.

Gibbs, W. Wayt, "Nanobodies," Scientific American, 2005, 79-83.

Guo et al., "A monoclonal antibody to the DEC-205 endocytosis receptor on human dendritic cells," Human Immunology, 2000, 61:729-738.

Heppner et al., "Tumour heterogeneity: biological implications and therapeutic consequences," Cancer Metastasis Reviews, 1983, 2:5-23.

Holt et al., "Domain antibodies: proteins for therapy," Trends in Biotechnology, Nov. 2003, 21(11):484-490.

International Search Report and Written Opinion regarding Appl. No. PCT/EP2018/055939, mail date Jul. 16, 2018, 25 pps.

Jain, Rakesh K., "Barriers to drug delivery in solid tumours," Sci. Am., Jul. 1994, 271(1):58-65.

Kueppers, Ralf, "Hodgkin lymphoma," Atlas Genet. Cytogenet. Oncol. Haematol., 2011, 15(6):527-528.

Lambert, John M., "Drug-conjugated antibodies for the treatment of cancer," Br. J. Clin. Pharmacol., 2012, 76(2):248-262.

Lambert, John M., "Drug-conjugated monoclonal antibodies for the treatment of cancer," Curr. Opinion. in Pharmacol., 2005, 5:543-549.

(56) References Cited

OTHER PUBLICATIONS

Lectins (FluoProbes) product information from Interchim, 2 pages.
Lollini et al., "Vaccines for tumour prevention," Nature Reviews, Mar. 2006, 6:204-216.
Lymphoma Research Foundation, Chronic Lymphocytic Leukemia/Small Lymphocytic Lymphoma (CLL/SLL), 2012, 3 pages, http://www.lymphoma.org/site/pp.asp?c=bkLTKaOQLmK8E&b=6300147&gclid=CJ2ChMCLL/SLL.
Mahnke et al., "Targeting of antigens to activated dendritic cells in vivo cures metastatic melanoma in mice," Cancer Res, 2005, 65(15):7007-7012.
Mat et al., "Tumour-associated upregulation of the IL-4 receptor complex," Br. J. Cancer, 1990, 62:96-98.
Nchinda et al., "The efficacy of DNA vaccination is enhanced in mice by targeting the encoded protein to dendritic cells," J. Clin. Invest., Apr. 2008, 118(4):1427-1436.
Nonoka et al., "Diagnostic utility of thymic epithelial markers CD205 (DEC205) and Foxn1 in thymic epithelial neoplasms," Am. J. Surg. Pathol., Jul. 2007, 31(7):1038-1044.
Office Action dated Mar. 22, 2022 in JP 2019-548920, English translation.
Paul, J et al., Simultaneous Inhibition of PI3K[delta] and PI3K[alpha] Induces ABC-DLBCL Regression by Blocking BCR-Dependent and -Independent Activation of NF-[kappa]B and Akt, Cancer Cell, Cell Press, US, vol. 31, No. 1, Jan. 9, 2017 (Jan. 9, 2017), pp. 64-78, 16 pps., XP029878806, ISSN: 1535-6108, DOI: 10.1016/J.CCELL.2016.12.003.
Reddy, Kavita S., "Chronic lymphocytic leukaemia (CLL)," Atlas of Genet. Cytogenet. Oncol. Haematol., 2005, 9(3):238-240.
Rituximab—MeSH—NCBI, Sep. 21, 2021, pp. 1-3.
Rudikoff et al., "Single amino acid substitution altering antigen-binding specificity", Proceedings of the National Academy of Sciences, 79(6), 1982, pp. 1979-1983.
Sauter et al., "Phase I Study Combining Ibrutinib with Rituximab, Ifosfamide, Carboplatin, and Etoposide (R-ICE) in Patients with Relapsed or Primary Refractory Diffuse Large B-Cell Lymphoma (DLBCL): NCI-Cancer Therapeutics Evaluation Program (CTEP) #9588," Blood, 2016, 128(22):4198.
Scott et al., "Antibody therapy of cancer," Nature Reviews, Apr. 2012, 12:278-287.
Silverman et al., "Multivalent avimer proteins evolved by exon shuffling of a family of human receptor domains," Nature Biotechnology, Dec. 2005, 23(12):1556-1561.
UK Combined Search and Examination Report regarding Appl. No. GB1703876.1, mail date Dec. 20, 2017, 10 pps.
Vajdos et al., "Comprehensive Functional Maps of the Antigen-binding Site of an Anti-ErbB2 Antibody Obtained with Shotgun Scanning Mutagenesis", J. Mol. Biol., Jul. 5, 2002, 320:415-428.
Young, R. M. et al., B-cell receptor signaling in diffuse large B-cell lymphoma, Nature Medicine, Nature Pub. Co, New York, vol. 52, No. 8, Apr. 1, 2015 (Apr. 1, 2015), pp. 77-85, XP009505877, ISSN: 1078-8956, DOI: 0.1053/J.SEMINHEMATOL.2Q15.01.008.

```
SEQ ID No: 11        EVQLVESGGGLVKPGGSLRLSCAASGFTFSNAWMSWVRQAPGKGLEWVGRIKSKTDGGTT
SEQ ID No: 1         EVQLVESGGGLVKPGGSLRLSCAASGFTYSNAWMSWVRQAPGKGLEWVGRIKSKTDGGTT
SEQ ID No: 12        ------------------------------------------------------------
                     ****************************:*******************************

SEQ ID No: 11        DYAAPVKGRFTISRDDSKNTLYLQMNSLKTEDTAVYYCTTTTVT---------------
SEQ ID No: 1         DYAAPVQGRFTISRDDSKNTLYLQMNSLKTEDTAVYYCTIFGVVSFDYWGQGTLVTVSS
SEQ ID No: 12        --------------------------------------------YFDYWGQGTLVTVSS
                     ******:********************************      **************
```

FIGURE 1

```
SEQ ID No: 2         DVQMTQSPSSLSASVGDRVTITCRASQSISDYLSWYQQRPGKAPNLLIYAASNLKTGVPS
SEQ ID No: 13        DIQMTQSPSSLSASVGDRVTITCRASQSISSYLNWYQQKPGKAPKLLIYAASSLQSGVPS
SEQ ID No: 14        ------------------------------------------------------------
                     *:**************************** ** ****:*****:******* *: ****

SEQ ID No: 2         RFSGSGSGTDFTLTISTLQPEDFATYYCQQSYRSPWTFGQGTKVEIKR
SEQ ID No: 13        RFSGSGSGTDFTLTISSLQPEDFATYYCQQSYS---------------
SEQ ID No: 14        -----------------------------------WTFGQGTKVEIKR
                     ****************:***************   *************
```

FIGURE 2

```
sp|O60449|LY75_HUMAN    MRTGWATPRRPAGLLMLLFWFFDLAEPSGRAANDPFTIVHGNTGKCIKPVYGWIVADDCD 60
MS-Peptides_Elute1a     -------------------------------------------------CIKPVYGWIVADDCD
MS-Peptides_Elute1b     -------------------------------------------------CIKPVYGWIVADDCD
MS-Peptides_Elute2a     ------------------------------------------------------------
MS-Peptides_Elute2b     ------------------------------------------------------------
LC-Peptides             ------------------------------------------------------------

sp|O60449|LY75_HUMAN    ETEDKLWKWVSQHRLFHLHSQKCLGLDITKSVNELRMFSCDSSAMLWWKCEHHSLYGAAR 120
MS-Peptides_Elute1a     ETEDKLWK----------------------------------CEHHSLYGAAR
MS-Peptides_Elute1b     ETEDKLWK-----------------------------------------------
MS-Peptides_Elute2a     -------------------------------------------------------
MS-Peptides_Elute2b     -------------------------------------------------------
LC-Peptides             -------------------------------------------------------

sp|O60449|LY75_HUMAN    YRLALKDGHGTAISNASDVWKKGGSEESLCDQPYHEIYTRDGNSYGRPCEFPFLIDGTWH 180
MS-Peptides_Elute1a     -------DGHGTAISNASDVWKKGGSEESLCDQPYHEIYTR------------------
MS-Peptides_Elute1b     -----------------------KGGSEESLCDQPYHEIYTR----------------
MS-Peptides_Elute2a     ----------------------GGSEESLCDQPYHEIYTR------------------
MS-Peptides_Elute2b     ----------------------GGSEESLCDQPYHEIYTR------------------
LC-Peptides             -------DGHGTAISNASDVWK------------------------------------

sp|O60449|LY75_HUMAN    HDCILDEDHSGPWCATTLNYEYDRKWGICLKPENGCEDNWEKNEQFGSCYQFNTQTALSW 240
MS-Peptides_Elute1a     ----------------------------------------------------------
MS-Peptides_Elute1b     -------------------------WGICLKPENGCEDNWEK----------------
MS-Peptides_Elute2a     ----------------------------------------------------------
MS-Peptides_Elute2b     ----------------------------------------------------------
LC-Peptides             ----------------------------------------------------------

sp|O60449|LY75_HUMAN    KEAYVSCQNQGADLLSINSAAELTYLKEKEGIAKIFWIGLNQLYSARGWEWSDHKPLNFL 300
MS-Peptides_Elute1a     --------------------------------IFWIGLNQLYSAR-------------
MS-Peptides_Elute1b     ----------------------------------------------------------
MS-Peptides_Elute2a     -------------------------------IFWIGLNQLYSAR--------------
MS-Peptides_Elute2b     ----------------------------------------------------------
LC-Peptides             ----------------------------------------------------------

sp|O60449|LY75_HUMAN    NWDPDRPSAPTIGGSSCARMDAESGLWQSFSCEAQLPYVCRKPLNNTVELTDVWTYSDTR 360
MS-Peptides_Elute1a     ----------------------------------------------------------
MS-Peptides_Elute1b     ----------------------------------------------------------
MS-Peptides_Elute2a     ----------------------------------------------------------
MS-Peptides_Elute2b     ----------------------------------------------------------
LC-Peptides             ----------------------------------------------------------

sp|O60449|LY75_HUMAN    CDAGWLPNNGFCYLLVNESNSWDKAHAKCKAFSSDLISIHSLADVEVVVTKLHNEDIKEE 420
MS-Peptides_Elute1a     ------------------------------------------LHNEDIKEE
MS-Peptides_Elute1b     ------------------------------------------LHNEDIKEE
MS-Peptides_Elute2a     -------------------------------------------------
MS-Peptides_Elute2b     -------------------------------------------------
LC-Peptides             -------------------------------------------------

sp|O60449|LY75_HUMAN    VWIGLKNINIPTLFQWSDGTEVTLTYWDENEPNVPYNKTPNCVSYLGELGQWKVQSCEEK 480
MS-Peptides_Elute1a     VWIGLK-------------------TPNCVSYLGELGQWK-------
MS-Peptides_Elute1b     VWIGLK-------------------TPNCVSYLGELGQWK-------
MS-Peptides_Elute2a     ----------------------------------------------
MS-Peptides_Elute2b     ----------------------------------------------
LC-Peptides             ----------------------------------------------
```

FIG 7B

```
sp|O60449|LY75_HUMAN        LKYVCKRKGEKLNDASSDKMCPPDEGWKRHGETCYKIYEDEVPFGTNCNLTITSRFEQEY 540
MS-Peptides_Elute1a         ------------------------------------------------------------
MS-Peptides_Elute1b         ------------------------------------------------------------
MS-Peptides_Elute2a         ------------------------------------------------------------
MS-Peptides_Elute2b         ------------------------------------------------------------
LC-Peptides                 ------------------------------------------------------------


sp|O60449|LY75_HUMAN        LNDLMKKYDKSLRKYFWTGLRDVDSCGEYNWATVGGRRRAVTFSNWNFLEPASPGGCVAM 600
MS-Peptides_Elute1a         --------------YFWTGLRDVDSCGEYNWATVGGR-----------------------
MS-Peptides_Elute1b         --------------YFWTGLRDVDSCGEYNWATVGGR-----------------------
MS-Peptides_Elute2a         --------------YFWTGLRDVDSCGEYNWATVGGR-----------------------
MS-Peptides_Elute2b         --------------YFWTGLRDVDSCGEYNWATVGGR-----------------------
LC-Peptides                 ------------------------------------------------------------


sp|O60449|LY75_HUMAN        STGKSVGKWEVKDCRSFKALSICKKMSGPLGPEEASPKPDDPCPEGWQSFPASLSCYKVF 660
MS-Peptides_Elute1a         ----SVGKWEVKDCR---ALSICKK-----------------------------------
MS-Peptides_Elute1b         ------------------------------------------------------------
MS-Peptides_Elute2a         ------------------------------------------------------------
MS-Peptides_Elute2b         ------------------------------------------------------------
LC-Peptides                 --------WEVKDCRSFK--------------------------------PASLSCYKVF


sp|O60449|LY75_HUMAN        HAERIVRKRNWEEAERFCQALGAHLSSFSHVDEIKEFLHFLTDQFSGQHWLWIGLNKRSP 720
MS-Peptides_Elute1a         --------RNWEEAER-----------------------------------------RSP
MS-Peptides_Elute1b         --------RNWEEAER-----------------------------------------RSP
MS-Peptides_Elute2a         ------------------------------------------------------------
MS-Peptides_Elute2b         ------------------------------------------------------------
LC-Peptides                 HA----------------------------------------------------------


sp|O60449|LY75_HUMAN        DLQGSWQWSDRTPVSTIIMPNEFQQDYDIRDCAAVKVFHRPWRRGWHFYDDREFIYLRPF 780
MS-Peptides_Elute1a         -----------TPVSTIIMPNEFQQDYDIR------------------------------
MS-Peptides_Elute1b         DLQGSWQWSDRTPVSTIIMPNEFQQDYDIR------------------------------
MS-Peptides_Elute2a         --------------------------------------------GWHFYDDR--------
MS-Peptides_Elute2b         ------------------------------------------------------------
LC-Peptides                 ----------------------------------------PWRRGWHFYDDREFIYLRPF


sp|O60449|LY75_HUMAN        ACDTKLEWVCQIPKGRTPKTPDWYNPDRAGIHGPPLIIEGSEYWFVADLHLNYEEAVLYC 840
MS-Peptides_Elute1a         ------------------------------------------------------------
MS-Peptides_Elute1b         ------------------------------------------------------------
MS-Peptides_Elute2a         ------------------------------------------------------------
MS-Peptides_Elute2b         ------------------------------------------------------------
LC-Peptides                 ------------------------------------------------------------


sp|O60449|LY75_HUMAN        ASNHSFLATITSFVGLKAIKNKIANISGDGQKWWIRISEWPIDDHFTYSRYPWHRFPVTF 900
MS-Peptides_Elute1a         ------------------------------------ISEWPIDDHFTYSR-----FPVTF
MS-Peptides_Elute1b         ------------------------------------ISEWPIDDHFTYSR----------
MS-Peptides_Elute2a         ------------------------------------------------------------
MS-Peptides_Elute2b         ------------------------------------------------------------
LC-Peptides                 ------------------------------------------DDHFTYSRYPWHRFPVTF
                                                                      ********

sp|O60449|LY75_HUMAN        GEECLYMSAKTWLIDLGKPTDCSTKLPFICEKYNVSSLEKYSPDSAAKVQCSEQWIPFQN 960
MS-Peptides_Elute1a         GEECLYMSAKTWLIDLGKPTDCSTK-------YNVSSLEK--------VQCSEQWIPFQN
MS-Peptides_Elute1b         ----------TWLIDLGKPTDCSTK-------YNVSSLEK--------VQCSEQWIPFQN
MS-Peptides_Elute2a         ----------TWLIDLGKPTDCSTK-----------------------------------
MS-Peptides_Elute2b         ----------TWLIDLGKPTDCSTK-----------------------------------
LC-Peptides                 G-----------------------------------------------------------


sp|O60449|LY75_HUMAN        KCFLKIKPVSLTFSQASDTCHSYGGTLPSVLSQIEQDFITSLLPDMEATLWIGLRWTAYE 1020
```

FIG. 7C

```
MS-Peptides_Elute1a      ------------------------------------------------------------
MS-Peptides_Elute1b      ------------------------------------------------------------
MS-Peptides_Elute2a      ------------------------------------------------------------
MS-Peptides_Elute2b      ------------------------------------------------------------
LC-Peptides              ------------------------------------------------------------

sp|O60449|LY75_HUMAN     KINKWTDNRELTYSNFHPLLVSGRLRIPENFFEEESRYHCALILNLQKSPFTGTWNFTSC 1080
MS-Peptides_Elute1a      K--------ELTYSNFHPLLVSGRLRIPENFFEEESRYHCALILNLQK------------
MS-Peptides_Elute1b      K------------------------------------YHCALILNLQK------------
MS-Peptides_Elute2a      ------------------------------------------------------------
MS-Peptides_Elute2b      ------------------------------------------------------------
LC-Peptides              --------RELTYSNFHPLL------------------------------------FTSC

sp|O60449|LY75_HUMAN     SERHFVSLCQKYSEVKSRQTLQNASETVKYLNNLYKIIPKTLTWHSAKRECLKSNMQLVS 1140
MS-Peptides_Elute1a      ---HFVSLCQK-------QTLQNASETVK-----------TLTWHSAK------------
MS-Peptides_Elute1b      ---HFVSLCQK-------QTLQNASETVK-----------TLTWHSAK------------
MS-Peptides_Elute2a      ------------------------------------------------------------
MS-Peptides_Elute2b      ------------------------------------------------------------
LC-Peptides              SERHFVSLCQKYS-------------TVKYLNNLYKII----------------------
                            ********               ***

sp|O60449|LY75_HUMAN     ITDPYQQAFLSVQALLHNSSLWIGLFSQDDELNFGWSDGKRLHFSRWAETNGQLEDCVVL 1200
MS-Peptides_Elute1a      ------------------------------------------------------------
MS-Peptides_Elute1b      ------------------------------------------------------------
MS-Peptides_Elute2a      ------------------------------------------------------------
MS-Peptides_Elute2b      ------------------------------------------------------------
LC-Peptides              ------------------------------------------------------------

sp|O60449|LY75_HUMAN     DTDGFWKTVDCNDNQPGAICYYSGNETEKEVKPVDSVKCPSPVLNTPWIPFQNCCYNFII 1260
MS-Peptides_Elute1a      ------------------------------------------------------------
MS-Peptides_Elute1b      ------------------------------------------------------------
MS-Peptides_Elute2a      ------------------------------------------------------------
MS-Peptides_Elute2b      ------------------------------------------------------------
LC-Peptides              ------------------------------------------------------------

sp|O60449|LY75_HUMAN     TKNRHMATTQDEVHTKCQKLNPKSHILSIRDEKENNFVLEQLLYFNYMASWVMLGITYRN 1320
MS-Peptides_Elute1a      -----------------------SHILSIR------------------------------
MS-Peptides_Elute1b      --NRHMATTQDEVHTK-------SHILSIR------------------------------
MS-Peptides_Elute2a      ------------------------------------------------------------
MS-Peptides_Elute2b      ------------------------------------------------------------
LC-Peptides              ------------------------------------------------------------

sp|O60449|LY75_HUMAN     KSLMWFDKTPLSYTHWRAGRPTIKNEKFLAGLSTDGFWDIQTFKVIEEAVYFHQHSILAC 1380
MS-Peptides_Elute1a      -SLMWFDKTPLSYTHWR-------------------------------------------
MS-Peptides_Elute1b      -SLMWFDK----------------------------------------------------
MS-Peptides_Elute2a      -SLMWFDK----------------------------------------------------
MS-Peptides_Elute2b      ------------------------------------------------------------
LC-Peptides              ---------------------------------------------EAVYFHQHSIL--

sp|O60449|LY75_HUMAN     KIEMVDYKEEYNTTLPQFMPYEDGIYSVIQKKVTWYEALNMCSQSGGHLASVHNQNGQLF 1440
MS-Peptides_Elute1a      ------------------------------------------------------------
MS-Peptides_Elute1b      ------------------------------------------------------------
MS-Peptides_Elute2a      ------------------------------------------------------------
MS-Peptides_Elute2b      ------------------------------------------------------------
LC-Peptides

sp|O60449|LY75_HUMAN
MS-Peptides_Elute1a      ------------------------------------------------------------
MS-Peptides_Elute1b
MS-Peptides_Elute2a
```

FIG. 7D

```
MS-Peptides_Elute2b       ------------------------------------------------------------
LC-Peptides               ------------------------------------------------------------

sp|O60449|LY75_HUMAN      KCNSVKDGAICYKPTKSKKLSRLTYSSRCPAAKENGSRWIQYKGHCYKSDQALHSFSEAK 1560
MS-Peptides_Elute1a       ------------------------------------------------------------
MS-Peptides_Elute1b       ------------------------------------------------------------
MS-Peptides_Elute2a       ------------------------------------------------------------
MS-Peptides_Elute2b       ------------------------------------------------------------
LC-Peptides               -----------------KKLSRLTYSS-C-----NGSRWIQYKGHCYKSDQALH------

sp|O60449|LY75_HUMAN      KLCSKHDHSATIVSIKDEDENKFVSRLMRENNNITMRVWLGLSQHSVDQSWSWLDGSEVT 1620
MS-Peptides_Elute1a       -----HDHSATIVSIKDEDENKFVSR----------------------------------
MS-Peptides_Elute1b       -----HDHSATIVSIKDEDENKFVSR----------------------------------
MS-Peptides_Elute2a       -----HDHSATIVSIKDEDENKFVSR----------------------------------
MS-Peptides_Elute2b       ------------------------------------------------------------
LC-Peptides               ------------------------------------------------------------

sp|O60449|LY75_HUMAN      FVKWENKSKSGVGRCSMLIASNETWKKVECEHGFGRVVCKVPLGPDYTAIAIIVATLSIL 1680
MS-Peptides_Elute1a       ---------------------------VECEHGFGR------------------------
MS-Peptides_Elute1b       ---------------------------VECEHGFGR------------------------
MS-Peptides_Elute2a       ------------------------------------------------------------
MS-Peptides_Elute2b       ------------------------------------------------------------
LC-Peptides               ------------------------------------------------------------

sp|O60449|LY75_HUMAN      VLMGGLIWFLFQRHRLHLAGFSSVRYAQGVNEDEIMLPSFHD 1722
MS-Peptides_Elute1a       ------------------------------------------
MS-Peptides_Elute1b       ------------------------------------------
MS-Peptides_Elute2a       ------------------------------------------
MS-Peptides_Elute2b       ------------------------------------------
LC-Peptides               ------------------------------------------
```

PHARMACEUTICAL COMBINATIONS

CROSS REFERENCE TO RELATED APPLICATIONS

This application is a Divisional of U.S. application Ser. No. 17/735,880, filed May 3, 2022, which is a Divisional of U.S. application Ser. No. 16/492,559, which is the U.S. National Stage of International Application No. PCT/EP2018/055939, filed Mar. 9, 2018, and claims the benefit of U.K. Application No. 1703876.1, filed Mar. 10, 2017, the contents of which are incorporated herein by reference in their entirety.

SEQUENCE LISTING

The instant application contains a Sequence Listing which has been submitted in XML format and is hereby incorporated by reference in its entirety. Said XML copy, created on Mar. 31, 2025, is named 111346-0338_SL.xml and is 245,743 bytes.

INTRODUCTION

The present disclosure relates generally to the fields of immunology and molecular biology. More specifically, provided herein are pharmaceutical combinations comprising (A) antibodies, or antigen-binding portions thereof, directed against LY75, and (B) a second anti-cancer entity; nucleic acids encoding antibody combinations; methods for preparing antibody combinations; and methods for the treatment of diseases, such as cancers mediated by LY75 expression or activity.

BACKGROUND

Leukemias and lymphomas belong to a broad group of tumours that affect the blood, bone marrow, and lymphoid system; these are known as tumors of the hematopoietic and lymphoid tissues.

Lymphoma is a group of blood cell tumours that develop from lymphocytes. Signs and symptoms may include enlarged lymph nodes, fever, drenching sweats, unintended weight loss, itching and constantly feeling tired. There are a number of subtypes of lymphomas: the two main categories of lymphomas are Hodgkin's lymphomas (HL) and the non-Hodgkin lymphomas (NHL). The World Health Organization (WHO) includes two other categories as types of lymphoma: multiple myeloma and immunoproliferative diseases. About 90% of lymphomas are non-Hodgkin lymphomas.

Leukemia is a group of cancers that usually begin in the bone marrow and result in high numbers of abnormal white blood cells. Symptoms may include bleeding and bruising problems, feeling tired, fever and an increased risk of infections. These symptoms occur due to a lack of normal blood cells. Diagnosis is typically made by blood tests or bone marrow biopsy. There are four main types of leukemia: acute lymphoblastic leukemia (ALL), acute myeloid leukemia (AML), chronic lymphocytic leukemia (CLL) and chronic myeloid leukemia (CML), as well as a number of less common types.

Treatment of leukemias and lymphomas may involve one or more of chemotherapy, radiation therapy, targeted therapy and surgery (and bone marrow transplant in the case of leukemias). The success of leukemia treatment depends on the type of leukemia and the age of the person. The lymphoma treatment outcome depends on the subtype with some being curable and treatment prolonging survival in most.

A number of chemotherapeutic agents have previously been used for the treatment of leukemias including prednisone, vincristine, anthracyclines, L-asparaginase, cyclophosphamide, methotrexate, 6-mercaptopurine, fludarabine, pentostatin and cladribine. Chemotherapeutic agents for the treatment of lymphomas include cyclophosphamide, hydroxydaunorubicin (also known as doxorubicin or adriamycin), oncovin (vincristine), prednisone, prednisolone, bleomycin, dacarbazine, etoposide and procarbazine.

Combination chemotherapy involves treating a patient with a two or more different drugs simultaneously. The drugs may differ in their mechanism and side-effects. The biggest advantage of this is minimising the chances of resistance developing to any one agent. Furthermore, the drugs can often be used at lower doses, reducing toxicity. Combination therapies for the treatment of Hodgkin's Disease include MOPP (mustine, vincristine, procarbazine, prednisolone) and ABVD (Doxorubicin, bleomycin, vinblastine, dacarbazine). Combination therapies for the treatment of Non-Hodgkin's lymphoma include CHOP (cyclophosphamide, doxorubicin, vincristine, prednisolone). Given the number of drugs that are known for the treatment of leukemias and lymphomas, the number of permutations and combinations of possible drug therapies is clearly large. Furthermore, the aforementioned combination therapies do not include antibodies.

There remains, however, a need for new treatments of leukemias and lymphomas, and particularly for efficacious combination therapies.

Lymphocyte antigen 75 acts as an endocytic receptor to direct captured antigens from the extracellular space to a specialized antigen-processing compartment and is thought to cause a reduction in proliferation of B-lymphocytes. Expression of Lymphocyte antigen 75 has been observed in pancreatic, ovarian, breast, colorectal, esophageal, skin, thyroid and lung (non-small-cell) cancers as well as Multiple Myeloma and many different subtypes of lymphomas and leukaemias. WO2009/061996 discloses isolated monoclonal antibodies which bind to human DEC-205 (LY75) and related antibody based compositions and molecules. Also disclosed are pharmaceutical compositions comprising the antibodies, as well as therapeutic and diagnostic methods for using the antibodies. WO2008/104806 discloses affinity reagents capable of binding to LY75 for use in the treatment or prophylaxis of cancer. WO2015/052537 discloses specific isolated antibodies capable of binding to LY75 and their use in the treatment various cancers.

Rituximab is a monoclonal antibody against the protein CD20 which is widely expressed on B cells (Oncogene (2003 Oct. 20), Smith MR, "Rituximab (monoclonal anti-CD20 antibody): mechanisms of action and resistance", 22(47): 7359-68). Rituximab destroys both normal and malignant B cells that have CD20 on their surfaces and is therefore used to treat diseases which are characterized by having too many B cells, overactive B cells, or dysfunctional B cells. Riuximab has previously been used to treat a number of autoimmune diseases and some types of cancer, including rheumatoid arthritis, idiopathic thrombocytopenia purpura, pemphigus vulgaris, multiple sclerosis, systemic lupus erythematosus, non-Hodgkin's lymphoma, chronic inflammatory demyelinating polyneuropathy, chronic lymphocytic leukemia and autoimmune anemias.

Ibrutinib (Imbruvica) is a small molecule drug that binds permanently to Bruton's tyrosine kinase (BTK), which is important in B cells. Ibrutinib has previously been used to treat B cell cancers like mantle cell lymphoma, chronic lymphocytic leukemia, and Waldenström's macroglobulinemia.

It has now been found that combinations of (i) certain anti-LY75 antibodies with Rituximab and (ii) certain anti-LY75 antibodies with Ibrutinib demonstrate synergistic results in the treatment of lymphomas.

BRIEF SUMMARY OF THE INVENTION

In one aspect, the invention provides a pharmaceutical combination comprising:

(A) an anti-LY75 antibody, or an antigen-binding portion thereof, which competes for binding to LY75 with an antibody comprising a heavy chain variable region comprising the amino acid sequence set forth in SEQ ID NO: 1, and a light chain variable region comprising the amino acid sequence set forth in SEQ ID NO: 2; or an anti-LY75 antibody, or an antigen-binding portion thereof, said antibody comprising:

a) a heavy chain variable region comprising:
i) a first vhCDR comprising SEQ ID NO: 5;
ii) a second vhCDR comprising SEQ ID NO: 6; and
iii) a third vhCDR comprising SEQ ID NO: 7; and b) a light chain variable region comprising:
i) a first vlCDR comprising SEQ ID NO: 8;
ii) a second vlCDR comprising SEQ ID NO: 9; and
iii) a third vlCDR comprising SEQ ID NO: 10;

optionally wherein any one or more of the above SEQ ID NOs independently comprise one, two, three, four or five amino acid substitutions, additions or deletions; and (B) an anti-CD20 antibody, or an antigen-binding portion thereof, said antibody comprising:

a) a heavy chain variable region comprising:
i) a first vhCDR comprising SEQ ID NO: 40;
ii) a second vhCDR comprising SEQ ID NO: 41; and
iii) a third vhCDR comprising SEQ ID NO: 42; and b) a light chain variable region comprising:
i) a first vlCDR comprising SEQ ID NO: 43;
ii) a second vlCDR comprising SEQ ID NO: 44; and
iii) a third vlCDR comprising SEQ ID NO: 45;

optionally wherein any one or more of the above SEQ ID NOs independently comprise one, two, three, four or five amino acid substitutions, additions or deletions;

wherein the pharmaceutical combination is in the form of a combined preparation for simultaneous, separate or sequential use.

In a second aspect, the invention provides a pharmaceutical combination comprising:

(A) an anti-LY75 antibody, or an antigen-binding portion thereof, which competes for binding to LY75 with an antibody comprising a heavy chain variable region comprising the amino acid sequence set forth in SEQ ID NO: 1, and a light chain variable region comprising the amino acid sequence set forth in SEQ ID NO: 2;

or an anti-LY75 antibody, or an antigen-binding portion thereof, said antibody comprising:

a) a heavy chain variable region comprising:
i) a first vhCDR comprising SEQ ID NO: 5;
ii) a second vhCDR comprising SEQ ID NO: 6; and
iii) a third vhCDR comprising SEQ ID NO: 7; and b) a light chain variable region comprising:
i) a first vlCDR comprising SEQ ID NO: 8;
ii) a second vlCDR comprising SEQ ID NO: 9; and
iii) a third vlCDR comprising SEQ ID NO: 10;

optionally wherein any one or more of the above SEQ ID NOs independently comprise one, two, three, four or five amino acid substitutions, additions or deletions;

and (B) ibrutinib or a pharmaceutically-acceptable salt thereof, wherein the pharmaceutical combination is in the form of a combined preparation for simultaneous, separate or sequential use.

In one embodiment, the anti-LY75 antibody or antigen-binding portion thereof comprises a heavy chain variable region comprising 1, 2 or 3 CDRs selected from the group consisting of CDRs comprising SEQ ID NOs: 5, 6, and 7, and/or a light chain variable region comprising 1, 2 or 3 CDRs selected from the group consisting of CDRs comprising SEQ ID NOs: 8, 9 and 10.

In some embodiments, the anti-LY75 antibodies bind to LY75 (SEQ ID NO: 15) and are capable of being internalized by a cell expressing LY75.

In another embodiment, the anti-LY75 antibody comprises the heavy and/or light chain complementarity determining regions (CDRs) or variable regions (VRs) of the particular antibody described herein (e.g., referred to herein as "LY75_A1"). Accordingly, in one embodiment, the anti-LY75 antibody comprises the CDR1, CDR2, and CDR3 domains of the heavy chain variable (VH) region of antibody LY75_A1 having the sequence shown in SEQ ID NO:1, and/or the CDR1, CDR2 and CDR3 domains of the light chain variable (VL) region of LY75_A1 having the sequence shown in SEQ ID NO:2.

In another embodiment, the anti-LY75 antibodies bind to human LY75 and include a heavy chain variable region comprising SEQ ID NO: 1, and/or conservative sequence modifications thereof. The antibody may further include a light chain variable region comprising SEQ ID NO:2, and/or conservative sequence modifications thereof.

In a further embodiment, the anti-LY75 antibodies bind to human LY75 and include a heavy chain variable region and a light chain variable region including the amino acid sequences set forth in SEQ ID NOs: 1 and/or 2, respectively, and conservative sequence modifications thereof.

Antibodies which include heavy and light chain variable regions having at least 80%, or at least 85%, or at least 90%, or at least 91%, or at least 92%, or at least 93%, or at least 94%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention.

In one embodiment, the anti-LY75 antibody comprises a heavy chain variable region comprising SEQ ID NO:1 or a sequence that is at least 80%, at least 85%, at least 90%, at least 91%, at least 92%, at least 93%, at least 94%, at least 95%, at least 96%, at least 97%, at least 98%, at least 99% identical to SEQ ID NO: 1. In another embodiment, the anti-LY75 antibody comprises a light chain variable region comprising SEQ ID NO:2 or a sequence that is at least 80%, at least 85%, at least 90%, at least 91%, at least 92%, at least 93%, at least 94%, at least 95%, at least 96%, at least 97%, at least 98%, at least 99% identical to SEQ ID NO: 2. In another embodiment, the anti-LY75 antibody comprises a heavy chain framework region comprising an amino acid sequence that is at least 80%, at least 85%, at least 90%, at least 91%, at least 92%, at least 93%, at least 94%, at least 95%, at least 96%, at least 97%, at least 98%, at least 99% identical to the framework of the heavy chain variable region of SEQ ID NO: 1 as shown in SEQ ID NOS: 16, 17, 18 and 19. In another embodiment, the anti-LY75 antibody comprises a light chain framework region comprising an amino acid sequence that is at least 80%, at least 85%, at least 90%, at least 91%, at least 92%, at least 93%, at least 94%, at least 95%, at least 96%, at least 97%, at least 98%, at least 99% identical to the framework of the light chain variable region of SEQ ID NO:2 as shown in SEQ ID NOS: 20, 21, 22 and 23.

In one embodiment, the anti-LY75 antibody competes for binding to LY75 with an antibody comprising heavy and/or light chain variable regions comprising the amino acid sequences set forth in SEQ ID NOs: 1 and 2, respectively, or amino acid sequences at least 80%, at least 85%, at least 90%, at least 91%, at least 92%, at least 93%, at least 94%, at least 95%, at least 96%, at least 97%, at least 98%, at least 99% identical thereto. In another embodiment, the anti-LY75 antibody competes for binding to LY75 with an antibody comprising heavy and/or light chain variable regions comprising the amino acid sequences set forth in SEQ ID NOs: 1 and 2 (LY75_A1).

Other antibodies of the invention bind to the same epitope or an epitope on LY75 recognized by the antibodies described herein. In another particular embodiment, the antibody binds to an epitope on LY75 recognized by an antibody comprising heavy and/or light chain variable regions comprising the amino acid sequences set forth in SEQ ID NOs: 1 and 2, respectively, or amino acid sequences at least 80% identical thereto. In another embodiment, the antibody binds to an epitope on LY75 recognized by an antibody comprising heavy and/or light chain variable regions comprising the amino acid sequences set forth in SEQ ID NOs: 1 and 2 (LY75_A1).

In a further embodiment, the anti-LY75 antibodies bind specifically to one or more, for example, 2, 3, 4, 5, 6, 7, 8, 9 or 10, peptide(s) selected from the group comprising SEQ ID NOs: 24, 25, 26, 27, 28, 29, 30, 31, 32, 33, 34, 35, 36 or 37 or fragments thereof, wherein said fragments comprises at least 2, at least 3, at least 4, at least 5, at least 6, at least 7, at least 8, at least 9 or at least 10 contiguous amino acids. In a further embodiment, the epitope recognized by the anti-LY75 antibodies comprises one or more peptides, two or more or three or more peptides selected from the group consisting of SEQ ID NOs: 27, 29, 30, 34, 35, 36 or 37 or fragments thereof wherein said fragments comprises at least 2, at least 3, at least 4, at least 5, at least 6, at least 7, at least 8, at least 9 or at least 10 contiguous amino acids. In a further embodiment, the epitope recognized by the anti-LY75 antibodies comprises one or more peptides, for example, two or three peptides selected from the group consisting of SEQ ID NOS: 30, 36 and 37 or fragments thereof wherein said fragments comprises at least 2, at least 3, at least 4, at least 5, at least 6, at least 7, at least 8, at least 9 or at least 10 contiguous amino acids.

In a further embodiment, the anti-LY75 antibodies comprise variable CDRs as compared to the parent antibodies described herein. Thus, the variant antibodies comprising variant variable regions of a parent antibody, wherein the parent antibody comprises a first vhCDR comprising SEQ ID NO:5, a second vhCDR comprising SEQ ID NO: 6, a third vhCDR comprising SEQ ID NO: 7, a first vlCDR comprising SEQ ID NO:8, a second vlCDR comprising SEQ ID NO:9 and a third vlCDR comprising a SEQ ID NO:10, and wherein the variant antibody has 1, 2, 3, 4, 5 or 6 amino acid substitutions collectively in the set of the first vhCDR, the second vhCDR, the third vhCDR, the first vlCDR, the second vlCDR and the third vlCDR, with from 1 to 4, 1 to 3 or 1 to 2 substitutions of particular use, and wherein the antibody retains specific binding to LY75.

All of the antibodies disclosed herein can be full-length, for example, any of the following isotypes: IgG1, IgG2, IgG3, IgG4, IgM, IgA1, IgA2, IgAsec, IgD, and IgE. Alternatively, the antibodies can be fragments such as an antigen-binding portion or a single chain antibody (e.g., a Fab, $F(ab')_2$, Fv, a single chain Fv fragment, an isolated complementarity determining region (CDR) or a combination of two or more isolated CDRs). The antibodies can be any kind of antibody, including, but not limited to, human, humanized, and chimeric antibodies.

In other embodiments, the anti-LY75 antibodies are in the form of an immunoconjugate (i.e., further include a covalently-attached moiety). In a particular embodiment, the moiety is a drug, such as a maytansinoid, a dolastatin, an auristatin, a trichothecene, a calicheamicin, CC1065 or derivatives thereof. In a preferred embodiment, the drug moiety is DM1 or DM4.

In one embodiment, the anti-LY75 antibody comprises a heavy chain variable region and a light chain variable region encoded by nucleic acid sequences comprising SEQ ID NOs: 3 and 4, respectively, or nucleic acid sequences having at least 85%, 86%, 87%, 88%, 89%, 90%, 91%, 92%, 93%, 94%, 95%, 96%, 97%, 98% or 99% identity to the aforementioned nucleic acid sequences or sequences which differ from SEQ ID NOs: 3 and 4 due to degeneracy of the genetic code.

In one embodiment, anti-CD20 antibody is a mouse/human chimeric antibody, a humanised antibody or a human antibody. Preferably the anti-CD20 antibody is Rituximab.

In another aspect of the present invention there are provided kits expression vectors comprising nucleic acids encoding heavy and light chain variable regions of the antibodies described herein operably linked to one or more regulatory elements.

In a preferred embodiment the host cell comprises expression vectors comprising nucleic acids encoding:

(i) the heavy chain of the anti-LY75 antibody or antigen-binding portion thereof;
(ii) the light chain of the anti-LY75 antibody or antigen-binding portion thereof;
(iii) the heavy chain of the anti-CD20 antibody or antigen-binding portion thereof; and
(iv) the light chain of the anti-CD20 antibody or antigen-binding portion thereof.

In a further aspect there is provided a method of treating cancer in a patient comprising simultaneously, sequentially or separately administering to a patient in need thereof therapeutically-effective amounts of components (A) and (B) of a pharmaceutical combination of the invention.

In a further aspect of the present invention, there is provided a pharmaceutical combination of the invention for use in the treatment of cancer.

Also provided is the use of components (A) and (B) as defined herein in the manufacture of a pharmaceutical combination for simultaneous, separate or sequential use for the treatment of cancer. In one embodiment the cancer is preferably leukemia or lymphoma.

In some embodiments, the cancer is selected from the group consisting of non-Hodgkin's lymphoma, diffuse large B-cell lymphoma (DLBCL), B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and AngioImmunoblastic T-Cell Lymphoma, acute myeloid leukaemia, and chronic lymphocytic leukaemia. More preferably, the cancer is DLBCL or non-Hodgkin's lymphoma.

Also within the scope of the invention are kits comprising a pharmaceutical combination of the invention and, optionally, instructions for use. The kit can further contain a least one additional reagent or one or more additional antibodies.

Other features and advantages of the instant invention will be apparent from the following detailed description and claims.

BRIEF DESCRIPTION OF THE DRAWINGS

FIG. 1 depicts the alignment of LY75_A1 heavy chain (SEQ ID NO:1), the human VH 3-15 Germline (SEQ ID NO:11) and the human JH4 Germline (SEQ ID NO:12). The CDR regions of LY75_A1 heavy chain are underlined.

FIG. 2 depicts the alignment of LY75_A1 light chain (SEQ ID NO:2), the human VK O12 Germline (SEQ ID NO:13) and the human JK4 Germline (SEQ ID NO:14). The CDR regions of LY75_A1 light chain are underlined.

FIGS. 7A-7D show an amino acid alignment of peptides bound by antibody LY75_A1 in both the peptide microarray assay and the peptide pull down assay. Peptides highlighted are those likely to form the epitope recognized by antibody LY75_A1. Figures disclose SEQ ID NOS 15, 165, 165-169, 169-172, 172-173, 173-174, 174-175, 175, 175, 175-176, 178, 24-25, 180, 180-182, 46, 26, 47, 187, 47, 27, 189-190, 188-190, 188, 188, 192-193, 28-29, 50-51, 137, 50-51, 137, 30, 200, 199, 200-202, 202-206, 206, 206-207, and 207, respectively, in order of appearance.

FIG. 8A: median CI=0.27. FIG. 8B: median CI=0.57.

DETAILED DESCRIPTION OF THE INVENTION

Figure 3A:
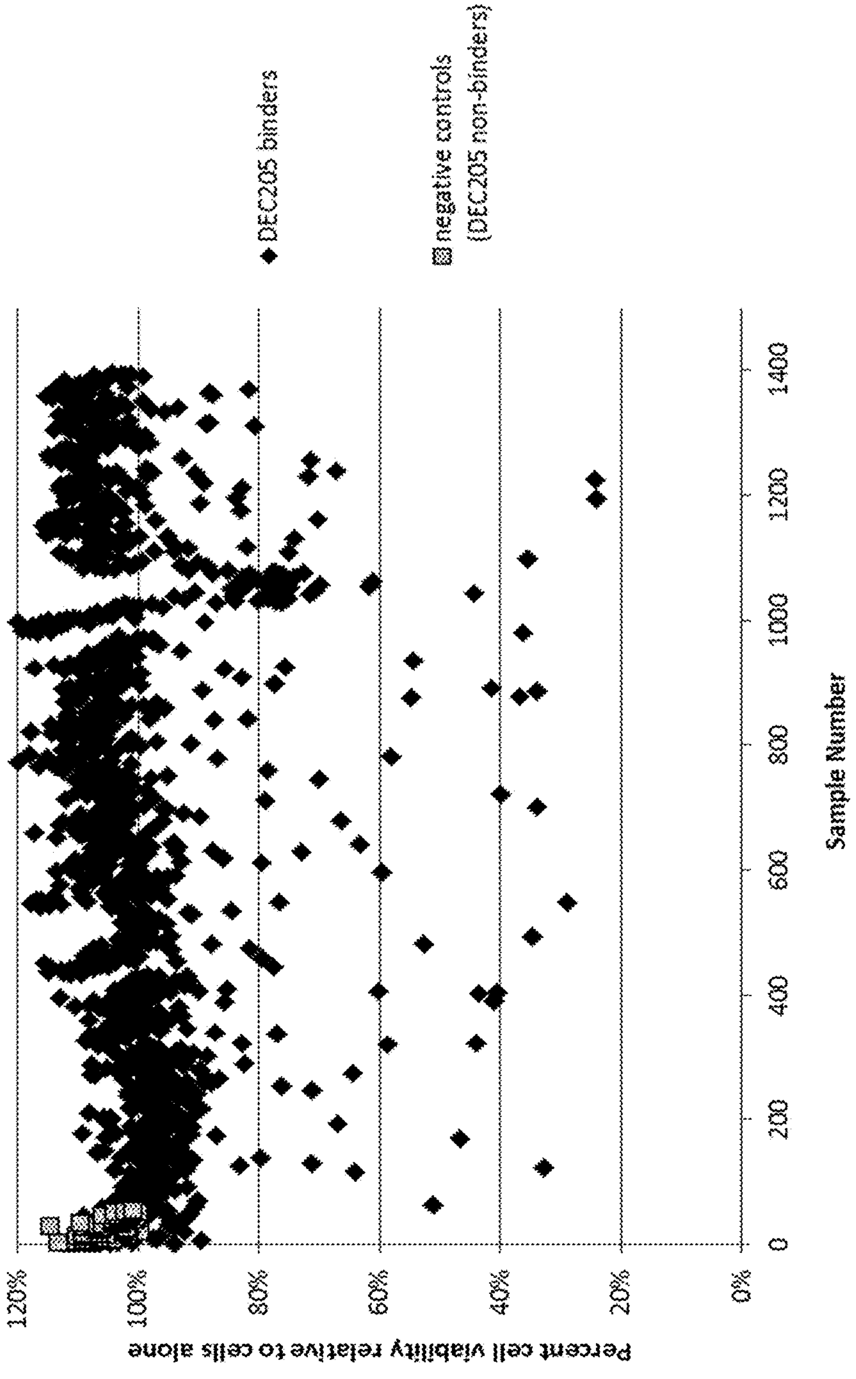
FIG. 3*a* depicts cytotoxic activity of anti-LY75 monoclonal antibodies conjugated with DM1 in HT-29 and shows while most antibodies bind to LY75 only a few display efficacy.

The present disclosure relates to pharmaceutical combinations comprising components (A) and (B) as defined herein, wherein the pharmaceutical combination is in the form of a combined preparation for simultaneous, separate or sequential use. Component (A) relates to an anti-LY75 antibody as defined herein. Component (B) relates either to (i) an anti-CD20 antibody as defined herein or (ii) to ibrutinib or a pharmaceutically-acceptable salt thereof.

One example of the LY75 protein is given in SEQ ID NO: 15 herein. The terms "anti-LY75 antibodies" and "LY75 antibodies" are used interchangeably herein.

The LY75 antibodies disclosed herein may be internalized when contacted with cells expressing the LY75 receptor. As discussed herein, the LY75 receptor is overexpressed and/or differentially expressed on certain cancer cells, including but not limited to, leukaemia preferably acute myeloid leukaemia or chronic lymphocytic leukaemia, lymphoma, preferably DLBCL B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and AngioImmunoblastic T-Cell Lymphoma.

As such, when the LY75 antibodies disclosed herein are conjugated to drugs (sometimes referred to herein as "antibody-drug conjugates" or "ADCs"), the internalization of these ADC molecules into cancer cells results in cell death and thus tumor treatment.

The anti-LY75 antibodies possess particular structural features such as CDR regions with particular amino acid sequences. Described herein are a set of CDRs which can form an affinity reagent, e.g. an antibody, which exhibits binding to LY75.

Thus, the disclosure provides antibodies, preferably isolated antibodies (which, as outlined below, includes a wide variety of well-known antibody structures, derivatives, mimetics and conjugates), nucleic acids encoding antibody combinations, host cells used to make the antibody combinations, methods of making the antibody combinations, and pharmaceutical combinations comprising the antibodies and optionally a pharmaceutical carrier, methods of treatment comprising the use of the pharmaceutical combinations and the use of the pharmaceutical combinations for the treatment of cancers.

Lymphocyte antigen 75 acts as an endocytic receptor to direct captured antigens from the extracellular space to a specialized antigen-processing compartment and is thought to cause a reduction in proliferation of B-lymphocytes.

According to SWISS-PROT, Lymphocyte antigen 75 is expressed in spleen, thymus, colon and peripheral blood lymphocytes. It has been detected in myeloid and B lymphoid cell lines. Isoforms designated herein OGTA076b and OGTA076c are expressed in malignant Hodgkin's lymphoma cells called Hodgkin's and Reed-Sternberg (HRS) cells. LY75 acts as an endocytic receptor to direct captured antigens from the extracellular space to a specialized antigen-processing compartment. It causes reduced proliferation of B-lymphocytes.

Expression of LY75 has been observed in pancreatic, bladder, ovarian, breast (including triple negative), colorectal, esophageal, skin, thyroid and lung (non-small-cell) cancers as well as Multiple Myeloma and many different subtypes of lymphomas (including DLBCL) and leukaemias.

The anti-LY75 antibody may, in certain cases, cross-react with the LY75 from species other than human. For example, to facilitate clinical testing, the anti-LY75 antibodies may cross react with murine or primate LY75 molecules. Alternatively, in certain embodiments, the antibodies may be completely specific for human LY75 and may not exhibit species or other types of non-human cross-reactivity.

The present invention relates to anti-LY75 antibodies and, in some embodiments anti-CD20 antibodies, generally therapeutic antibodies as described herein. Antibodies that find use in the present invention can take on a number of formats as described herein, including traditional antibodies as well as antibody derivatives, fragments and mimetics, described below. In one embodiment, the invention provides antibody structures that contain a set of 6 CDRs as defined herein (including small numbers of amino acid changes as described below).

"Antibody" as used herein includes a wide variety of structures, as will be appreciated by those in the art, that in some embodiments contain at a minimum a set of 6 CDRs as defined herein; including, but not limited to traditional antibodies (including both monoclonal and polyclonal antibodies), humanized and/or chimeric antibodies, antibody fragments, engineered antibodies (e.g. with amino acid modifications as outlined below), multispecific antibodies (including bispecific antibodies), and other analogs known in the art.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. It should be understood that therapeutic antibodies can also comprise hybrids of any combination of isotypes and/or subclasses.

In many embodiments, IgG isotypes are used in the present invention, with IgG1 finding particular use in a number of applications.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. As described herein, methods for determining what epitopes are bound by a given antibody (i.e., epitope mapping) are well known in the art and include, for example, immunoblotting and immunoprecipitation assays, wherein overlapping or contiguous peptides from LY75 are tested for reactivity with the given anti-LY75 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)). The term "epitope mapping" refers to the process of identification of the molecular determinants for antibody-antigen recognition.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al.).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Structures that rely on the use of a set of CDRs are included within the definition of "antibody".

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable region, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

In some embodiments, the antibody can be a mixture from different species, e.g. a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

The antibodies disclosed herein may be isolated or recombinant. "Isolated," when used to describe the various polypeptides disclosed herein, means a polypeptide that has been identified and separated and/or recovered from a cell or cell culture from which it was expressed. Thus an isolated antibody is intended to refer to an antibody that is substantially free of other antibodies having different antigenic specificities (e.g. an isolated antibody that specifically binds to the LY75 is substantially free of antibodies that specifically bind antigens other than the LY75). Thus, an "isolated" antibody is one found in a form not normally found in nature (e.g. non-naturally occurring). An isolated antibody as defined herein may, in one embodiment, include at least one amino acid which does not occur in the "naturally" occurring antibody. This amino acid may be introduced by way of an addition or a substitution. It will be understood that the introduced amino acid may be a naturally occurring or non-naturally occurring amino acid. In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced. Ordinarily, an isolated polypeptide will be prepared by at least one purification step. An "isolated antibody," refers to an antibody which is substantially free of other antibodies having different antigenic specificities. For instance, an isolated antibody that specifically binds to LY75 is substantially free of antibodies that specifically bind antigens other than LY75, with the exception of antibodies which bind to CD20.

Isolated monoclonal antibodies, having different specificities, can be combined in a well-defined composition. Thus for example, the antibody of the invention can optionally and individually be included or excluded in a formulation, as is further discussed below.

The anti-LY75 antibodies of the present invention specifically bind LY75 (e.g. SEQ ID NO: 15). The anti-CD20 antibodies of the present invention specifically bind CD20. "Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a $K_D$ for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where $K_D$ refers to a dissociation rate of a particular antibody-antigen interaction. Typically, an antibody that specifically binds an antigen will have a $K_D$ that is 20-, 50-, 100-, 500-, 1000-, 5,000-, 10,000-or more times greater for a control molecule relative to the antigen or epitope. However, in the present invention, when administering ADCs of the LY75 antibodies of the invention, what is important is that the $K_D$ is sufficient to allow internalization and thus cell death without significant side effects.

Also, specific binding for a particular antigen or an epitope can be exhibited, for example, by an antibody having a $K_A$ or $K_a$ for an antigen or epitope of at least 20-, 50-, 100-, 500-, 1000-, 5,000-, 10,000-or more times greater for the epitope relative to a control, where $K_A$ or $K_a$ refers to an association rate of a particular antibody-antigen interaction.

Standard assays to evaluate the binding ability of the antibodies toward LY75 or CD20 can be done on the protein or cellular level and are known in the art, including for example, ELISAs, Western blots, RIAs, BIAcore® assays and flow cytometry analysis. Suitable assays are described in detail in the Examples. The binding kinetics (e.g. binding affinity) of the antibodies also can be assessed by standard assays known in the art, such as by Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

The LY75 antibodies that bind to LY75 (SEQ ID NO: 15) maybe internalized when contacted with cells expressing LY75 on the cell surface. These antibodies are referred to herein either as "anti-LY75" antibodies or, for ease of description, "LY75 antibodies". Both terms are used interchangeably herein.

The LY75 antibodies are internalized upon contact with cells, particularly tumor cells, which express LY75 on the surface. That is, LY75 antibodies as defined herein that also comprise drug conjugates are internalized by tumor cells, resulting in the release of the drug and subsequent cell death, allowing for treatment of cancers that exhibit LY75 expression. Internalization in this context can be measured in several ways. In one embodiment, the LY75 antibodies are contacted with cells, such as a cell line as outlined herein, using standard assays such as MAbZap. It would be clear to the skilled person that the MabZap assay is representative of the effect that would be expected to be seen with an antibody-drug conjugate (ADC). In the latter case, the ADC would be internalized, thus taking the drug into the cell. A toxic drug would have the capacity to kill the cell, i.e. to kill the targeted cancer cell. Data from MabZap assays are readily accepted by persons of skill in the art to be representative of ADC assays (Kohls, M and Lappi, D., [2000] Biotechniques, vol. 28, no. 1, 162-165).

In these in vitro assay embodiments, the LY75 antibodies are added, along with an anti-LY75 antibody comprising a toxin; for example, the LY75 antibody may be murine or humanized and the anti-LY75 antibody can be anti-murine or anti-humanized and contain a toxin such as saporin. Upon formation of the [LY75 antibody]-[anti-LY75 antibody-drug conjugate] complex, the complex is internalized and the drug (e.g. saporin) is released, resulting in cell death. Only upon internalization does the drug get released, and thus cells remain viable in the absence of internalization. As outlined below, without being bound by theory, in therapeutic applications, the anti-LY75 antibody contains the toxin, and upon internalization, the bond between the antibody and the toxin is cleaved, releasing the toxin and killing the cell.

In one embodiment, the anti-LY75 antibody comprises the heavy and light chain complementarity determining regions (CDRs) or variable regions (VRs) of the particular antibody described herein (e.g., referred to herein as "LY75_A1"). Accordingly, in one embodiment, the antibody comprises the CDR1, CDR2, and CDR3 domains of the heavy chain variable (VH) region of antibody LY75_A1 having the sequence shown in SEQ ID NO:1, and the CDR1, CDR2 and CDR3 domains of the light chain variable (VL) region of antibody LY75_A1 having the sequence shown in SEQ ID NO:2.

In another embodiment, the anti-LY75 antibody comprises a heavy chain variable region comprising a first vhCDR comprising SEQ ID NO: 5; a second vhCDR comprising SEQ ID NO: 6; and a third vhCDR comprising SEQ ID NO:7; and a light chain variable region comprising a first vlCDR comprising SEQ ID NO:8; a second vlCDR comprising SEQ ID NO: 9; and a third vlCDR comprising SEQ ID NO:10.

In another embodiment, the anti-LY75 antibodies bind to human LY75 and include a heavy chain variable region comprising an amino acid sequence comprising SEQ ID NO:1, and conservative sequence modifications thereof. The antibody may further include a light chain variable region comprising an amino acid sequence comprising SEQ ID NO:2, and conservative sequence modifications thereof.

In a further embodiment, the anti-LY75 antibodies bind to human LY75 and include a heavy chain variable region and a light chain variable region comprising the amino acid sequences set forth in SEQ ID NOs: 1 and/or 2, respectively, and conservative sequence modifications thereof. As used herein, the term conservative sequence modification refers to, for example, the substitution of an amino acid with an amino acid having similar characteristics. It is common general knowledge for one skilled in the art what such substitutions may be considered conservative. Other modifications which can be considered to be conservative sequence modifications include, for example, glycosylation.

Optionally, one or more of SEQ ID NOs: 5-10 independently comprise one, two, three, four or five conservative amino acid substitutions; optionally, one or more SEQ ID NOs: 5-10 independently comprise one or two conservative amino acid substitutions.

Preferably, the term "conservative sequence modifications" is intended to include amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

Isolated antibodies which include heavy and light chain variable regions having at least 80%, or at least 85%, or at least 90%, or at least 91%, or at least 92%, or at least 93%, or at least 94%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention. In one embodiment, the anti-LY75 antibody comprises a heavy chain variable region comprising SEQ ID NO:1 or a sequence that is at least 90%, at least 91%, at least 92%, at least 93%, at least 94%, at least 95%, at least 96%, at least 97%, at least 98%, at least 99% identical to SEQ ID NO: 1. In another embodiment, the anti-LY75 antibody comprises a light chain variable region comprising SEQ ID NO:2 or a sequence that is at least 90%, at least 91%, at least 92%, at least 93%, at least 94%, at least 95%, at least 96%, at least 97%, at least 98%, at least 99% identical to SEQ ID NO: 2. In another embodiment, the anti-LY75 antibody comprises a heavy chain framework region comprising an amino acid sequence that is at least 90%, at least 91%, at least 92%, at least 93%, at least 94%, at least 95%, at least 96%, at least 97%, at least 98%, at least 99% identical to the framework of the heavy chain variable region of SEQ ID NO: 1 comprising SEQ ID NOs: 16, 17 and 18. In another embodiment, the anti-LY75 antibody comprises a light chain framework region comprising an amino acid sequence that is at least 90%, at least 91%, at least 92%, at least 93%, at least 94%, at least 95%, at least 96%, at least 97%, at least 98%, at least 99% identical to the framework of the light chain variable region of SEQ ID NO:2 comprising SEQ ID NOs: 19, 20 and 21.

In one embodiment, the anti-LY75 antibody is referred to herein as "LY75_A1 antibody" comprising the following CDRs, as well as variants containing a limited number of amino acid variants:

| A1 | SEQ ID NOs |
|---|---|
| variable heavy CDR1 | 5 |
| variable heavy CDR2 | 6 |
| variable heavy CDR3 | 7 |
| variable light CDR1 | 8 |
| variable light CDR2 | 9 |
| variable light CDR3 | 10 |

Disclosed herein are also variable heavy and light chains that comprise the CDR sets of the invention, as well as full length heavy and light chains (e.g. comprising constant regions as well). As will be appreciated by those in the art, the CDR sets of the anti-LY75 antibody can be incorporated into murine, humanized or human constant regions (including framework regions). Accordingly, the present disclosure provides variable heavy and light chains that are at least about 90%-99% identical to the SEQ IDs disclosed herein, with 90, 91, 92, 93, 94, 95, 96, 97, 98 and 99% all finding use in the present invention.

In some embodiments, the anti-LY75 antibody is one which competes for binding to human LY75 with an antibody comprising a heavy chain variable region comprising the amino acid sequence set forth in SEQ ID NO: 1, and a light chain variable region comprising the amino acid sequence set forth in SEQ ID NO: 2. Antibodies that compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as LY75. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% 75-80% 80-85% 85-90% 90-95% 95-99% or more.

Monoclonal antibodies can be characterized for binding to LY75 or CD20 using a variety of known techniques. Generally, the antibodies are initially characterized by ELISA. Briefly, microtiter plates can be coated with purified LY75 or CD20 in PBS, and then blocked with irrelevant proteins such as bovine serum albumin (BSA) diluted in PBS. Dilutions of plasma from LY75-immunized mice or CD20-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the LY75/CD20 immunogen. Hybridomas that bind, preferably with high affinity, to LY75/CD20 can then be sub-cloned and further characterized. One clone from each hybridoma, which retains the reactivity of the parent cells (by ELISA), can then be chosen for making a cell bank, and for antibody purification.

To purify anti-LY75 or anti-CD20 antibodies, selected hybridomas can be grown in roller bottles, two-liter spinner-flasks or other culture systems. Supernatants can be filtered and concentrated before affinity chromatography with protein A-Sepharose (Pharmacia, Piscataway, NJ) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected anti-LY75 or anti-CD20 monoclonal antibodies bind to unique epitopes, each antibody can be biotinylated using commercially available reagents (Pierce, Rockford, IL). Biotinylated MAb binding can be detected with a streptavidin labeled probe. To determine the isotype of purified antibodies, isotype ELISAs can be performed using art recognized techniques. For example, wells of microtiter plates can be coated with 10 μg/ml of anti-Ig overnight at 4° C. After blocking with 5% BSA, the plates are reacted with 10 μg/ml of monoclonal antibodies or purified isotype controls, at ambient temperature for two hours. The wells can then be reacted with either IgGI or other isotype specific conjugated probes. Plates are developed and analyzed as described above.

To test the binding of monoclonal antibodies to live cells expressing LY75 or CD20, flow cytometry can be used. Briefly, cell lines and/or human PBMCs expressing membrane-bound LY75 or CD20 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-LY75 IgGs can be further tested for reactivity with the LY75 antigen by Western blotting; the same may be done with anti-CD20 antibodies. Briefly, cell extracts from cells expressing LY75/CD20 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, MO).

Methods for analyzing binding affinity, cross-reactivity, and binding kinetics of various anti-LY75 antibodies include standard assays known in the art, for example, Biacore™ surface plasmon resonance (SPR) analysis using a Biacore™ 2000 SPR instrument (Biacore AB, Uppsala, Sweden.

In one embodiment, the antibody specifically binds to human LY75 comprising SEQ ID NO: 15) Preferably, the anti-LY75 antibody binds to human LY75 with high affinity.

Preferably, the anti-LY75 antibody binds to a LY75 protein with a $K_D$ of $5\times10^{-8}$ M or less, binds to a LY75 protein with a $K_D$ of $2\times10^{-8}$ M or less, binds to a LY75 protein with a $K_D$ of $5\times10^{-9}$ M or less, binds to a LY75 protein with a $K_D$ of $4\times10^{-9}$ M or less, binds to a LY75 protein with a $K_D$ of $3\times10^{-9}$ M or less, binds to a LY75 protein with a $K_D$ of $2\times10^{-9}$ M or less, binds to a LY75 protein with a $K_D$ of $1\times10^{-9}$ M or less, binds to a LY75 protein with a $K_D$ of $5\times10^{-10}$ M or less, or binds to a LY75 protein with a $K_D$ of $1\times10^{-10}$ M or less.

In one embodiment, anti-LY75 antibodies compete (e.g., cross-compete) for binding to LY75 with the particular anti-LY75 antibodies described herein (e.g.,LY75_A1). Such competing antibodies can be identified based on their ability to competitively inhibit binding to LY75 of one or more of mAbs in standard LY75 binding assays. For example, standard ELISA assays can be used in which a recombinant human LY75 protein is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of an anti-LY75 antibody of the invention to human LY75 demonstrates that the test antibody can compete with the antibody for binding to human LY75.

In one embodiment, the competing antibody is an antibody that binds to the same epitope on human LY75 as the particular anti-LY75 monoclonal antibodies described herein (e.g., LY75_A1). Standard epitope mapping techniques, such as x-ray crystallography and 2-dimensional nuclear magnetic resonance, can be used to determine whether an antibody binds to the same epitope as a reference antibody (see, e.g., Epitope Mapping Protocols in Methods in Molecular Biology, Vol. 66, G. E. Morris, Ed. (1996)).

In one embodiment, the antibody that competes for binding to LY75 and/or binds to the same epitope on human LY75 is a human antibody.

Once a single, archetypal anti-LY75 mAb has been isolated that has the desired properties described herein, other mAbs with similar properties, e.g., having the same epitope may be generated. For example, mice may be immunized with LY75 as described herein, hybridomas produced, and the resulting mAbs screened for the ability to compete with the archetypal mAb for binding to LY75. Mice can also be immunized with a smaller fragment of LY75 containing the epitope to which the archetypal mAb binds. The epitope can be localized by, e.g., screening for binding to a series of overlapping peptides spanning LY75. Alternatively, the method of Jespers et al., Biotechnology 12:899, 1994 may be used to guide the selection of mAbs having the same epitope and therefore similar properties to the archetypal mAb. Using phage display, first the heavy chain of the archetypal antibody is paired with a repertoire of (preferably human) light chains to select a LY75-binding mAb, and then the new light chain is paired with a repertoire of (preferably human) heavy chains to select a (preferably human) LY75-binding mAb having the same epitope as the archetypal mAb. Alternatively variants of the archetypal mAb can be obtained by mutagenesis of cDNA encoding the heavy and light chains of the antibody.

To assess the level of competition between two antibodies, for example, radio-immunoassays or assays using other labels for the antibodies, can be used. For example, a LY75 antigen can be incubated with a saturating amount of a first anti-LY75 antibody or antigen-binding fragment thereof conjugated to a labeled compound (e.g., $^3H$, $^{125}I$, biotin, or rubidium) in the presence the same amount of a second unlabeled anti-LY75 antibody. The amount of labeled antibody that is bound to the antigen in the presence of the unlabeled blocking antibody is then assessed and compared to binding in the absence of the unlabeled blocking antibody. Competition is determined by the percentage change in binding signals in the presence of the unlabeled blocking antibody compared to the absence of the blocking antibody. Thus, if there is a 50% inhibition of binding of the labeled antibody in the presence of the blocking antibody compared to binding in the absence of the blocking antibody, then there is competition between the two antibodies of 50%. Thus, reference to competition between a first and second antibody of 50% or more, 60% or more, 70% or more, such as 70%, 71%, 72%, 73%, 74%, 75%, 80%, 85%, 90%, 95%, 96%, 97%, 98%, 99% or more, means that the first antibody inhibits binding of the second antibody (or vice versa) to the antigen by 50%, 60%, 70%, 71%, 72%, 73%, 74%, 75%, 80%, 85%, 90%, 95%, 96%, 97%, 98%, 99% or more (compared to binding of the antigen by the second antibody in the absence of the first antibody). Thus, inhibition of binding of a first antibody to an antigen by a second antibody of 50%, 605, 70%, 71%, 72%, 73%, 74%, 75%, 80%, 85%, 90%, 95%, 96%, 97%, 98%, 99% or more indicates that the two antibodies bind to the same epitope.

In some embodiments, component (B) of the pharmaceutical combination is an anti-CD20 antibody as defined herein.

B-lymphocyte antigen CD20 or CD20 is an activated-glycosylated phosphoprotein expressed on the surface of all B-cells beginning at the pro-B phase (CD45R+, CD117+) and progressively increasing in concentration until maturity (Hardy, Richard (2008). "Chapter 7: B Lymphocyte Development and Biology". In Paul, William. Fundamental Immunology (Book) (6th ed.). Philadelphia: Lippincott Williams & Wilkins. pp. 237-269. ISBN 0-7817-6519-6.)

CD20 is expressed on all stages of B-cell development except the first and last; it is present from late pro-B cells through memory cells, but not on either early pro-B cells or plasma blasts and plasma cells. It is found on B-cell lymphomas, hairy cell leukemia, B-cell chronic lymphocytic leukemia, and melanoma cancer stem cells. The expression of CD20 is regulated by the chemokine signalling through the CXCR4/SDF1 axis.

Immunohistochemistry can be used to determine the presence of CD20 on cells in histological tissue sections.

In humans, CD20 is encoded by the MS4A1 gene. This gene encodes a member of the membrane-spanning 4A gene family.

In one embodiment, component (B) of the pharmaceutical combination comprises an anti-CD20 antibody, or an antigen-binding portion thereof, said antibody comprising:

a) a heavy chain variable region comprising:
   i) a first vhCDR comprising SEQ ID NO: 40;
   ii) a second vhCDR comprising SEQ ID NO: 41; and
   iii) a third vhCDR comprising SEQ ID NO: 42; and
b) a light chain variable region comprising:
   i) a first vICDR comprising SEQ ID NO: 43;
   ii) a second vICDR comprising SEQ ID NO: 44; and
   iii) a third vICDR comprising SEQ ID NO: 45;

optionally wherein any one or more of the above SEQ ID NOs independently comprise one, two, three, four or five amino acid substitutions, additions or deletions.

Optionally, one or more of the above SEQ ID NOs: 40-45 independently comprise one, two, three, four or five conservative amino acid substitutions; more preferably, any one or more of the above SEQ ID NOs independently comprise one or two conservative amino acid substitutions.

Preferably, the anti-CD-20 antibody is a monoclonal antibody, more preferably a human, monoclonal antibody, and even more preferably a fully human IgG1 monoclonal antibody. In a particularly preferred embodiment of the invention, the anti-CD20 antibody is Rituximab. Rituximab is a monoclonal antibody against the protein CD20 which is widely expressed on B cells (Oncogene (2003 Oct. 20), Smith MR, "Rituximab (monoclonal anti-CD20 antibody): mechanisms of action and resistance", 22(47): 7359-68). Rituximab destroys both normal and malignant B cells that have CD20 on their surfaces and is therefore used to treat diseases which are characterized by having too many B cells, overactive B cells, or dysfunctional B cells. Riuximab has previously been used to treat a number of autoimmune diseases and some types of cancer, including rheumatoid arthritis, idiopathic thrombocytopenia purpura, pemphigus vulgaris, multiple sclerosis, systemic lupus erythematosus, non-Hodgkin's lymphoma, chronic inflammatory demyelinating polyneuropathy, chronic lymphocytic leukemia and autoimmune anemias. Rituximab is sold under the tradename Rituxan® by Roche.

Preferably, the heavy and/or light chain of the rituximab antibody comprises or consists of the amino acid sequence given in SEQ ID NO: 38 and 39, respectively.

The present invention encompasses variant antibodies, sometimes referred to as "antibody derivatives" or "antibody analogs" as well. That is, there are a number of modifications that can be made to the antibodies disclosed herein, including, but not limited to, amino acid modifications in the CDRs (affinity maturation), amino acid modifications in the framework regions, amino acid modifications in the Fc region, glycosylation variants, covalent modifications of other types (e.g. for attachment of drug conjugates, etc.).

By "variant" herein is meant a polypeptide sequence that differs from that of a parent polypeptide by virtue of at least one amino acid modification. In this case, the parent polypeptide is either the full length variable heavy or light chains, e.g. as listed in SEQ ID NOs: 1 or 2, respectively or the CDR regions or the framework regions of the heavy and light chains listed in SEQ ID NOs 5-10 and 16-21 for LY75. Amino acid modifications can include substitutions, insertions and deletions, with the former being preferred in many cases. It will be understood that an amino acid substitution may be a conservative or non-conservative substitution with conservative substitutions being preferred. Further said substitution may be a substitution with either a naturally or non-naturally occurring amino acid.

In general, variants can include any number of modifications, as long as the function of the antibody is still present, as described herein. That is, LY75_A1, for example, the antibody should still specifically bind to human LY75. Similarly, anti-CD20 antibodies should still specifically bind to human CD20. If amino acid variants are generated with the Fc region, for example, the variant antibodies should maintain the required receptor binding functions for the particular application or indication of the antibody.

"Variants" in this case can be made in either the listed CDR sequences, the framework or Fc regions of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications (e.g. individual amino acid substitutions, insertions or deletions), with from 1-2, 1-3 and 1-4 also finding use in many embodiments. The number of modifications can depend on the size of the region being modified; for example, in general, fewer modifications are desired in CDR regions. It will be understood by the skilled person that even within the CDR regions the location of the modification can significantly alter the effect. In one embodiment, the modifications can be made in any of CDR1, CDR2 or CDR3 of the heavy and/or light chains. In a further embodiment, the modifications are made in any of CDR1 or CDR2 of the heavy and/or light chains. In a still further embodiment, the modifications are located in CDR1 of the heavy and/or light chains.

It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 91%, 92%, 93%, 94%, 95%, 96%, 97%, 98% or 99% identity to the parent sequences (e.g. the variable regions, the constant regions, and/or the heavy and light chain sequences and/or the CDRs of LY75_A1 or Rituximab). It should be noted that depending on the size of the sequence, the percent identity will depend on the number of amino acids.

By "amino acid substitution" or "substitution" herein is meant the replacement of an amino acid at a particular position in a parent polypeptide sequence with another amino acid which may be a natural or non-naturally occurring amino acid. For example, the substitution S100A refers to a variant polypeptide in which the serine at position 100 is replaced with alanine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, the parent polypeptides herein are LY75_A1 and Rituximab. Accordingly, by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, one or more amino acid modifications are made in one or more of the CDRs of LY75_A1 or Rituximab. In general, only 1 or 2 or 3 amino acids are substituted in any single CDR, and generally no more than from 4, 5, 6, 7, 8 9 or 10 changes are made within a set of 6 CDRs. However, it should be appreciated that any combination of no substitutions, 1, 2 or 3 substitutions in any CDR can be independently and optionally combined with any other substitution. It will be apparent that substitutions can be made in any of the 6 CDRs. In one embodiment, substitutions are made in CDR1 of the heavy and/or light chains.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10%, about 20%, about 30%, about 40%, about 50%, about 60%, about 70%, about 80%, about 90%, about 100%, about 110%, about 120%, about 130%, about 140%, about 150% or more, or 1, 2, 3, 4 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155:1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies disclosed herein are variant CDRs and antibodies; that is, the antibodies can include amino acid modifications in one or more of the CDRs of LY75_A1 or Rituximab. In addition, as outlined below, amino acid modifications can also independently and optionally be made in any region outside the CDRs, including framework and constant regions as described herein.

In some embodiments, the anti-LY75 antibodies and/or anti-CD20 antibodies disclosed herein are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in U.S. patent application Ser. No. 11/841,654 and references cited therein, US 2004/013210, US 2005/0054832, US 2006/0024298, US 2006/0121032, US 2006/0235208, US 2007/0148170, U.S. Ser. No. 12/341,769, U.S. Pat. Nos. 6,737,056, 7,670,600, 6,086,875 all of which are expressly incorporated by reference in their entirety, and in particular for specific amino acid substitutions that increase binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference).

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Another type of covalent modification is alterations in glycosylation. In some embodiments, the antibodies disclosed herein can be fully or partially aglycosylated, e.g. afucosylated.

Another type of covalent modification of the antibody comprises linking the antibody to various non-proteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

In additional embodiments, the antibodies may comprise a label. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include, but are not limited to, fluorescent lanthanide complexes (including those of Europium and Terbium), and fluorescent labels including, but not limited to, quantum dots, fluorescein, rhodamine, tetramethylrhodamine, eosin, erythrosin, coumarin, methyl-coumarins, pyrene, Malacite green, stilbene, Lucifer Yellow, Cascade Blue, Texas Red, the Alexa dyes, the Cy dyes, and others described in the 6th Edition of the Molecular Probes Handbook by Richard P. Haugland, hereby expressly incorporated by reference.

Antibody-Drug Conjugates

In some embodiments, the anti-LY75 antibodies disclosed herein are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety.

Thus the invention provides pharmaceutical combinations comprising, inter alia, anti-LY75 antibodies conjugated to drugs. Generally, conjugation is done by covalent attachment to the antibody, as further described below, and generally relies on a linker, often a peptide linkage (which, as described below, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug: antibody. As will be appreciated by those in the art, the actual number is an average.

Thus the anti-LY75 antibodies may be conjugated to drugs. As described below, the drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, taxol, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, hemiasterlins, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342), hemiasterlins (WO2004/026293; Zask et al., (2004) J. Med. Chem, 47: 4774-4786). Toxins may exert their cytotoxic and cytostatic effects by mechanisms including tubulin binding, DNA binding, or topoisomerase inhibition.

Conjugates of an anti-LY75 antibody and one or more small molecule toxins, such as a maytansinoids, dolastatins, auristatins, a trichothecene, calicheamicin, duocarmycins, pyrrolobenzadiazepines and CC1065, and the derivatives of these toxins that have toxin activity, may also be used.

Preferably, the anti-LY75 antibody is conjugated to DM1 or DM4, most preferably to DM4. Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using Streptomyces or Actinomyces or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions.

Exemplary maytansinoid drug moieties also include those having modifications such as: C-9-SH (U.S. Pat. No. 4,424, 219) (prepared by the reaction of maytansinol with H2S or P2S5); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared from Nocardia); C-15-hydroxy/acyloxy (U.S. Pat. No. 4,364,866) (prepared by the conversion of maytansinol by Streptomyces); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by Streptomyces); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. No. 5,416,064, WO/01/24763, U.S. Pat. Nos. 7,303,749, 7,601,354, U.S. Ser. No. 12/631,508, WO02/098883, U.S. Pat. Nos. 6,441,163, 7,368,565, WO02/16368 and WO04/1033272, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined.

In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is 2, 3, 4, 5, 6, 7, or 8 or a fraction thereof.

The generation of Antibody-drug conjugate compounds can be accomplished by any technique known to the skilled artisan. Briefly, the Antibody-drug conjugate compounds can include an anti-LY75 antibody as the Antibody unit, a drug, and optionally a linker that joins the drug and the binding agent.

A number of different reactions are available for covalent attachment of drugs and/or linkers to binding agents. This is can be accomplished by reaction of the amino acid residues of the binding agent, for example, antibody molecule, including the amine groups of lysine, the free carboxylic acid groups of glutamic and aspartic acid, the sulfhydryl groups of cysteine and the various moieties of the aromatic amino acids. A commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule.

Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In some embodiments, an intermediate, which is the precursor of the linker, is reacted with the drug under appropriate conditions. In other embodiments, reactive groups are used on the drug and/or the intermediate. The product of the reaction between the drug and the intermediate, or the derivatized drug, is subsequently reacted with an anti-LY75 antibody of the invention under appropriate conditions.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug.

Typically, the antibody-drug conjugate compounds comprise a Linker unit between the drug unit and the antibody unit. In some embodiments, the linker is cleavable under intracellular or extracellular conditions, such that cleavage of the linker releases the drug unit from the antibody in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in LY75-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: 52)). Other examples of such linkers are described, e.g., in U.S. Pat. No. 6,214,345, incorporated herein by reference in its entirety and for all purposes.

In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935).

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See for example, WO 2007/059404A2, WO06/110476A2, WO05/112919A2, WO2010/062171, WO09/017394, WO07/089149, WO 07/018431, WO04/043493 and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the anti-LY75 antibodies of the invention.

A variety of exemplary linkers that can be used with the present compositions and methods are described in WO 2004/010957, U.S. Publication No. 2006/0074008, U.S. Publication No. 20050238649, and U.S. Publication No. 2006/0024317 (each of which is incorporated by reference herein in its entirety and for all purposes). Preferably, the linker is SPDB (N-succinimidyl-3-(2-pyridyldithio)butyrate).

Drug loading is represented by p and is the average number of Drug moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, drug loading of from 1 to 4 is frequently useful, and from 1 to 2 is also useful. ADCs of the invention include collections of antibodies conjugated with a range of drug moieties, from 1 to 20, for example, 1-15, 1-10, 2-9, 3-8, 4-7, 5-6. The average number of drug moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005/0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 μCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

In vivo, the effect of a therapeutic composition of the anti-LY75 antibody of the invention can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3:402-408). Efficacy can be measured using assays that measure inhibition of tumor formation, tumor regression or metastasis, and the like.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Methods for Producing Antibodies

The antibodies disclosed herein may be made by any suitable method. These methods include culturing a host cell containing isolated nucleic acid(s) encoding the antibodies. As will be appreciated by those in the art, this can be done in a variety of ways, depending on the nature of the antibody. In the case where the antibodies are full length traditional antibodies, for example, a heavy chain variable region and a light chain variable region under conditions such that an antibody is produced and can be isolated.

The variable heavy and light chains of LY75_A1 are disclosed herein (both protein and nucleic acid sequences); as will be appreciated in the art, these can be easily augmented to produce full length heavy and light chains. That is, having provided the DNA fragments encoding $V_H$ and $V_K$ segments as outlined herein, these DNA fragments can be further manipulated by standard recombinant DNA techniques, for example, to convert the variable region genes to full-length antibody chain genes, to Fab fragment genes, or to a scFv gene. In these manipulations, a $V_K$-or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of murine heavy chain constant region genes are known in the art [see e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the VL/VK region can be converted to a full-length light chain gene (as well as a Fab light chain gene) by operatively linking the $V_L$-encoding DNA to another DNA molecule encoding the light chain constant region, $C_L$. The sequences of murine light chain constant region genes are known in the art [see, e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. In preferred embodiments, the light chain constant region can be a kappa or lambda constant region.

To create a scFv gene, the $V_H$-and $V_L/V_K$-encoding DNA fragments are operatively linked to another fragment encoding a flexible linker, e.g. encoding the amino acid sequence $(Gly_4\text{-}Ser)_3$ (SEQ ID NO: 208), such that the $V_H$ and $V_L/V_K$ sequences can be expressed as a contiguous single-chain protein, with the $V_L/V_K$ and $V_H$ regions joined by the flexible linker [see e.g. Bird et al. (1988) *Science* 242:423-426; Huston et al. (1988) *Proc. Natl. Acad. Sci. USA* 85:5879-5883; McCafferty et al., (1990) *Nature* 348:552-554].

Nucleic acids are provided which encode the antibodies disclosed herein. Such polynucleotides encode for both the variable and constant regions of each of the heavy and light chains, although other combinations are also contemplated in accordance with the compositions described herein.

The polynucleotides can be in the form of RNA or DNA. Polynucleotides in the form of DNA, cDNA, genomic DNA, nucleic acid analogs, and synthetic DNA are also usable. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies dislcosed herein are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, VA including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are well known, for example, see U.S. Pat. Nos. 4,816,567, 4,816,397, 6,331,415 and 7,923,221, as well as Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

In a further embodiment of the invention, component (B) of the pharmaceutical combination is ibrutinib or a pharmaceutically-acceptable salt thereof. Ibrutinib (Imbruvica®) is a small molecule drug that binds permanently to Bruton's tyrosine kinase (BTK). It has previously been used to treat B-cell cancers such as mantle cell lymphoma, chronic lymphocytic leukemia and Waldenström's macroglobulinemia (a form of non-Hodgkin's lymphoma). The structural and chemical formulae of ibrutinib are given below:

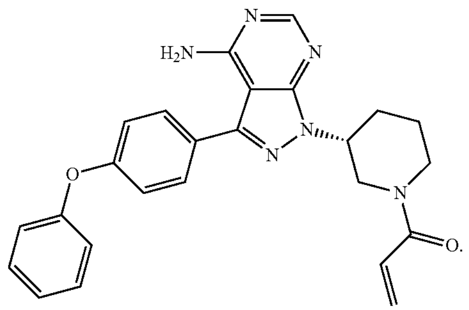

(R)-1-(3-(4-amino-3-(4-phenoxyphenyl)-1H-pyrazolo[3,4-d]pyrimidin-1-yl)piperidin-1-yl)prop-2-en-1-one Ibrutinib is sold under the tradename Imbruvica®. It is available from Pharmacyclics, Inc. (US).

Pharmaceutical Compositions

The pharmaceutical combination of the invention is in the form of a combined preparation for simultaneous, separate or sequential use. Similarly, in the methods of the invention, components (A) and (B) of the pharmaceutical combination may be administered to a patient simultaneously, separately or sequentially.

The term "combined preparation" includes both fixed combinations and non-fixed combinations.

The term "fixed combination" means that the active ingredients (e.g. components (A) and (B)) are in the form of a single entity or dosage. In other words, the active ingredients are present in a single composition or formulation.

The term "non-fixed combination" means that the active ingredients (e.g. components (A) and (B)) are present in different entities or dosages (e.g. as separate compositions or formulations), for example as a kit of parts. The independent components (A) and (B) (in their desired compositions or formulations) can then be administered separately or sequentially, at the same time point or at different time points.

Where the administration is sequential, the delay in administering the second component should not be such as to lose the benefit of the effect arising from use of the combination. Therefore, in one embodiment sequential treatment involves administration of each component of the combination within a period of 11 days. In another embodiment this period is 10 days. In another embodiment this period is 9 days. In another embodiment this period is 8 days. In another embodiment this period is 7 days. In another embodiment this period is within 6 days. In another embodiment this period is within 5 days. In another embodiment this period is within 4 days. In another embodiment this period is within 3 days. In another embodiment this period is within 2 days. In another embodiment this period is within 24 hours. In another embodiment this period is within 12 hours.

Components (A) and (B) may be administered in any order, e.g. component (A) first and then component (B); or component (B) first and then component (A).

The ratio of the total amounts of component (A) to component (B) to be administered in the combined preparation can be varied, e.g. in order to cope with the needs of a patient sub-population to be treated or the needs of the single patient which different needs can be due to age, sex, body weight, etc. of the patients.

Components (A) and (B), whether present in a single composition or in separate compositions, may independently beformulated with one or morepharmaceutically-acceptable carriers. The pharmaceutical combinations of the invention may also include at least one other anti-tumor agent, or an anti-inflammatory or immunosuppressant agent. Examples of therapeutic agents that can be used in combination therapy are described in greater detail below in the section on uses of the antibodies disclosed herein.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion). Depending on the route of administration, the active compound, i.e. antibody, immunoconjugate, or bispecific molecule, may be coated in a material to protect the compound from the action of acids and other natural conditions that may inactivate the compound.

Components (A) and/or (B) may be in the form of one or more pharmaceutically acceptable salts. A "pharmaceutically acceptable salt" refers to a salt that retains the desired biological activity of the parent compound and does not impart any undesired toxicological effects [see, e.g. Berge, S. M., et al. (1977) *J. Pharm. Sci.* 66:1-19]. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical combination of the invention or part thereof also may include a pharmaceutically acceptable anti-oxidant. Examples of pharmaceutically acceptable anti-oxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical combinations of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These combinations or parts thereof may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of 100 percent, this amount will range from about 0.01 percent to about 99 percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g. a synergistic combination, a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the anti-LY75 or anti-CD20 antibody, the dosage ranges from about 0.0001 to 100 mg/kg, for example, 0.001 to 50 mg/kg, 0.005 to 20 mg/kg, 0.01 to 10 mg/kg and more usually 0.01 to 5 mg/kg, of the host body weight. For example dosages can be 0.05 mg/kg body weight, 0.1 mg/kg body weight, 0.3 mg/kg body weight, 0.3 mg/kg body weight, 0.5 mg/kg body weight, 1 mg/kg body weight, 2 mg/kg body weight, 3 mg/kg body weight, 4 mg/kg body weight, 5 mg/kg body weight 6 mg/kg body weight, 7 mg/kg body weight, 8 mg/kg body weight, 9 mg/kg body weight, 10 mg/kg body weight, 12 mg/kg body weight, 15 mg/kg body weight, 20 mg/kg body weight, 25 mg/kg body weight, 30 mg/kg body weight, or within the range of 0.1-20 mg/kg, 0.5-15 mg/kg, 1-10 mg/kg, 2-8 mg/kg, 3-7 mg/kg, 4-6 mg/kg. An exemplary treatment regime entails administration once per day, once every 2 days, once per week, once every two weeks, once every three weeks, once every four weeks, once a month, once every 6 weeks, once every 3 months or once every three to 6 months. Preferred dosage regimens for an anti-LY75 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some embodiments, the anti-LY75 antibody (e.g. LY75-DM4) dosage is adjusted to achieve a plasma antibody concentration of 0.01 to 1.5 nm or 0.018 to 1.2 nM (e.g. about 0.018, 0.037, 0.075, 0.15, 0.3, 0.6 or 1.2 nM). Preferably, the anti-LY75 antibody is adjusted to achieve a plasma antibody concentration of 0.03 nM to 0.30 nm.

In some embodiments, the anti-CD20 antibody is formulated in a 10 mg/ml solution. In some embodiments, the anti-CD20 antibody is administered i.v. at a dose of 350-400 $mg/m^2$, preferably once weekly. In some embodiments, the anti-CD20 antibody (e.g. Rituximab) dosage is adjusted to achieve a plasma antibody concentration of about 2.34 to 150 nM (e.g. about 2.34, 4.68, 9.37, 18.75, 37.5, 75 or 150 nM). The anti-CD20 antibody (e.g. Rituximab) may be administered at a dose of about 1400 mg/23,400 units subcutaneously. In some embodiments, the dose is 200 mg, 400 mg, 600 mg, 800 mg, 1000 mg or 1200 mg. The anti-CD20 antibody (e.g. Rituximab) may be administered with one or more of cyclophosphamide, hydroxydaunorubicin, oncovin and predisone or prednisolone (i.e. CHOP therapy).

In some embodiments, the Ibrutinib dosage is adjusted to achieve a plasma concentration of about 15.6 to 1000 nM (e.g. about 15.6, 31.2, 62.5, 125, 250, 500 or 1000 nM). In other embodiments, the Ibrutinib dosage is adjusted to achieve a plasma concentration of about 1.56 to 100 nM (e.g. about 1.5, 3.1, 6.2, 12.5, 25, 50 or 100 nM). The Ibrutinib dose may be about 560 mg (e.g. four 140 mg capsules). It may be orally administered. In some embodiments, the Ibrutinib dose is about 100 mg, 200 mg, 300 mg, 400 mg or 500 mg.

Preferably, the combination of components (A) and (B) is a synergistic combination. The skilled person will understand that a synergistic combination is one wherein the effect of the combination is greater than the sum of the effects of the individual components. Synergism may be quantified using the Chou-Talalay combination index (CI) (see "Evaluation of combination chemotherapy: integration of nonlinear regression, curve shift, isobologram, and combination index analyses", Zhao L, et al. Clin Cancer Res. (2004) Dec 1;10(23):7994-8004; and "Computerized quantitation of synergism and antagonism of taxol, topotecan, and cisplatin against human teratocarcinoma cell growth: a rational approach to clinical protocol design", Chou TC, Motzer RJ, Tong Y, Bosl GJ., J. Natl. Cancer Inst. (1994) Oct 19;86 (20):1517-24). This combination index (CI) method is based on the multiple drug effect equation derived from the median-effect principle of the mass-action law. This provides a quantitative definition for strong synergism (CI<0.3), synergism (CI=0.3-0.9), additive effect (CI=0.9-1.1) or antagonism/no benefit (CI>1.1), and it provides the algorithm for computer software for automated simulation for drug combinations. It takes into account both the potency (the D(m) value) and the shape of the dose-effect curve (the m value) of each drug alone and their combination. The Chou-Talalay combination index (CI) may be estimated using the Synergy R package (see "Preclinical versus Clinical Drugs Combination Studies", Chou TC. Leuk. Lymphoma. (2008);49(11):2059-2080, and references therein, all of which are specifically incorporated herein by reference). The CI of the combination may be tested in a suitable cell-line, e.g. in ABC-DLBLC cell lines (such as TMD8 or HBL1), e.g. under the conditions used in Example 26.

Preferably, the pharmaceutical combination of the invention is a synergistic combination wherein the Chou-Talalay combination index (CI) is less than 0.9, 0.8, 0.7, 0.6, 0.5, 0.4, 0.3 or 0.2. Preferably, the CI is 0.1-0.5, 0.1-0.3 or 0.1-0.2.

In particular, there is provided a method of treating cancer in a patient comprising simultaneously, sequentially or separately administering to a patient in need thereof therapeutically-effective synergistic amounts of components (A) and (B) of a pharmaceutical combination of the invention. Also provided is a pharmaceutical combination of the invention for use in the treatment of cancer, wherein synergistic amounts of components (A) and (B) are simultaneously, separately or sequentially administered to the patient for the treatment of the cancer. Preferably, amounts of components (A) and (B) are administered to the patient in order to provide the plasma concentrations disclosed above.

Also provided is the use of synergistic amounts of components (A) and (B) of the pharmaceutical combination of the invention in the manufacture of a pharmaceutical combination for simultaneous, separate or sequential use for the treatment of cancer. Also provided is a synergistic pharmaceutical combination of the invention for use in therapy or for use as a medicament.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, daily, twice weekly, weekly, monthly, every three months, every six months, or yearly. Intervals can also be irregular as indicated by measuring blood levels of antibody to the target antigen in the patient. In some methods, dosage is adjusted to achieve a plasma antibody concentration of about 1-1000 μg/ml, 5-750 μg/ml, 10-600 μg/ml, 15-500 μg/ml, 20-400 μg/ml and in some methods about 25-300 μg/ml.

Alternatively, the anti-LY75 and or anti-CD20 antibodies can be administered as sustained release formulations, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical combinations of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-LY75 antibody or anti-CD20 antibody preferably results in a decrease in severity of disease symptoms, an increase in frequency and duration of disease symptom-free periods, or a prevention of impairment or disability due to the disease affliction. For example, for the treatment of the LY75 or CD20 mediated tumors, a "therapeutically effective dosage" preferably inhibits cell growth or tumor growth by at least about 20%, at least about 30%, more preferably by at least about 40%, at least about 50% even more preferably by at least about 60%, at least about 70% and still more preferably by at least about 80% or at least about 90%, relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A pharmaceutical combination of the present invention can be administered via one or more routes of administration using one or more of a variety of methods known in the art. Components (A) and (B) may be administered by the same route or by different routes. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, the anti-LY75 or anti-CD20 antibody can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art [see, e.g. *Sustained and Controlled Release Drug Delivery Systems* (1978) J. R. Robinson, ed., Marcel Dekker, Inc., N.Y].

Therapeutic compositions can be administered with medical devices known in the art. For example, in a preferred embodiment, component (A) and/or (B) can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-LY75 and/or anti-CD20 antibodies can be formulated to ensure proper distribution in vivo. For example, the blood-brain barrier (BBB) excludes many highly hydrophilic compounds. To ensure that the therapeutic compounds cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery [see, e.g. V. V. Ranade (1989) *J. Clin. Pharmacol.* 29:685]. Exemplary targeting moieties include folate or biotin (see, e.g. U.S. Pat. No. 5,416,016.); mannosides [Umezawa et al. (1988) *Biochem. Biophys. Res. Commun.* 153:1038]; antibodies [P. G. Bloeman et al. (1995) *FEBS Lett.* 357:140; M. Owais et al. (1995) *Antimicrob. Agents Chemother.* 39:180]; surfactant protein A receptor [Briscoe et al. (1995) *Am. J. Physiol.* 1233:134]; p120 [Schreier et al. (1994) *J. Biol. Chem.* 269:9090]; see also K. Keinanen; M. L. Laukkanen (1994) *FEBS Lett.* 346:123; J. J. Killion; I. J. Fidler (1994) *Immunomethods* 4:273.

Uses and Methods

As used herein, the term "subject" is intended to include human and non-human animals. Non-human animals include all vertebrates, e.g. mammals and non-mammals, such as non-human primates, sheep, dogs, cats, cows, horses, chickens, amphibians, and reptiles. Preferred subjects include human patients having disorders mediated by LY75 activity and/or CD20 activity.

The methods are particularly suitable for treating human patients having a disorder associated with the aberrant LY75 expression and/or CD20 expression. Given the expression of LY75 on tumor cells, the combinations and methods of the present invention can be used to treat a subject with a tumorigenic disorder, e.g. a disorder characterized by the presence of tumor cells expressing LY75 or in the manufacture of a medicament for the treatment of such a disorder including, for example leukaemia, including chronic lymphocytic leukaemia and acute myeloid leukaemia, non-Hodgkin's lymphoma, including DLBCL, B-Cell Lymphoma, Follicular Lymphoma, Mantle Cell Lymphoma, Lymphoma of Mucosa-Associated Lymphoid Tissue (MALT), T-Cell/Histiocyte-Rich B-Cell Lymphoma, Burkitt's Lymphoma, Lymphoplasmacytic Lymphoma, Small Lymphocytic Lymphoma, Marginal Zone Lymphoma, T Cell Lymphoma, Peripheral T-Cell Lymphoma, Anaplastic Large Cell Lymphoma and Angiolmmunoblastic T-Cell Lymphoma. LY75 has been demonstrated to be internalised on antibody binding as illustrated in Examples 5 and 7 below, thus enabling the anti-LY75 antibodies to be used in any payload mechanism of action e.g. an ADC approach, radioimmunoconjugate, or ADEPT approach.

The anti-LY75 antibodies, generally administered as ADCs, can be used to inhibit or block LY75 function which, in turn, can be linked to the prevention or amelioration of certain disease symptoms, thereby implicating the LY75 as a mediator of the disease. This can be achieved by contacting a sample and a control sample with the anti-LY75 antibody under conditions that allow for the formation of a complex between the antibody and LY75. Any complexes formed between the antibody and the LY75 are detected and compared in the sample and the control.

Suitable routes of administering the antibody compositions (e.g. monoclonal antibodies, and immunoconjugates) in vivo and in vitro are well known in the art and can be selected by those of ordinary skill. For example, the antibody compositions can be administered by injection (e.g. intravenous or subcutaneous). Suitable dosages of the molecules used will depend on the age and weight of the subject and the concentration and/or formulation of the antibody composition.

As previously described, the anti-LY75 and/or anti-CD20 antibodies can be co-administered with one or other more therapeutic agents, e.g. a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g. an anti-cancer therapy, e.g. radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Other agents suitable for co-administration with the antibodies of the invention include other agents used for the treatment of cancers, e.g. gastric cancer, colorectal cancer, prostate cancer, breast cancer, ovarian cancer or lung cancer, such as Avastin®, 5FU and gemcitabine. Co-administration of the anti-LY75 antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

The pharmaceutical combinations of the invention can also be administered together with serum and/or complement. These compositions can be advantageous when the complement is located in close proximity to the antibodies. Alternatively, the antibodies, and the complement or serum can be administered separately.

Also within the scope of the present invention are kits comprising components (A) and (B), together with instructions for use. The kit can further contain one or more additional reagents, such as an immunosuppressive reagent, a cytotoxic agent or a radiotoxic agent, or one or more additional antibodies (e.g. an antibody having a complementary activity which binds to an epitope in the LY75 antigen distinct from the first antibody).

Accordingly, patients treated with pharmaceutical combinations of the invention can be additionally administered (prior to, simultaneously with, or following administration of an antibody disclosed herein) with another therapeutic agent, such as a cytotoxic or radiotoxic agent, which enhances or augments the therapeutic effect of the antibodies.

In other embodiments, the subject can be additionally treated with an agent that modulates, e.g. enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependent claims.

The present invention is further illustrated by the following examples which should not be construed as further limiting.

Example 1: Generation of Human Monoclonal Antibodies Against LY75-Antigen

Following standard procedures, mice (xenomouse IgG1) were immunized with CHO cells transfected with full length LY75.

The specificity of antibodies raised against the LY75 was tested by flow cytometry on HEK293 cells transfected with LY75 and subsequently on LY75-expressing HT29 cells. To test the ability of the antibodies to bind to the cell surface LY75 protein, the antibodies were incubated with the LY75-expressing cells. Cells were washed in FACS buffer (DPBS, 2% FBS), centrifuged and resuspended in 100 μl of the diluted primary LY75 antibody (also diluted in FACS buffer). The antibody-cell line complex was incubated on ice for 60 min and then washed twice with FACS buffer as described above. The cell-antibody pellet was resuspended in 100 μl of the diluted secondary antibody (also diluted in FACS buffer) and incubated on ice for 60 min on ice. The pellet was washed as before and resuspended in 200 μl FACS buffer. The samples were loaded onto the BD FACScanto II flow cytometer and the data analyzed using the BD FACSdiva software (results not shown).

Example 2: Structural Characterization of Monoclonal Antibodies to LY75

The cDNA sequences encoding the heavy and light chain variable regions of the LY75_A1 monoclonal antibody were obtained using standard PCR techniques and were sequenced using standard DNA sequencing techniques.

The antibody sequences may be mutagenized to revert back to germline residues at one or more residues.

The nucleotide and amino acid sequences of the heavy chain variable region of LY75_A1 are shown in SEQ ID NO: 3 and 1, respectively.

The nucleotide and amino acid sequences of the light chain variable region of LY75_A1 are shown in SEQ ID NO: 4 and 2, respectively.

Comparison of the LY75_A1 heavy chain immunoglobulin sequence to the known human germline immunoglobulin heavy chain sequences demonstrated that the LY75_A1 heavy chain utilizes a $V_H$ segment from human germline $V_H$ 3-15 and a $J_H$ segment from human germline $J_H$ JH4. Further analysis of the LY75_A1 $V_H$ sequence using the Kabat system of CDR region determination led to the delineation of the heavy chain CDR1, CDR2 and CDR3 regions as shown in SEQ ID NOs: 5, 6 and 7, respectively. The alignments of the LY75_A1 CDR1, CDR2 and CDR3 $V_H$ sequences to the germline $V_H$ 3-15 and germline $J_H$ JH4 sequence are shown in FIG. 1.

Comparison of the LY75_A1 light chain immunoglobulin sequence to the known human germline immunoglobulin light chain sequences demonstrated that the LY75_A1 light chain utilizes a $V_K$ segment from human germline $V_K$ O12 and a $J_K$ segment from human germline $J_K$ JK4. Further analysis of the LY75_A1 $V_K$ sequence using the Kabat system of CDR region determination led to the delineation of the light chain CDR1, CDR2 and CDR3 regions as shown in SEQ ID NOs: 8, 9 and 10, respectively. The alignments of the LY75_A1 CDR1, CDR2 and CDR3 $V_K$ sequences to the germline $V_K$ O12 and germline $J_K$ JK4 sequences are shown in FIG. 2.

Example 3: Immunohistochemistry Using Monoclonal Antibody to LY75

Using the human monoclonal antibodies specific to LY75, immunohistochemistry was performed on FFPE HT-29 and A549 cell pellets, FFPE non-Hodgkin's lymphoma and pancreatic cancer arrays, and fresh frozen lymphoma/leukaemia tumours, ovarian cancer, pancreatic cancer, and breast cancer sections and a normal tissue array.

Materials and Methods

Materials

Xylenes (X5P-1 gal) from Fisher Scientific, PA, USA.

Histoprep 100% ethanol (HC-800-1 GAL) from Fisher Scientific, PA, USA.

10× Citrate buffer for heat induced epitope retrieval (AP9003125) from Thermo Scientific, MA, USA.

Thermo Scientific* Pierce* Peroxidase Suppressor (35000) from Thermo Scientific, MA, USA.

Serum free protein block (X0909) from Dako, CA, USA

Secondary antibody: goat anti-human IgG Fab-FITC conjugated (109-097-003) from Jackson Immunoresearch, PA, USA Chrome pure Human IgG, whole molecule (09-000-003) from Jackson Immunoresearch, PA, USA Tertiary antibody: mouse anti-FITC (ab10257) from Abcam, MA, USA Purified human IgG isotype control (1-001A) from R&D Systems, MN, USA Tween-20 (BP337-100) from Fisher Scientific, PA, USA Acetone (BP2403-4) from Fisher Scientific, PA, USA Dual Link EnVision+HRP-conjugated polymer, Mouse and Rabbit (K4063) from Dako, CA, USA.

DAB 2-solution kit (882014) from Invitrogen, NY, USA.

Harris Hematoxylin (23-245-677) from Fisher Scientific, PA, USA.

Faramount mounting media (S302580) from Dako, CA, USA.

Tissue sections and arrays were purchased from US Biomax Inc., MD, USA or Origene, MD, USA.

Preparation of FFPE Slides: Deparaffinisation and Rehydration

FFPE slides were deparaffinised in xylene (2×3 minutes) then rehydrated through 1:1 xylene: 100% ethanol (1×3 minutes), 100% ethanol (2×3 minutes), 95% ethanol (1×3 minutes), 70% ethanol (1×3 minutes), 50% ethanol (1×3 minutes), and tap water (1×3 minutes).

Preparation of FFPE Slides: Antigen Retrieval (Microwave)

The LY75 antigen was retrieved using microwave heat, high power until boiling then low power for 10 minutes in 50 mL 1× citrate buffer in a Coplin jar. Slides were then left to cool to room temperature for a further 15 min, then washed in tap water, 3 minutes. Circles were drawn around each tissue section/TMA with a hydrophobic barrier pen and slides were then washed 3 times in PBS, 3 minutes each wash.

Preparation of FF Slides

Slides were removed from storage at −80 C and allowed to dry at room temperature in the fume hood for 20-30 minutes. The slides were fixed for 10 min in ice cold acetone at −20 C, then allowed to dry for 20 min in the fume hood at room temperature. Slides were washed and rehydrated in PBS, 3 washes for 3 min each. Sections were outlined with a hydrophobic barrier pen.

Preparation of Antibody Complexes

The primary anti-LY75 antibody was diluted in serum free protein block (SFPB) to obtain a solution with a concentration 20-fold greater than the final desired concentration (20 μg/mL for 1 μg/mL final). The secondary antibody, goat anti-human immunoglobulin G (IgG) antigen-binding fragment (Fab), was prepared similarly in SFPB to create a solution of equal concentration.

Equal volumes of primary and secondary antibodies were combined in a labelled tube, gently mixed, and incubated for 3 minutes at room temperature, resulting in a primary antibody concentration 10-fold greater than the desired final concentration (10 μg/mL for 1 μg/mL final). This mixture was diluted 1:5 with SFPB, gently mixed, and incubated for 30 minutes at room temperature, resulting in a primary antibody concentration twice that of the desired final concentration (2 μg/mL for 1 μg/mL final).

To produce the final staining complexes, a 1% (10 μg/μL) solution of human IgG was prepared in SFPB and equal volume added to the primary/secondary antibody mixture. This combination was gently mixed and incubated at room temperature for 30 minutes, diluting by half the primary antibody concentration of the primary/secondary antibody mixture and resulting in the desired final primary antibody concentration (1 μg/mL).

Immunostaining

Meanwhile, endogenous tissue peroxidase activity was blocked by incubating tissues with peroxidase suppressor for 5-10 minutes at RT in a humidified chamber. Slides were then washed in PBS 3×3 minutes each wash. Tissues were incubated in SFPB for 30 minutes at room temperature in a humidified chamber. Final staining complexes were applied to each tissue section and/or microarray, and the slides were incubated for 30 min at room temperature in a humidified chamber. Slides were then washed once in PBS and once in PBST (PBS+0.125% Tween-20), 3 minutes each wash. The tertiary antibody mouse anti-FITC, was applied at 2 μg/mL concentration for 30 min, room temperature, in a humidified chamber. Sections were then washed once in PBS and once in PBST, 3 min each wash. Dual Link EnVision+anti-mouse/rabbit-HRP-conjugated polymer was then applied to the tissues and the slides were incubated for 30 min at room temperature in a humidified chamber. Slides were then washed once in PBS, once in PBST, 3 minutes each wash. Tissues were incubated in DAB solution prepared according to the manufacturer's instructions at room temperature for 10 min. Slides were then washed once in running tap water for 2 minutes and once in PBS for 3 minutes. The slides were counterstained with Hematoxylin for 30 seconds at room temperature, and washed with running tap water. The slides were dried at room temperature for 30 minutes and coverslips were then mounted onto the slides using Faramount mounting media.

Results

LY75_A1 showed positivity in FFPE Triple Negative breast cancer samples, where 77% of the sections showed positive staining and 55% exhibited robust (+++) staining.

Staining for LY75 in FF normal tissues was generally absent to low. Ductal epithelium of the breast, salivary gland, and pancreas exhibited marked low to moderate staining, and the spleen stained low positive. Therefore antibodies directed to LY75 may have utility as therapeutics and diagnostics in some of the tested cancers and possibly other cancer types showing expression of LY75.

Example 4: Efficacy of DM1-Conjugated Anti-LY75 Monoclonal Antibodies in HT-29 Cells Materials Cell stripper (Non-enzymatic cell dissociation) (MT-25-056CI) from Fisher Scientific, PA, USA.

PBS pH 7.4 (1×) (SH30028LS) from Fisher Scientific, PA, USA.

RPMI 1640 Media (MT-10-041-CM) from Fisher Scientific, PA, USA.

Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

The results depicted in FIG. 3*a* show a subpopulation of antibodies, know to bind to LY75, which can induce cell kill of HT-29 cells. This suggests while antibodies can bind to LY75 only a few display efficacy when conjugated to DM1. Antibodies where then chosen from the subpopulation for further cytotoxic activity analysis.

Example 5: Efficacy of DM1-Conjugated and DM4-Conjugated Anti-LY75 Monoclonal Antibodies in Colorectal Cancer Cells Materials

- Cell stripper (Non-enzymatic cell dissociation) (MT-25-056CI) from Fisher Scientific, PA, USA.
- PBS pH 7.4 (1×) (SH30028LS) from Fisher Scientific, PA, USA.
- RPMI 1640 Media (MT-10-041-CM) from Fisher Scientific, PA, USA.
- Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3B:
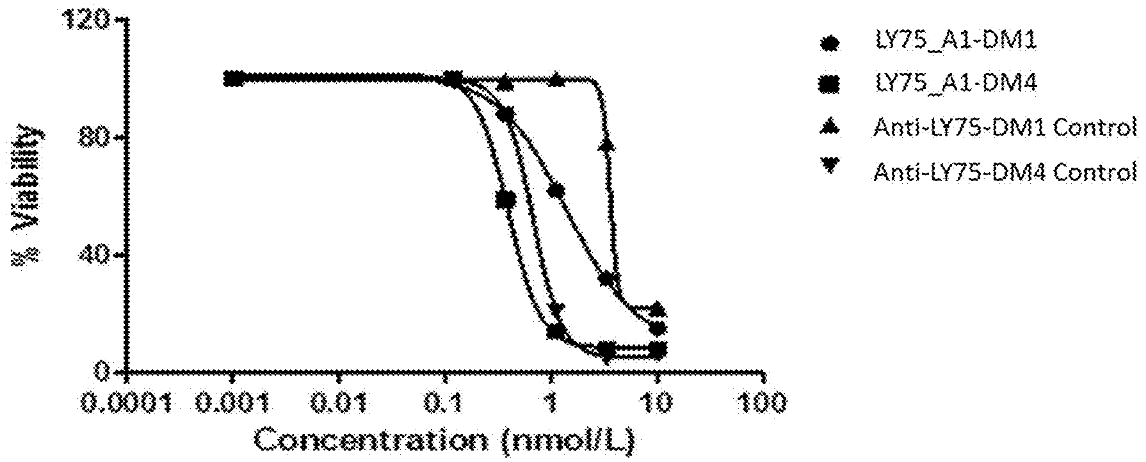
FIG. 3*b* depicts cytotoxic activity of anti-LY75 antibodies conjugated to either DM1 or DM4 in HT-29.

FIG. 3*b* shows the cytotoxic activity of anti-LY75 antibodies conjugated to DM1 and DM4 towards HT-29 cells These results demonstrate an increase in cytotoxic activity proportional to antibody concentration and other anti-LY75 antibodies conjugated to a toxin (selected from Example 1).

Example 6: Efficacy of DM1-Conjugated and DM4-Conjugated Anti-LY75 Monoclonal Antibodies in Lymphoma Cell Lines Materials

- Cell stripper (Non-enzymatic cell dissociation) (MT-25-056CI) from Fisher Scientific, PA, USA.
- PBS pH 7.4 (1×) (SH30028LS) from Fisher Scientific, PA, USA.
- RPMI 1640 Media (MT-10-041-CM) from Fisher Scientific, PA, USA.
- Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3C:
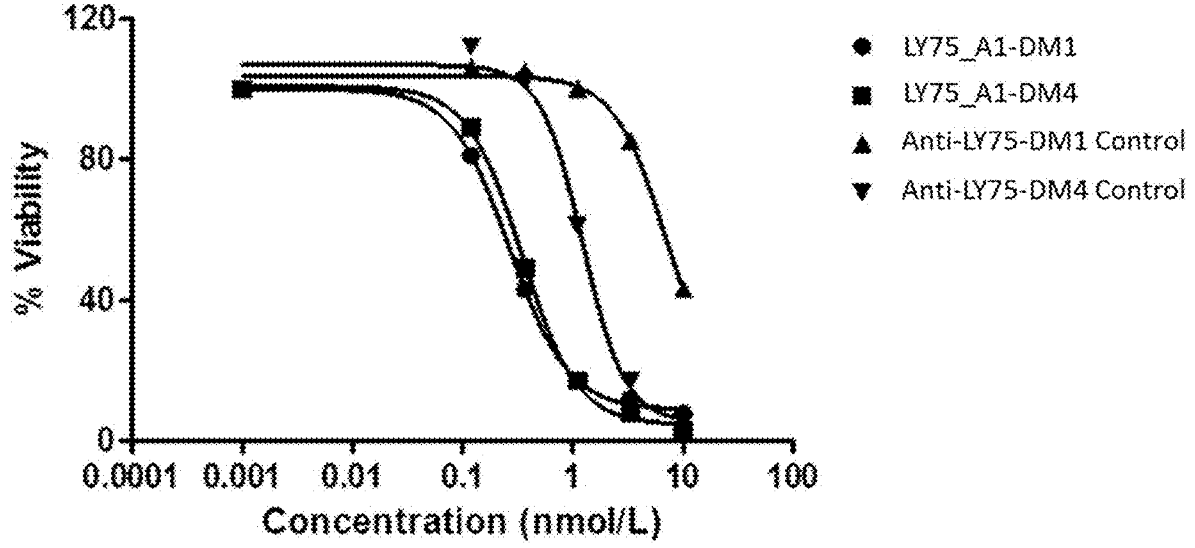
FIG. 3*c* depicts cytotoxic activity of anti-LY75 antibodies conjugated to either DM1 or DM4 in RAJI cells.
Figure 3D:
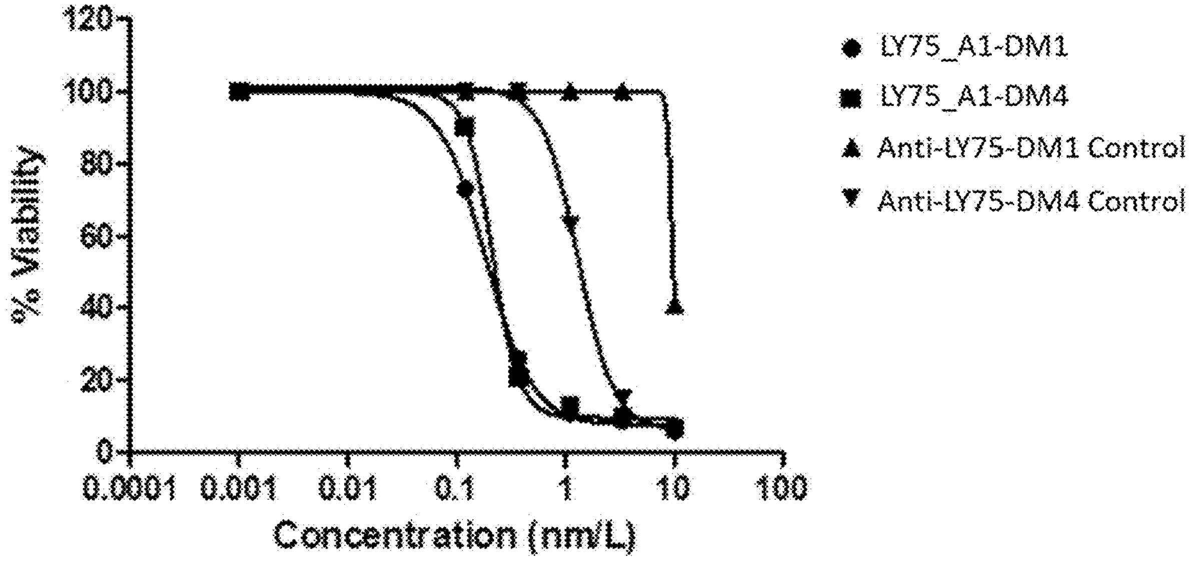
FIG. 3*d* depicts cytotoxic activity of anti-LY75 antibodies conjugated to either DM1 or DM4 in Namalwa cells.
Figure 3E:
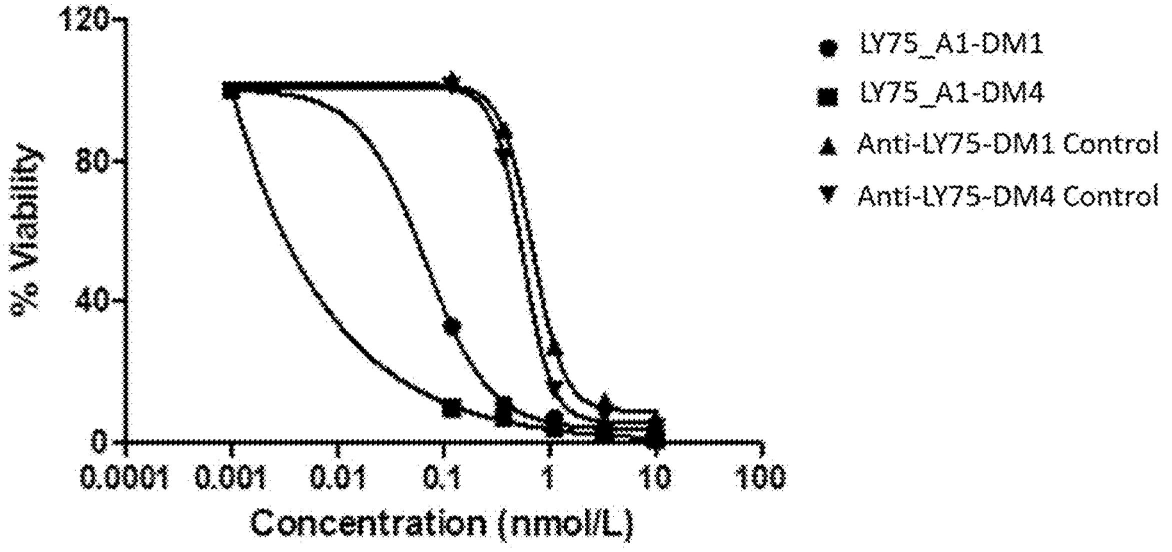
FIG. 3*e* depicts cytotoxic activity of anti-LY75 antibodies conjugated to either DM1 or DM4 in Karpas 299cells.

FIG. 3*c* shows the cytotoxic activity of anti-LY75 antibodies conjugated to DM1 and DM4 towards RAJI cells. FIG. 3*d* shows the cytotoxic activity of anti-LY75 antibodies conjugated to DM1 and DM4 towards Namalwa cells. FIG. 3*e* shows the cytotoxic activity of anti-LY75 antibodies conjugated to DM1 and DM4 towards Karpas 299 cells. These results demonstrates an increase in cytotoxic activity proportional to antibody concentration and other anti-LY75 antibodies conjugated to DM1 and DM4 (selected from Example 1).

Example 7: Efficacy of DM1-Conjugated and DM4-Conjugated Anti-LY75 Monoclonal Antibodies in Pancreatic Cancer Cell Lines Materials

- Cell stripper (Non-enzymatic cell dissociation) (MT-25-056CI) from Fisher Scientific, PA, USA.

PBS pH 7.4 (1×) (SH30028LS) from Fisher Scientific, PA, USA.

RPMI 1640 Media (MT-10-041-CM) from Fisher Scientific, PA, USA.

Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3F:
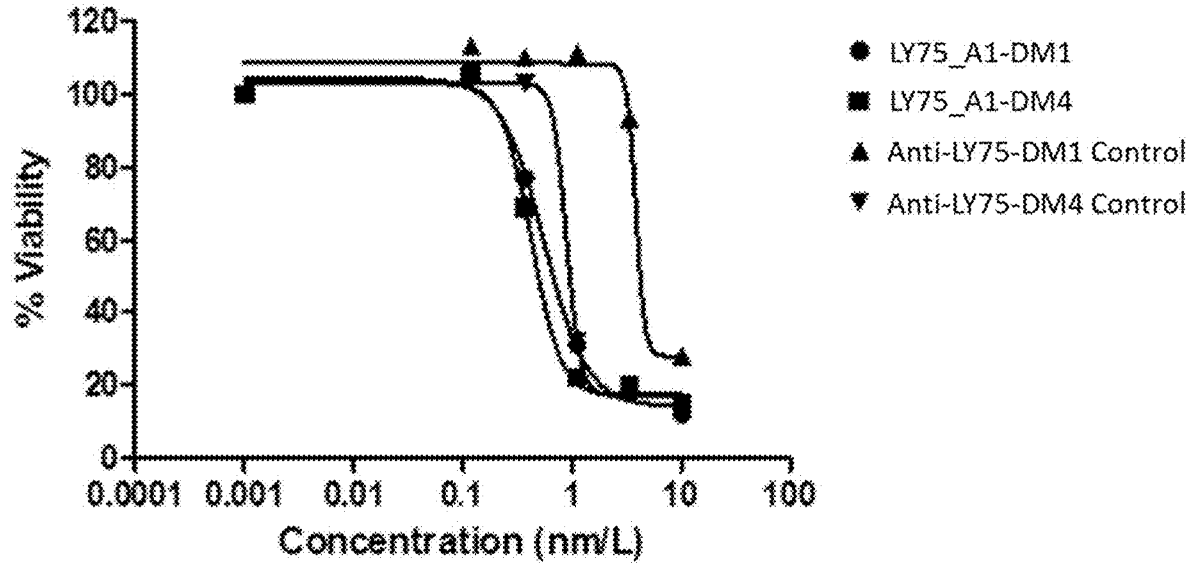
FIG. 3*f* depicts cytotoxic activity of anti-LY75 antibodies conjugated to either DM1 or DM4 in BxPC3 cells.
Figure 3G:
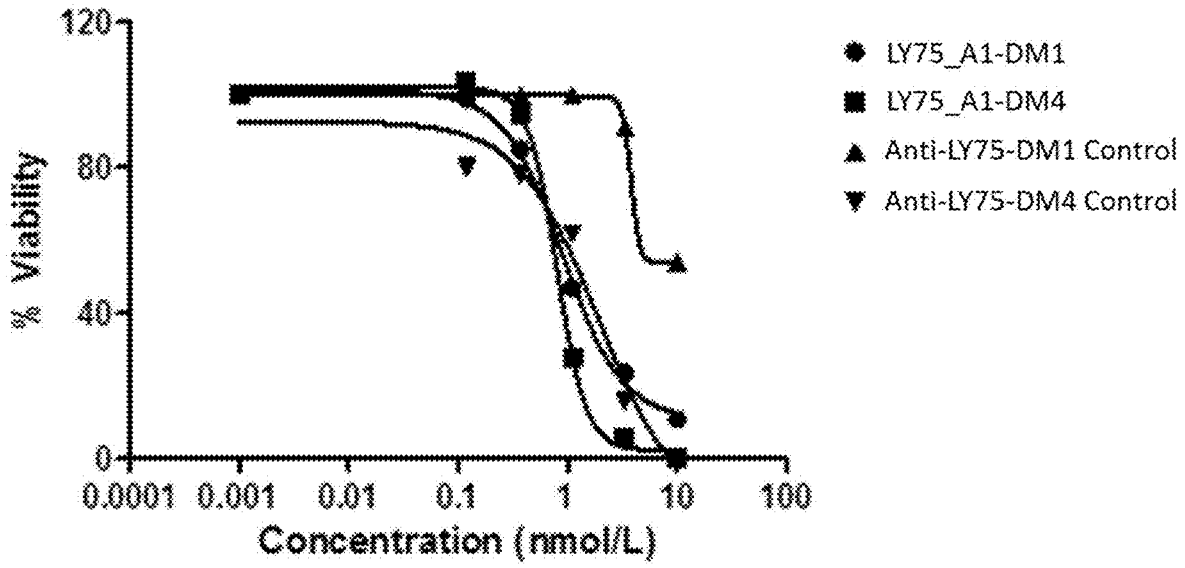
FIG. 3*g* depicts cytotoxic activity of anti-LY75 antibodies conjugated to either DM1 or DM4 in HupT4 cells.
Figure 3H:
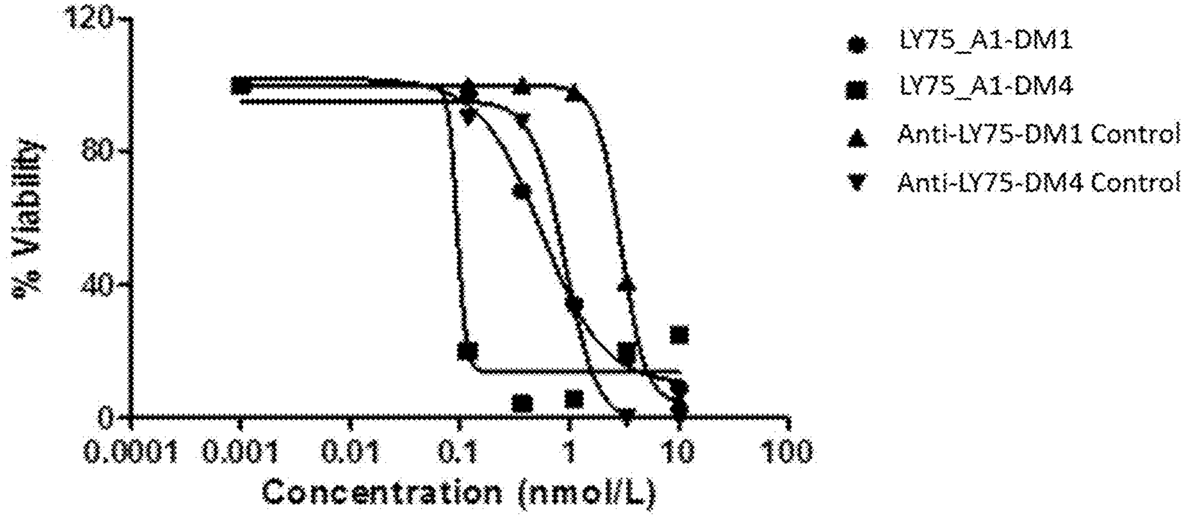
FIG. 3*h* depicts cytotoxic activity of anti-LY75 antibodies conjugated to either DM1 or DM4 in HPAFFII cells.

FIG. 3*f* shows the cytotoxic activity of anti-LY75 antibodies conjugated to DM1 and DM4 towards BxPC3 cells. FIG. 3*g* shows the cytotoxic activity of anti-LY75 antibodies conjugated to DM1 and DM4 towards HupT4 cells. FIG. 3*h* shows the cytotoxic activity of anti-LY75 antibodies conjugated to DM1 and DM4 towards HPAFFII cells. These results demonstrates an increase in cytotoxic activity proportional to antibody concentration and other anti-LY75 antibodies conjugated to DM1 and DM4 (selected from Example 1).

Example 8: Efficacy of DM1-Conjugated and DM4-Conjugated Anti-LY75 Monoclonal Antibodies in Chronic Lymphocytic Leukaemia Cell Lines Materials Cell stripper (Non-enzymatic cell dissociation) (MT-25-056CO) from Fisher Scientific, PA, USA.

PBS pH 7.4 (1×) (SH30028LS) from Fisher Scientific, PA, USA.

RPMI 1640 Media (MT-10-041-CM) from Fisher Scientific, PA, USA.

Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3I:
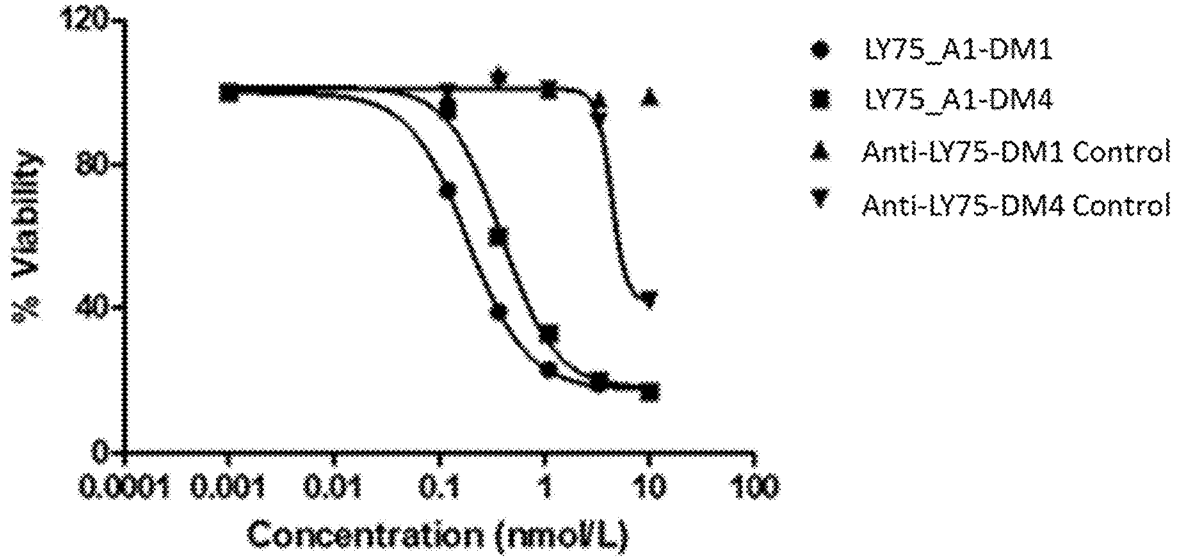
FIG. 3*i* depicts cytotoxic activity of anti-LY75 antibodies conjugated to either DM1 or DM4 in EHEB cells.
Figure 3J:
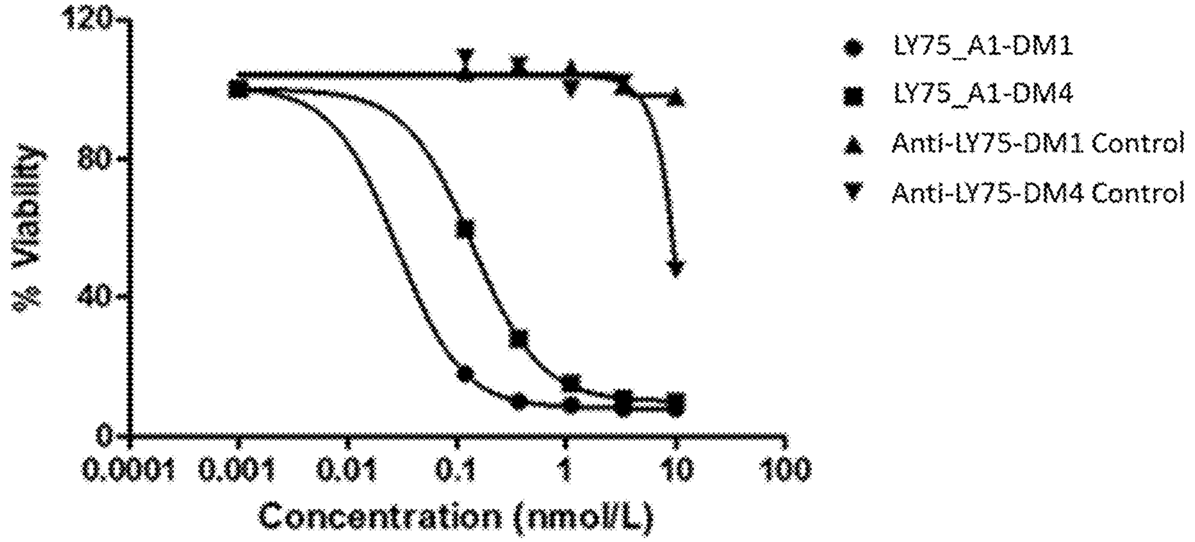
FIG. 3*j* depicts cytotoxic activity of anti-LY75 antibodies conjugated to either DM1 or DM4 in Mec-1 cells.

FIG. 3*i* shows the cytotoxic activity of anti-LY75 antibodies conjugated to DM1 and DM4 towards EHEB cells. FIG. 3*j* shows the cytotoxic activity of anti-LY75 antibodies conjugated to DM1 and DM4 towards Mec-1 cells. These results demonstrates an increase in cytotoxic activity proportional to antibody concentration and other anti-LY75 antibodies conjugated to DM1 and DM4 (selected from Example 1).

Example 9: Efficacy of DM1-Conjugated and DM4-Conjugated Anti-LY75 Monoclonal Antibodies in Acute Monocytic Leukaemia Cell Lines Materials Cell stripper (Non-enzymatic cell dissociation) (MT-25-056CI) from Fisher Scientific, PA, USA.

PBS pH 7.4 (1×) (SH30028LS) from Fisher Scientific, PA, USA.

RPMI 1640 Media (MT-10-041-CM) from Fisher Scientific, PA, USA.

Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3K:
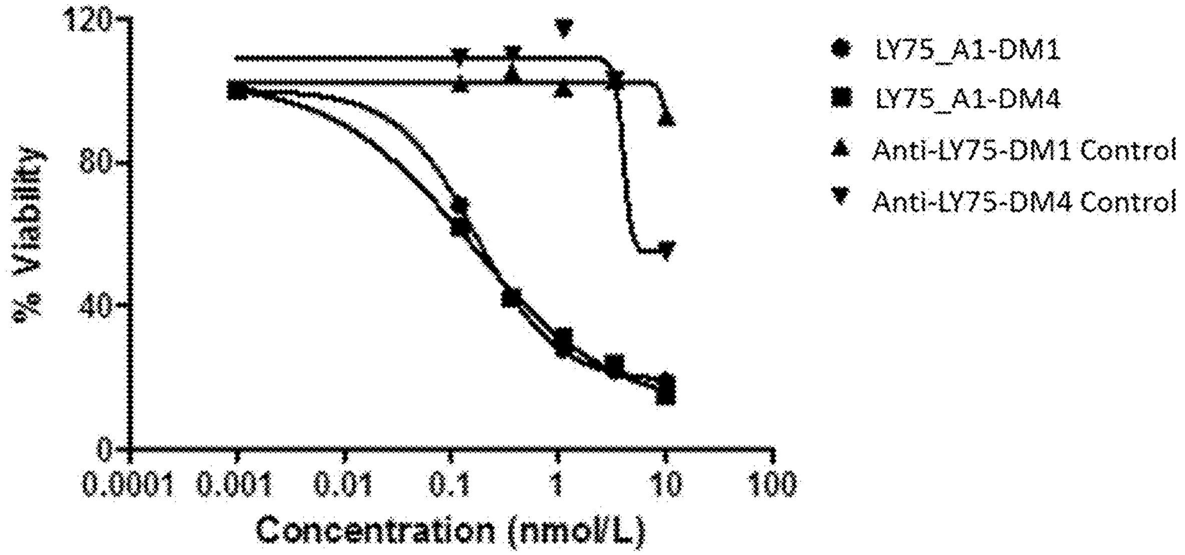
FIG. 3*k* depicts cytotoxic activity of anti-LY75 antibodies conjugated to either DM1 or DM4 in AML-193 cells.

FIG. 3*k* shows the cytotoxic activity of anti-LY75 antibodies conjugated to DM1 and DM4 towards AML-193 cells. These results demonstrates an increase in cytotoxic activity proportional to antibody concentration and other anti-LY75 antibodies conjugated to DM1 and DM4 (selected from Example 1).

Example 10: Efficacy of DM1-Conjugated and DM4-Conjugated Anti-LY75 Monoclonal Antibodies in Breast Cancer Cell Lines Materials Cell stripper (Non-enzymatic cell dissociation) (MT-25-056CI) from Fisher Scientific, PA, USA.

PBS pH 7.4 (1×) (SH30028LS) from Fisher Scientific, PA, USA.

RPMI 1640 Media (MT-10-041-CM) from Fisher Scientific, PA, USA.

Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3L:
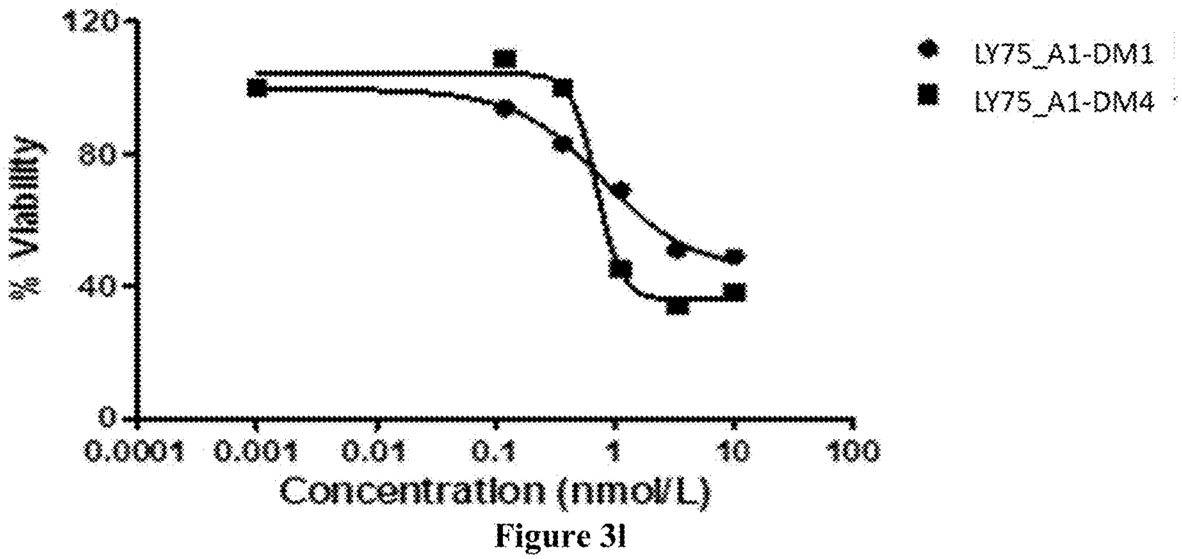
FIG. 3*l* depicts cytotoxic activity of anti-LY75 antibodies conjugated to either DM1 or DM4 in HCC 70 cells.
Figure 3M:
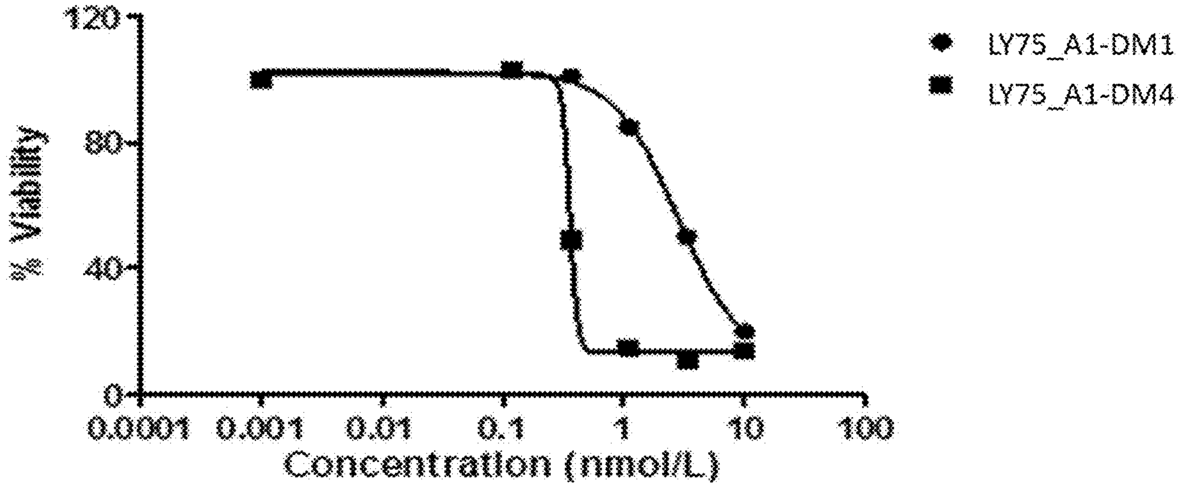
FIG. 3*m* depicts cytotoxic activity of anti-LY75 antibodies conjugated to either DM1 or DM4 in HCC 1806 cells.
Figure 3N:
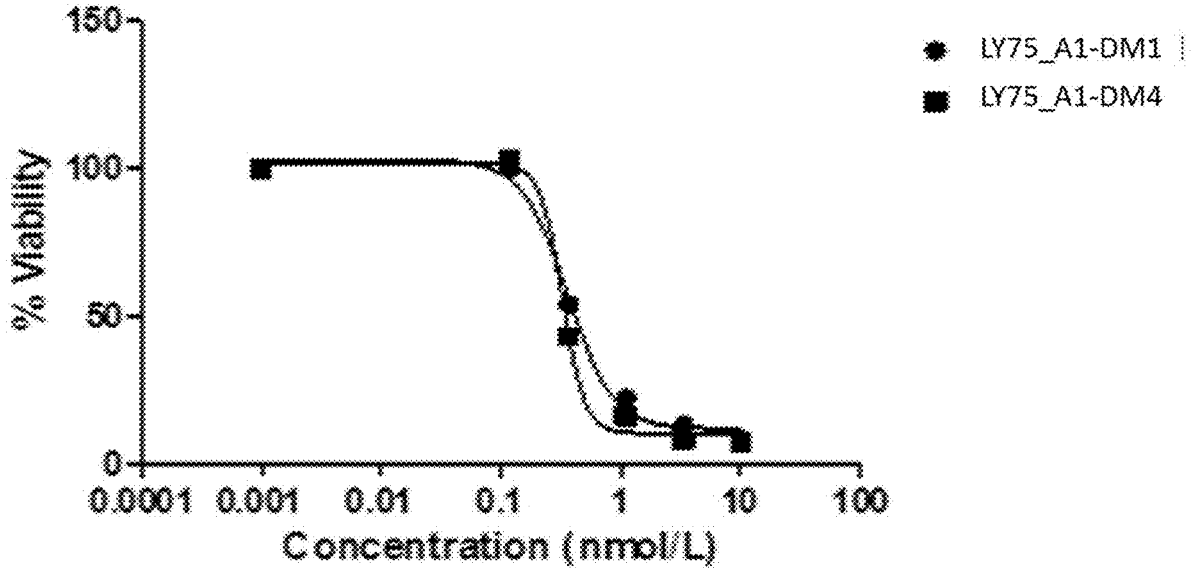
FIG. 3*n* depicts cytotoxic activity of anti-LY75 antibodies conjugated to either DM1 or DM4 in MDA-MB-468 cells.

FIG. 3*l* shows the cytotoxic activity of anti-LY75 antibodies conjugated to DM1 and DM4 towards HCC 70 (ER negative, PR negative and Her2 negative) cells. FIG. 3*m* shows the cytotoxic activity of anti-LY75 antibodies conjugated to DM1 and DM4 towards HCC 1806 (ER negative, PR negative and Her2 negative) cells. FIG. 3*n* shows the cytotoxic activity of anti-LY75 antibodies conjugated to DM1 and DM4 towards MDA-MB-468 cells. These results demonstrates an increase in cytotoxic activity proportional to antibody concentration.

Example 11: Efficacy of DM1-Conjugated and DM4-Conjugated Anti-LY75 Monoclonal Antibodies in Bladder Cancer Cell Lines Materials Cell stripper (Non-enzymatic cell dissociation) (MT-25-056CI) from Fisher Scientific, PA, USA.

PBS pH 7.4 (1×) (SH30028LS) from Fisher Scientific, PA, USA.

RPMI 1640 Media (MT-10-041-CM) from Fisher Scientific, PA, USA.

Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3O:
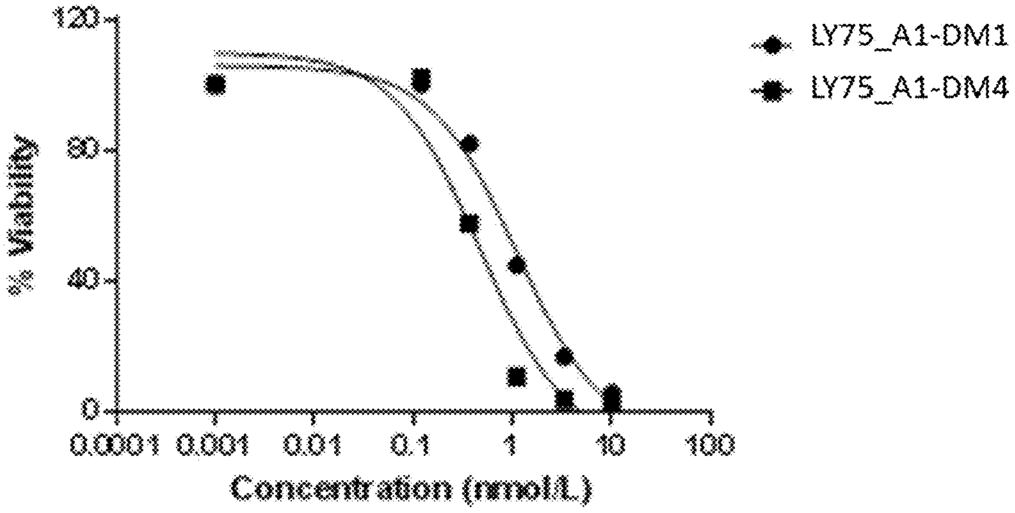
FIG. 3*o* depicts cytotoxic activity of anti-LY75 antibodies conjugated to either DM1 or DM4 in RT4 cells.
Figure 3P:
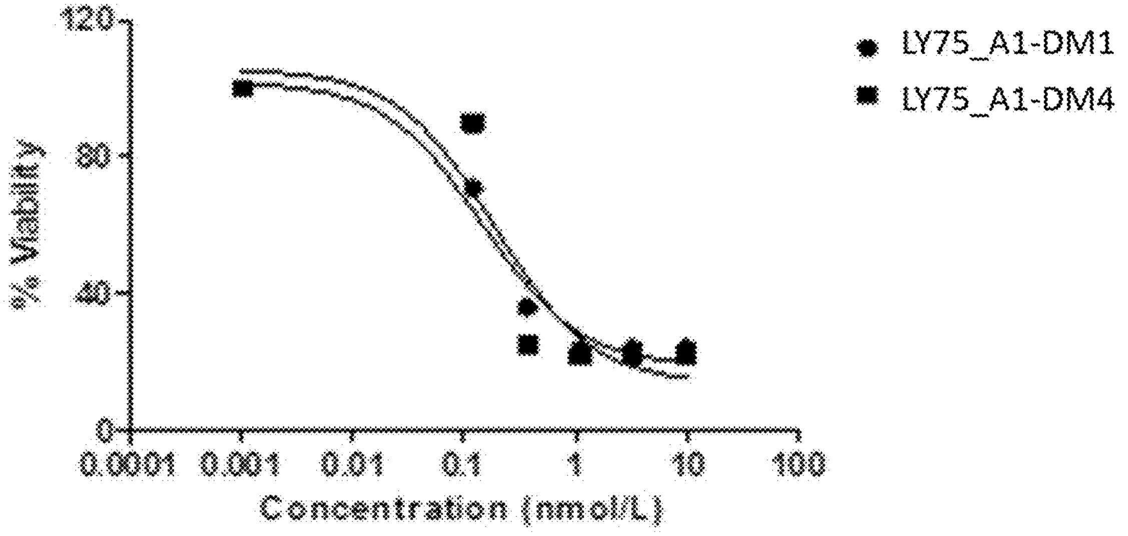
FIG. 3*p* depicts cytotoxic activity of anti-LY75 antibodies conjugated to either DM1 or DM4 in 5637 cells.
Figure 3Q:
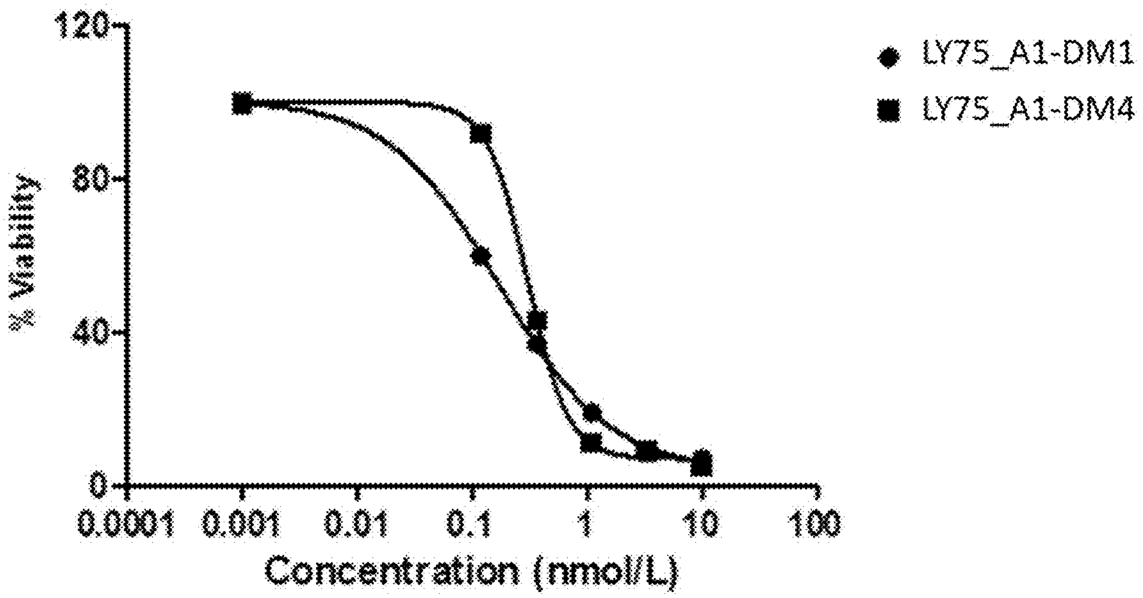
FIG. 3*q* depicts cytotoxic activity of anti-LY75 antibodies conjugated to either DM1 or DM4 in SW780 cells.
Figure 3R:
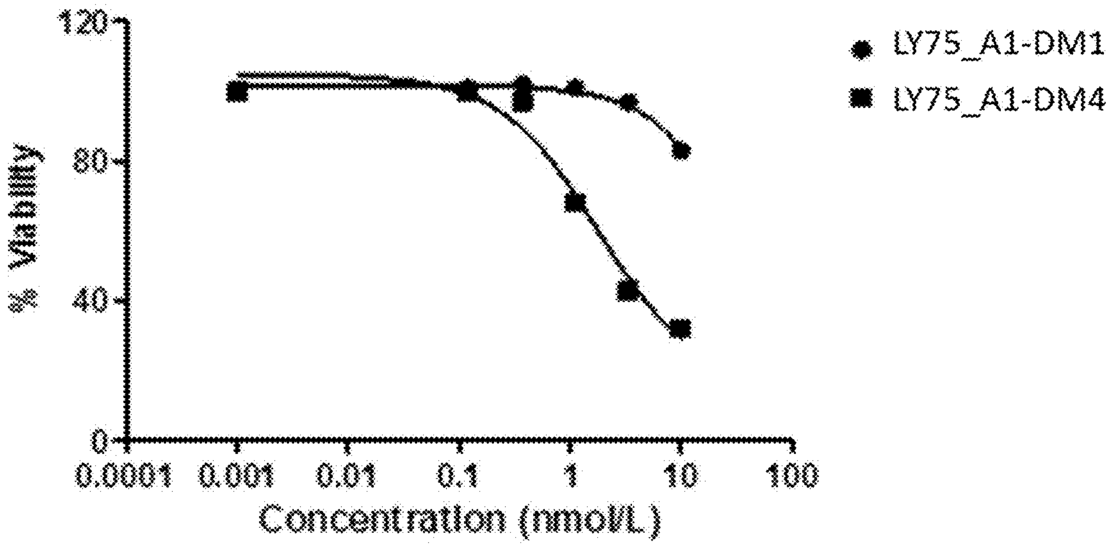
FIG. 3*r* depicts cytotoxic activity of anti-LY75 antibodies conjugated to either DM1 or DM4 in SCC-9 cells.
Figure 3S:
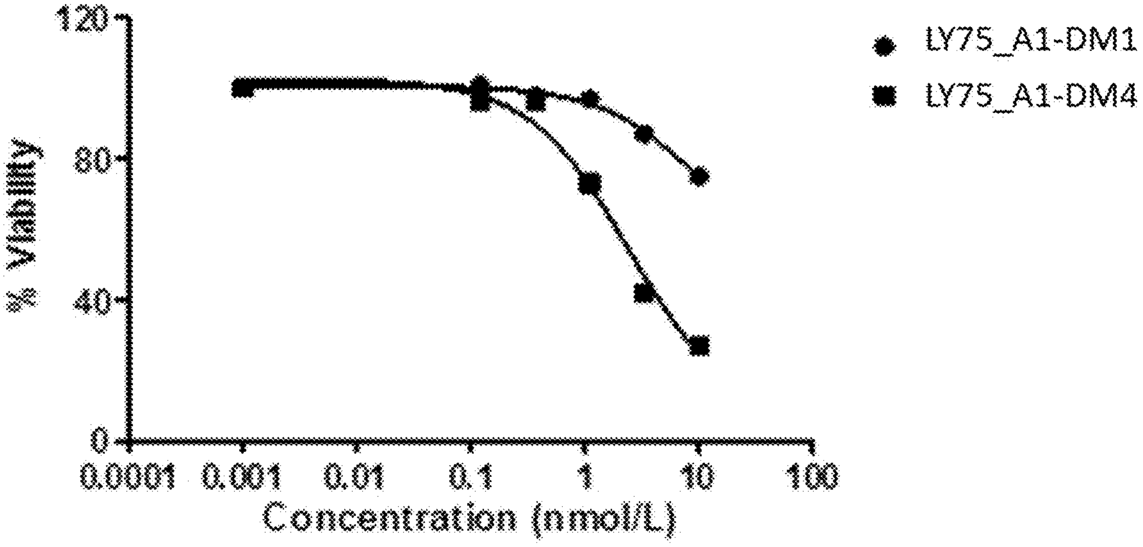
FIG. 3*s* depicts cytotoxic activity of anti-LY75 antibodies conjugated to either DM1 or DM4 in OE 19 cells.
Figure 3T:
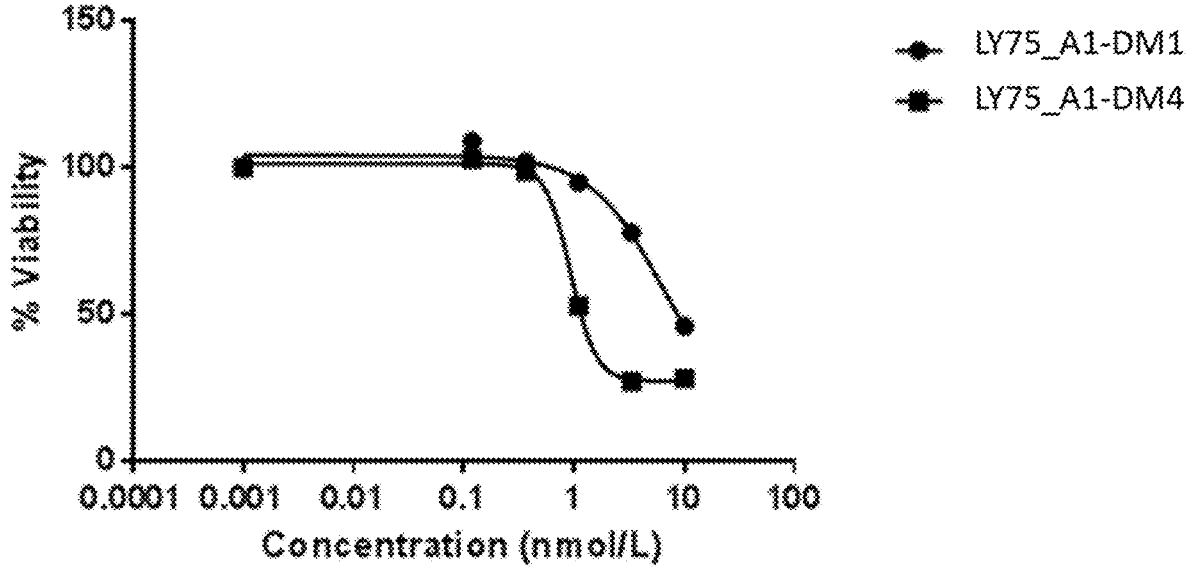
FIG. 3*t* depicts cytotoxic activity of anti-LY75 antibodies conjugated to either DM1 or DM4 in OVCAR-3 cells.

FIG. 3*o* shows the cytotoxic activity of anti-LY75 antibodies conjugated to DM1 and DM4 towards RT4 cells. FIG. 3*p* shows the cytotoxic activity of anti-LY75 antibodies conjugated to DM1 and DM4 towards 5637 cells. FIG. 3*q* shows the cytotoxic activity of anti-LY75 antibodies conjugated to DM1 and DM4 towards SW780 cells. These results demonstrate an increase in cytotoxic activity proportional to antibody concentration.

Example 12: Efficacy of DM1-Conjugated and DM4-Conjugated Anti-LY75 Monoclonal Antibodies in Head and Neck Cancer Cell Lines Materials Cell stripper (Non-enzymatic cell dissociation) (MT-25-056CO) from Fisher Scientific, PA, USA.

PBS pH 7.4 (1×) (SH30028LS) from Fisher Scientific, PA, USA.

RPMI 1640 Media (MT-10-041-CM) from Fisher Scientific, PA, USA.

Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

FIG. **3*r*** shows the cytotoxic activity of anti-LY75 antibodies conjugated to DM1 and DM4 towards SCC-9 cells. These results demonstrate an increase in cytotoxic activity proportional to antibody concentration.

Example 13: Efficacy of DM1-Conjugated and DM4-Conjugated Anti-LY75 Monoclonal Antibodies in Oesophageal Cancer Cell Lines Materials

- Cell stripper (Non-enzymatic cell dissociation) (MT-25-056CI) from Fisher Scientific, PA, USA.
- PBS pH 7.4 (1×) (SH30028LS) from Fisher Scientific, PA, USA.
- RPMI 1640 Media (MT-10-041-CM) from Fisher Scientific, PA, USA.
- Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

FIG. **3*s*** shows the cytotoxic activity of anti-LY75 antibodies conjugated to DM1 and DM4 towards OE 19 cells. These results demonstrate an increase in cytotoxic activity proportional to antibody concentration.

Example 14: Efficacy of DM1-Conjugated and DM4-Conjugated Anti-LY75 Monoclonal Antibodies in Ovarian Cancer Cell Lines Materials

- Cell stripper (Non-enzymatic cell dissociation) (MT-25-056CI) from Fisher Scientific, PA, USA.
- PBS pH 7.4 (1×) (SH30028LS) from Fisher Scientific, PA, USA.
- RPMI 1640 Media (MT-10-041-CM) from Fisher Scientific, PA, USA.
- Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3U:
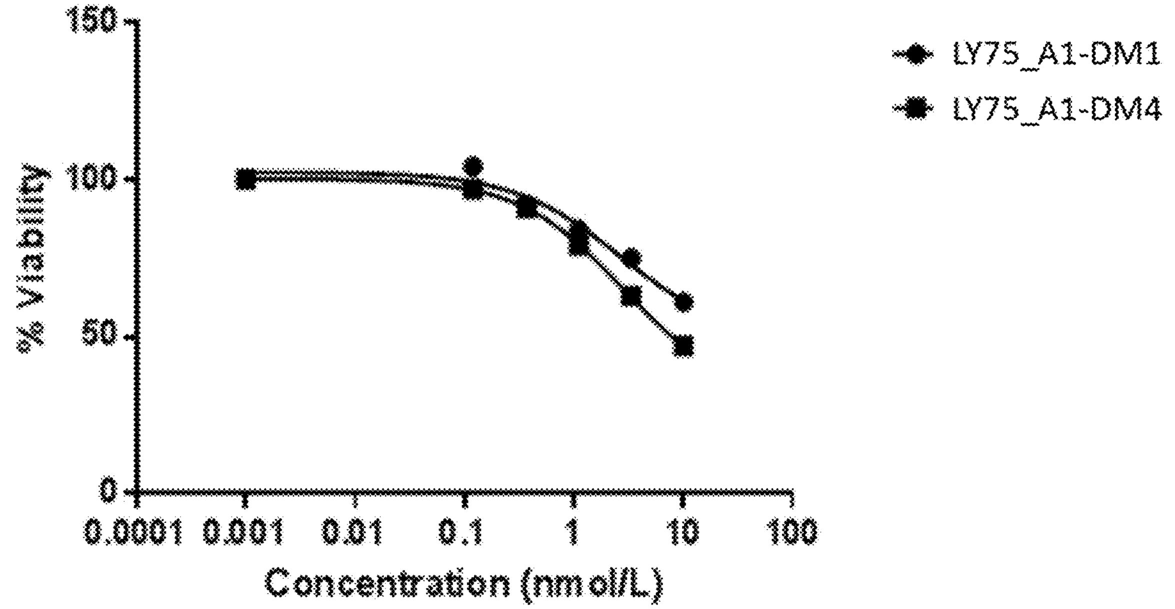
FIG. 3*u* depicts cytotoxic activity of anti-LY75 antibodies conjugated to either DM1 or DM4 in SK-OV-3 cells.

FIG. **3*t* shows the cytotoxic activity of anti-LY75 antibodies conjugated to DM1 and DM4 towards OVCAR-3 cells. FIG. 3*u*** shows the cytotoxic activity of anti-LY75 antibodies conjugated to DM1 and DM4 towards SK-OV-3 cells. These results demonstrate an increase in cytotoxic activity proportional to antibody concentration.

Example 15: Efficacy of DM1-Conjugated and DM4-Conjugated Anti-LY75 Monoclonal Antibodies in Multiple Myeloma Cell Lines Materials

- Cell stripper (Non-enzymatic cell dissociation) (MT-25-056CI) from Fisher Scientific, PA, USA.
- PBS pH 7.4 (1×) (SH30028LS) from Fisher Scientific, PA, USA.
- RPMI 1640 Media (MT-10-041-CM) from Fisher Scientific, PA, USA.
- Cell Titer Glo (G7572) from Promega, WI, USA.

Method

Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Results

Figure 3V:
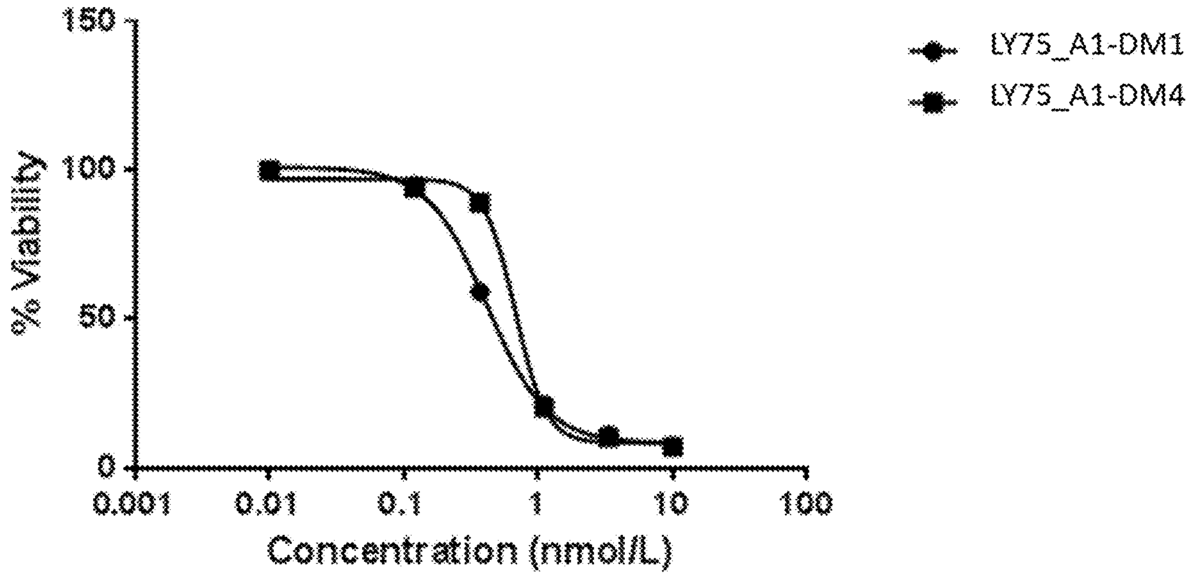
FIG. 3*v* depicts cytotoxic activity of anti-LY75 antibodies conjugated to either DM1 or DM4 in MOLP-8 cells.
Figure 3W:
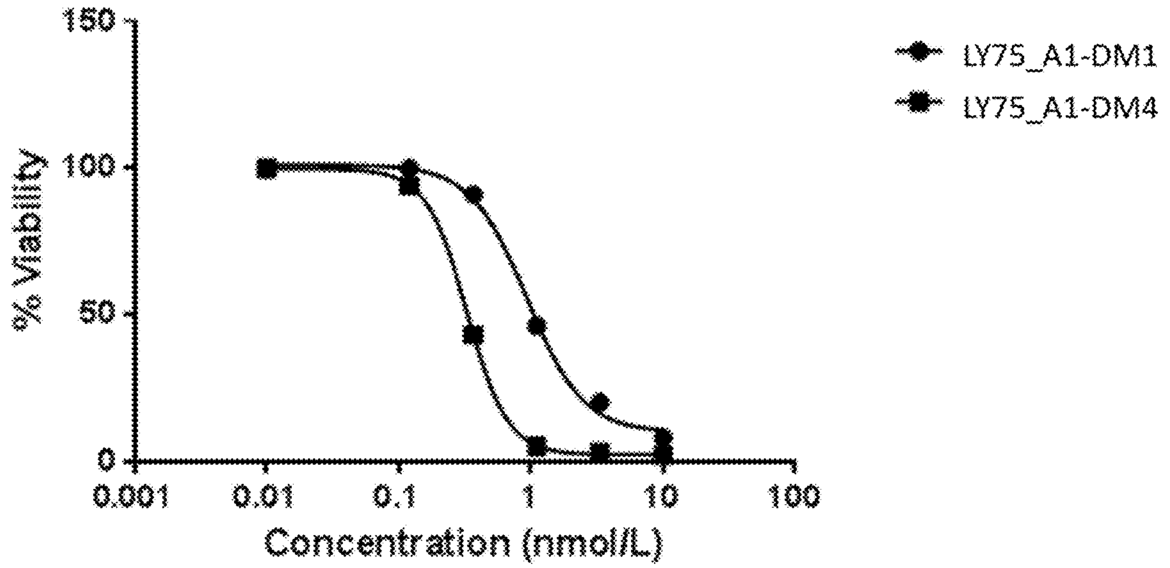
FIG. 3*w* depicts cytotoxic activity of anti-LY75 antibodies conjugated to either DM1 or DM4 in RPMI8226 cells.

FIG. 3*v* shows the cytotoxic activity of anti-LY75 antibodies conjugated to DM1 and DM4 towards MOLP-8 cells. FIG. 3*w* shows the cytotoxic activity of anti-LY75 antibodies conjugated to DM1 and DM4 towards RPMI8226 cells. These results demonstrate an increase in cytotoxic activity proportional to antibody concentration.

Example 16: Efficacy of DM1-Conjugated and DM4-Conjugated Anti-LY75 Monoclonal Antibodies in Raji Xenograft Models The efficacy of LY75_DM1 and LY75_DM4 were tested in subcutaneous Raji Burkitt's lymphoma SCID mouse xenograft model.

Immunodeficient SCID mice were inoculated subcutaneously with Raji (human Burkitt's lymphoma) tumour cells. Tumours were allowed to establish and mice were sorted into five treatment groups of 3-6 mice per group. When the mean tumour volume reached an average size of 129-132 mm3 per group, each group was treated with one of the following compounds, administered intravenously at the indicated dosages: Group 1 (Vehicle; phosphate buffered saline (PBS)); Group 2 (LY75_DM1; 10 mg/kg), Group 3 (Isotype control-DM1; 10 mg/kg), Group 4 (LY75_DM4; 5 mg/kg), Group 5 (isotype control-SPBDDM4; 5 mg/kg). A second dose was administered one week later. Body weights (BW) were monitored, the mice were examined frequently for health and adverse side effects, and tumours were measured twice weekly. Mice were euthanized when their tumours reached the tumour volume endpoint of 2000 mm3 or after 60 days, whichever came first. Efficacy was determined from tumour growth delay (TGD), the increase in median time-to-endpoint (TTE) and from logrank analysis of differences in Kaplan Meier survival curves in ADC-treated versus PBS-treat mice. The first five vehicle-treated control mice to reach endpoint were sampled for tumours that were processed by formalin fixation and paraffin embedded.

Results

Figure 4A:
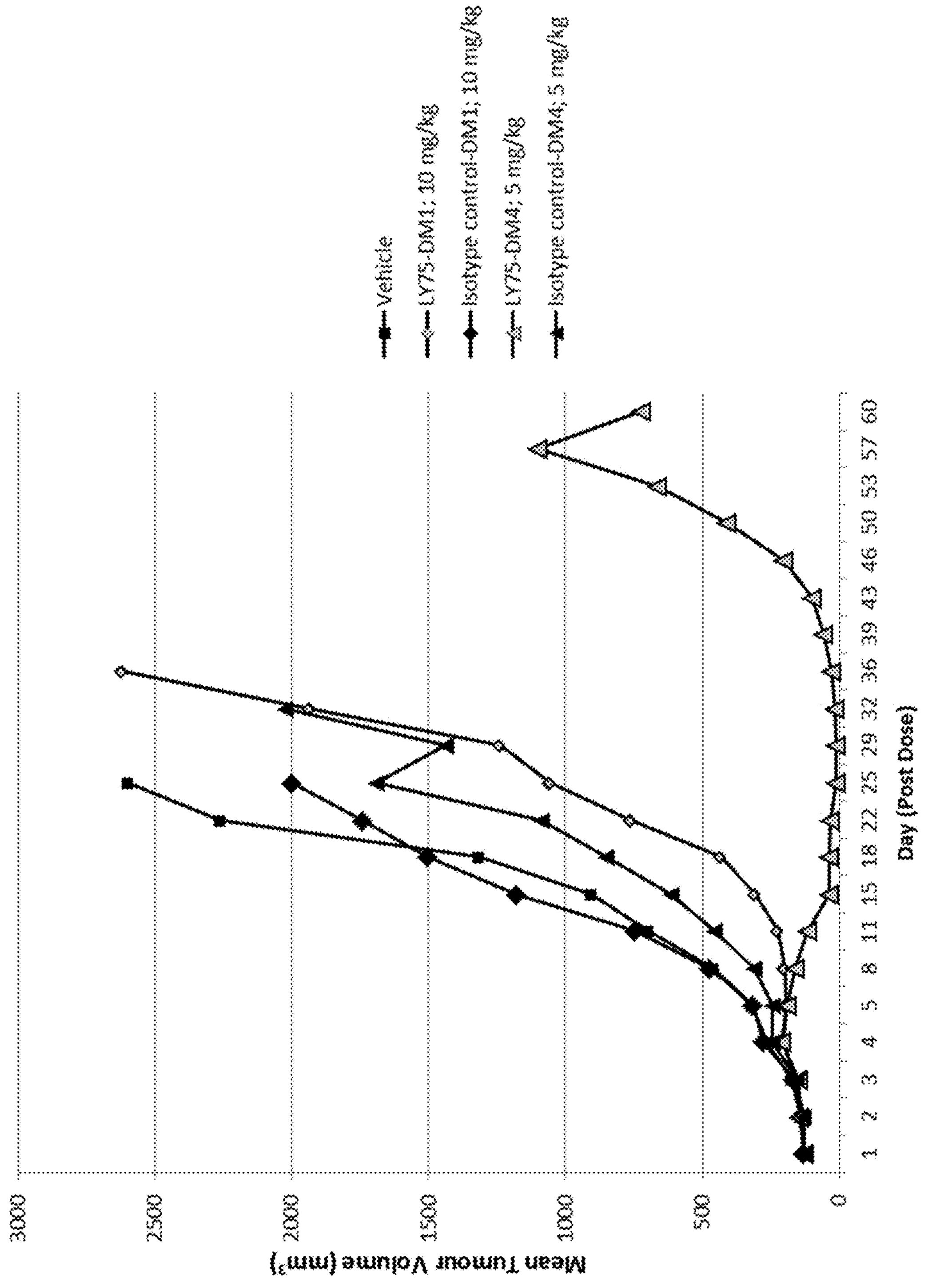
FIG. 4*a* depicts the efficacy of anti-LY75 antibodies conjugated to either DM1 or DM4 in Raji Burkitt's lymphoma SCID mouse xenograft model.

FIG. 4*a* shows LY75_DM1 and LY75_DM4 each demonstrated significant anti-tumour activity and significantly extended survival in the Raji Burkitt's lymphoma SCID mouse xenograft model compared to controls; however, the 5 mg/kg LY75_DM4 doses were significantly more effective than the 10 mg/kg doses of LY75_DM1, resulting in 5 of 6 mice with complete but transient tumour regression. All treatments were well-tolerated and no clinical signs of toxicity were observed. These data suggest the potential for ADCs directed towards LY75, for example LY75_DM1 and LY75_DM4, to provide clinical benefit in the treatment of human non-Hodgkin lymphoma cancer patients.

Example 17: Efficacy of DM1-Conjugated and DM4-Conjugated Anti-LY75 Monoclonal Antibodies in Namalwa Xenograft Models The efficacy of LY75_DM1 and LY75_DM4 were tested in subcutaneous Namalwa Burkitt's lymphoma SCID mouse xenograft model.

Immunodeficient SCID mice were inoculated subcutaneously with Namalwa (human Burkitt's lymphoma) tumour cells. Tumours were allowed to establish and mice were sorted into five treatment groups of 6 mice per group. When the mean tumour volume reached an average size of 114 mm3 per group, each group was treated with one of the following compounds, administered intravenously at the indicated dosages: Group 1 (Vehicle; phosphate buffered saline (PBS)); Group 2 (LY75_DM1; 10 mg/kg), Group 3 (Isotype control-DM1; 10 mg/kg), Group 4 (LY75_DM4; 5 mg/kg), Group 5 (isotype control-SPBDDM4; 5 mg/kg). Body weights (BW) were monitored, the mice were examined frequently for health and adverse side effects, and tumours were measured twice weekly. Mice were euthanized when their tumours reached the tumour volume endpoint of 2000 mm3 or after 60 days, whichever came first. Efficacy was determined from tumour growth delay (TGD), the increase in median time-to-endpoint (TTE), and from log rank analysis of differences in Kaplan Meier survival curves in ADC-treated versus PBS-treated mice. The first five vehicle-treated control mice to reach endpoint were sampled for tumours that were processed by formalin fixation and paraffin embedded.

Results

Figure 4B:
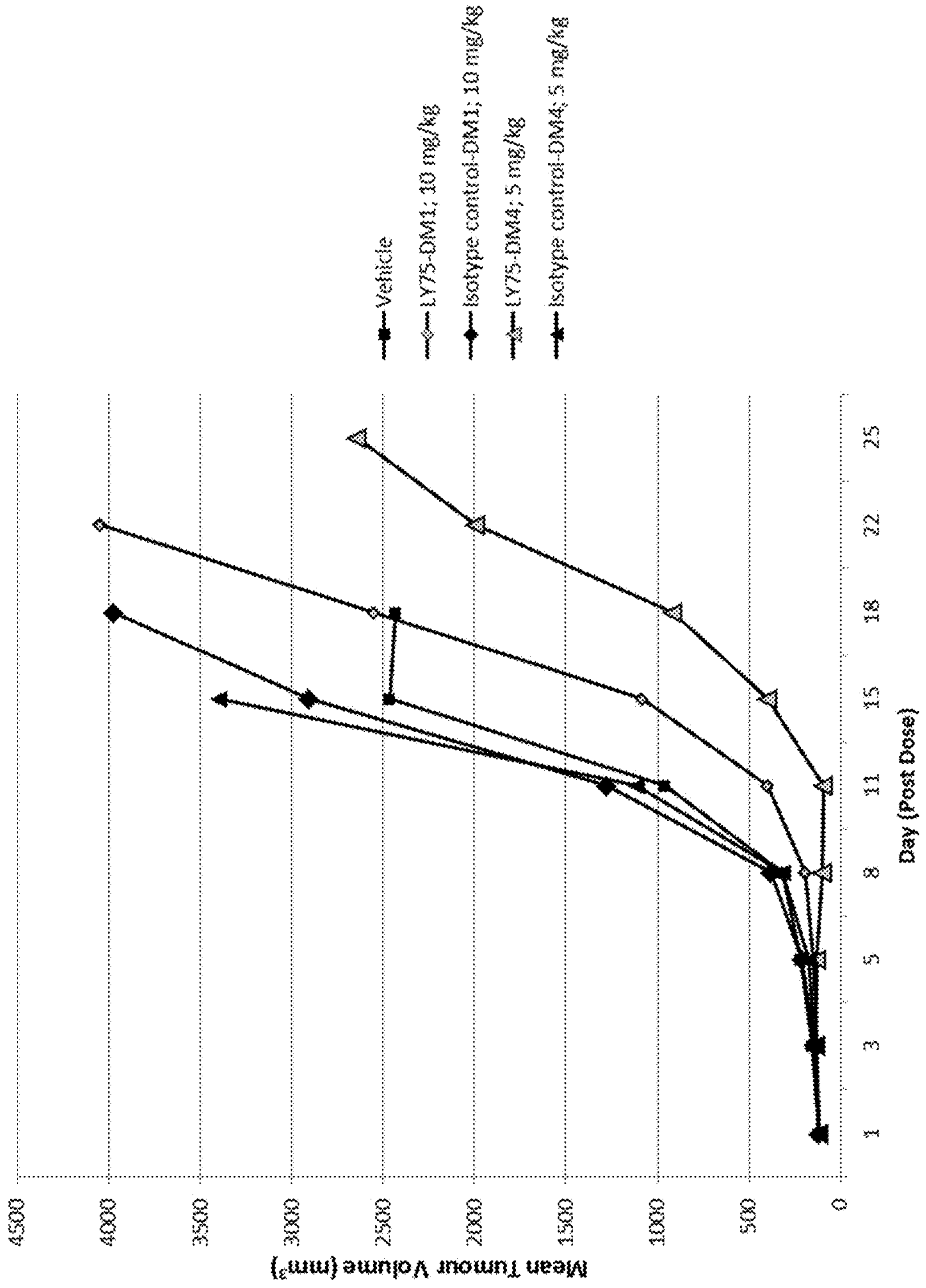
FIG. 4*b* depicts the efficacy of anti-LY75 antibodies conjugated to either DM1 or DM4 in Namalwa Burkitt's lymphoma SCID mouse xenograft model.

FIG. 4*b* shows LY75_DM1 and LY75_DM4 each demonstrated significant anti-tumour activity and survival extension in the Namalwa Burkitt's lymphoma SCID mouse xenograft model compared to controls; however, the 5 mg/kg LY75_DM4 dose was significantly more effective than the 10 mg/kg dose of LY75_DM1, causing a brief reduction in tumour volume. All treatments were well-tolerated and no clinical signs of toxicity were observed. These data suggest the potential for ADCs directed towards LY75, for example LY75_DM1 and LY75_DM4, to provide clinical benefit in the treatment of human non-Hodgkin lymphoma cancer patients.

Example 18: Efficacy of DM1-Conjugated and DM4-Conjugated Anti-LY75 Monoclonal Antibodies in Pancreatic Cancer Xenograft Models The efficacy of LY75_DM1 and LY75_DM4 were tested in the subcutaneous HPAFII pancreatic adenocarcinoma athymic nude mousexenograft model.

Immunodeficient athymic nude mice were inoculated subcutaneously with HPAFII (human pancreatic adenocarcinoma) tumor cells. Tumors were allowed to establish and mice were sorted into five treatment groups of 6 mice per group. When the mean tumor volume reached an average size of ~114 mm3/group, each group was treated with one of the following compounds, administered intravenously at the indicated dosages: Group 1 (Vehicle; phosphate buffered saline (PBS)); Group 2 (LY75_DM1; 10 mg/kg), Group 3 (Isotype control-DM1; 10 mg/kg), Group 4 (LY75_DM4; 5 mg/kg), Group 5 (isotype control-SPBDDM4; 5 mg/kg). Body weights (BW) were monitored, the mice were examined frequently for health and adverse side effects, and tumors were measured thrice weekly. Mice were euthanized when their tumors reached the tumor volume endpoint of 2000 mm3 or after 90 days, whichever came first. Efficacy was determined from the effect of treatment on tumor volume and from log rank analysis of differences in Kaplan-Meier survival curves in ADC-treated or PBS-treated mice. The tumors were sampled from vehicle-treated control mice and processed by formalin fixation and paraffin embedded.

Results

Figure 4C:
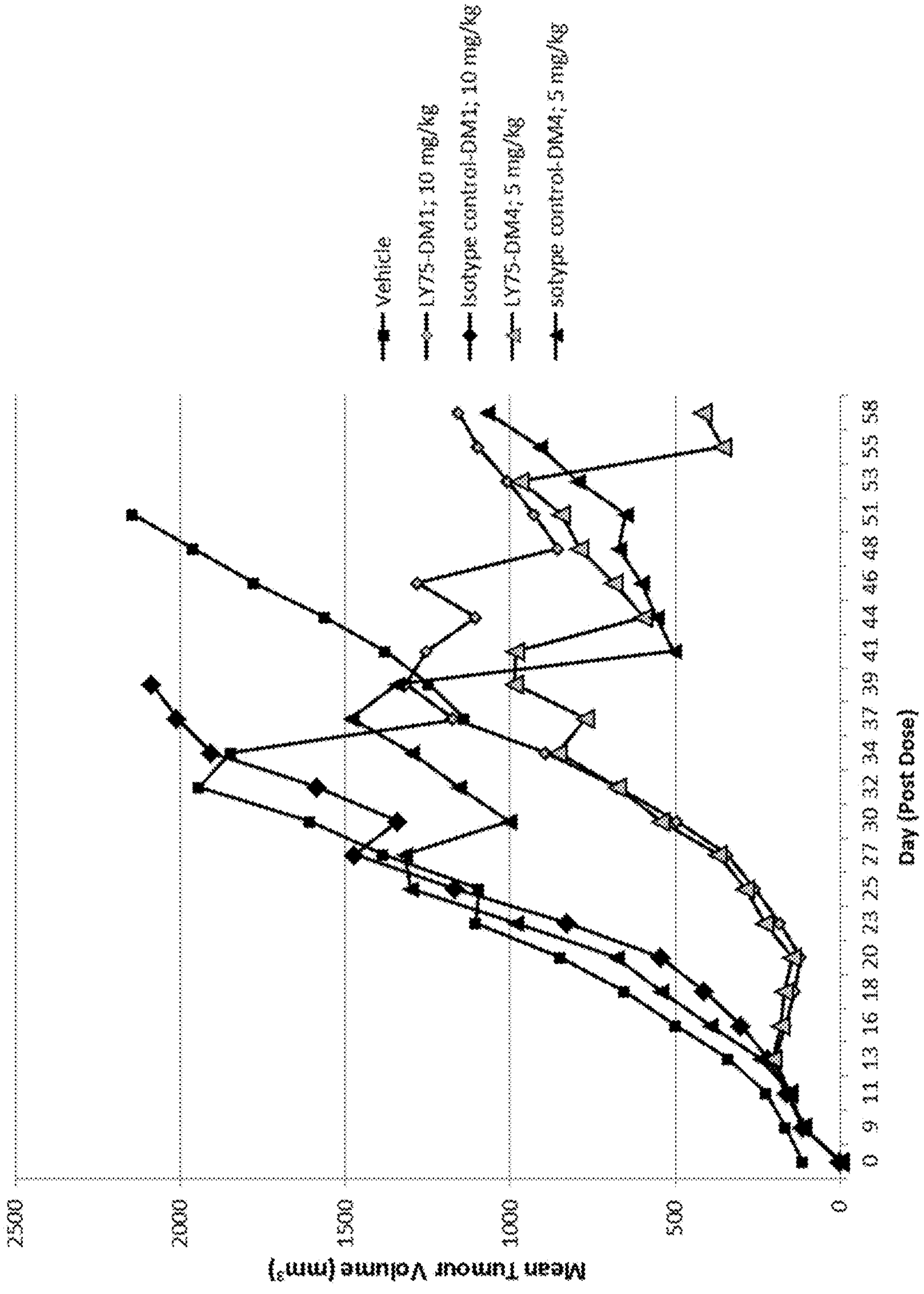
FIG. 4*c* depicts the efficacy of anti-LY75 antibodies conjugated to either DM1 or DM4 in HPAFII pancreatic adenocarcinoma athymic nude mousexenograft model.

FIG. 4*c* shows LY75_DM1 and LY75_DM4 displayed significant and similarly potent anti-tumor activity and survival extension in the HPAFII nude mouse xenograft model compared to controls. All treatments were well-tolerated and no clinical signs of toxicity were observed. These data suggest the potential for ADCs directed towards LY75, for example LY75_DM1 and LY75_DM4, to provide clinical benefit in the treatment of human pancreatic cancer patients.

Example 19: Efficacy of DM1-Conjugated and DM4-Conjugated Anti-LY75 Monoclonal Antibodies in Bladder Cancer Xenograft Models The efficacy of LY75_DM1 and LY75_DM4 were tested in the subcutaneous SW780 human bladder carcinoma SCID mouse xenograft model.

Immunodeficient athymic nude mice were inoculated subcutaneously with HPAFII (human pancreatic adenocarcinoma) tumor cells. Tumors were allowed to establish and mice were sorted into five treatment groups of 6 mice per group. When the mean tumor volume reached an average size of ~114 mm3/group, each group was treated with one of the following compounds, administered intravenously at the indicated dosages: Group 1 (Vehicle; phosphate buffered saline (PBS)); Group 2 (LY75_DM1; 1 mg/kg), Group 3 (LY75_DM1; 2.5 mg/kg), Group 4 (LY75_DM1; 5 mg/kg), Group 5 (LY75_DM4; 1 mg/kg)), Group 6 (LY75_DM4; 2.5 mg/kg)), Group 7 (LY75_DM4; 5 mg/kg)), Group 8 (isotype control-SPBDDM4; 5 mg/kg). Body weights (BW) were monitored, the mice were examined frequently for health and adverse side effects, and tumors were measured thrice weekly. Mice were euthanized when their tumors reached the tumor volume endpoint of 2000 mm3 or after 90 days, whichever came first. Efficacy was determined from the effect of treatment on tumor volume and from log rank analysis of differences in Kaplan-Meier survival curves in ADC-treated or PBS-treated mice. The tumors were sampled from vehicle-treated control mice and processed by formalin fixation and paraffin embedded.

Results

Figure 4D:
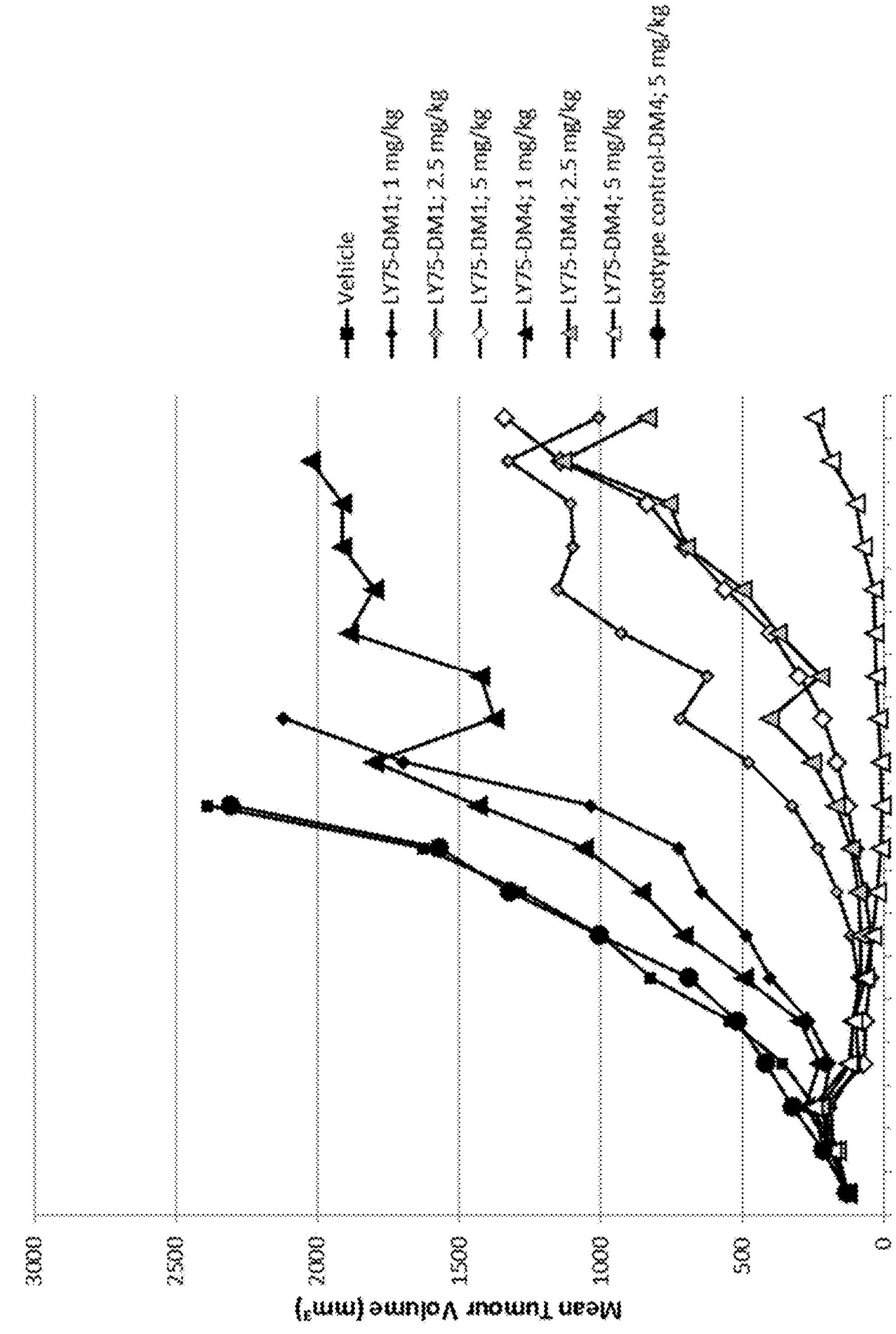
FIG. 4*d* depicts the efficacy of anti-LY75 antibodies conjugated to either DM1 or DM4 in SW780 human bladder carcinoma SCID mouse xenograft model.

FIG. 4*d* shows LY75_DM1 and LY75_DM4 displayed significant and similarly potent anti-tumor activity and survival extension in the SW780 nude mouse xenograft model compared to controls. All treatments were well-tolerated and no clinical signs of toxicity were observed. These data suggest the potential for ADCs directed towards LY75, for example LY75_DM1 and LY75_DM4, to provide clinical benefit in the treatment of human bladder cancer patients.

Example 20: Efficacy of DM1-Conjugated and DM4-Conjugated Anti-LY75 Monoclonal Antibodies in Breast Cancer Xenograft Models The efficacy of LY75_DM1 and LY75_DM4 were tested in the subcutaneous MDA-MB-468 athymic nude mouse xenograft model.

Immunodeficient athymic nude mice were inoculated subcutaneously with MDA-MB-468 (human triple negative breast adenocarcinoma) tumour cells. Tumours were allowed to establish and mice were sorted into seven treatment groups of 10 mice per group. When the mean tumour volume reached an average size of 167 mm3 per group, each group was treated with one of the following compounds, administered intravenously at the indicated dosages: Group 1 (Vehicle; 20 mM sodium succinate, pH 5.0, 6% trehalose, 0.04% polysorbate); Group 2 (LY75_DM1; 5 mg/kg), Group 3 (LY75_DM1; 10 mg/kg), Group 4 (LY75_DM4; 5 mg/kg), Group 5 (LY75_DM4; 2.5 mg/kg), Group 6 (LY75_DM4; 1 mg/kg), Group 7 (Isotype control-DM4; 5 mg/kg). Body weights (BW) were monitored, the mice were examined frequently for health and adverse side effects, and tumours were measured twice weekly. Mice were euthanized 82 days after tumour inoculation. Efficacy was determined from anti-tumour activity (mean tumour size in treatment group/mean tumour size in control group×100) and the increase in mean time-to-endpoint (TTE) in ADC-treated versus PBS-treated mice. The five largest tumours in vehicle-treated control mice on day 71 post inoculation were sampled processed by formalin fixation and paraffin embedded.

Results

Figure 4E:
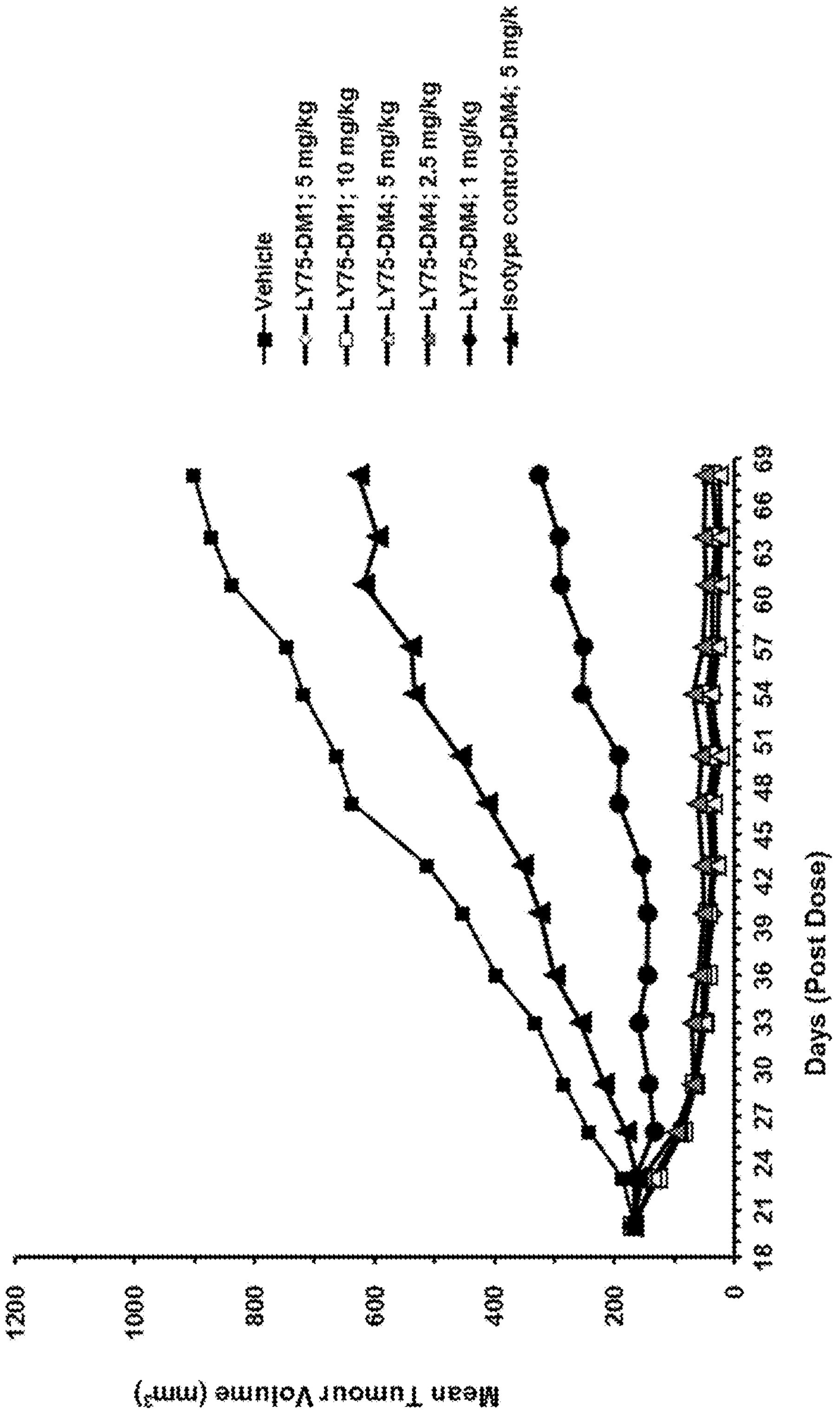
FIG. 4*e* depicts the efficacy of anti-LY75 antibodies conjugated to either DM1 or DM4 in MDA-MB-468 athymic nude mouse xenograft model.

FIG. 4*e* shows LY75_DM1 and LY75_DM4 each demonstrated dramatic anti-tumour activity in the MDA-MB-468 nude mouse xenograft model compared to controls. Dose dependent activity was observed with LY75_DM4, where 2.5 and 5 mg/kg were much more potent than 1 mg/kg. At 5 mg/kg, LY75_DM1 and LY75_DM4 were similarly effective. Sustained regressions in mean tumour volume were observed for LY75_DM1 at 10 and 5 mg/kg and LY75_DM4 at 5 and 2.5 mg/kg. All treatments were well-tolerated and no clinical signs of toxicity were observed. These data suggest the potential for ADCs directed towards LY75, for example LY75_DM1 and LY75_DM4, to provide clinical benefit in the treatment of human triple negative breast cancer patients.

Example 21: Efficacy of DM1-Conjugated and DM4-Conjugated Anti-LY75 Monoclonal Antibodies in Colorectal Cancer Xenograft Models The efficacy of LY75_DM1 and LY75_DM4 were tested in the subcutaneous COLO205 colorectal adenocarcinoma athymic nude mouse xenograft model.

Immunodeficient athymic nude mice were inoculated subcutaneously with COLO205 (human colorectal adenocarcinoma) tumor cells. Tumors were allowed to establish and mice were sorted into five treatment groups of 6 mice per group. When the mean tumor volume reached an average size of 117 mm3 per group, each group was treated with one of the following compounds, administered intravenously at the indicated dosages: Group 1 (Vehicle; phosphate buffered saline (PBS)); Group 2 LY75_DM1; 10 mg/kg), Group 3 (Isotype control-DM1; 10 mg/kg), Group 4 (LY75_DM4; 5 mg/kg), Group 5 (Isotype control-DM4; 5 mg/kg). A second dose was administered twelve days after the first. Body weights (BW) were monitored, the mice were examined frequently for health and adverse side effects, and tumors were measured twice weekly. Mice were euthanized when their tumors reached the tumor volume endpoint of 1000 $mm^3$ or after 60 days, whichever came first. Efficacy was determined from tumor growth delay (TGD), the increase in median time-to-endpoint (TTE) and from log rank analysis of differences in Kaplan Meier survival curves in ADC-treated versus PBS-treated mice. The first five vehicle-treated control mice to reach endpoint were sampled for tumors that were processed by formalin fixation and paraffin embedded.

Results

Figure 4F:
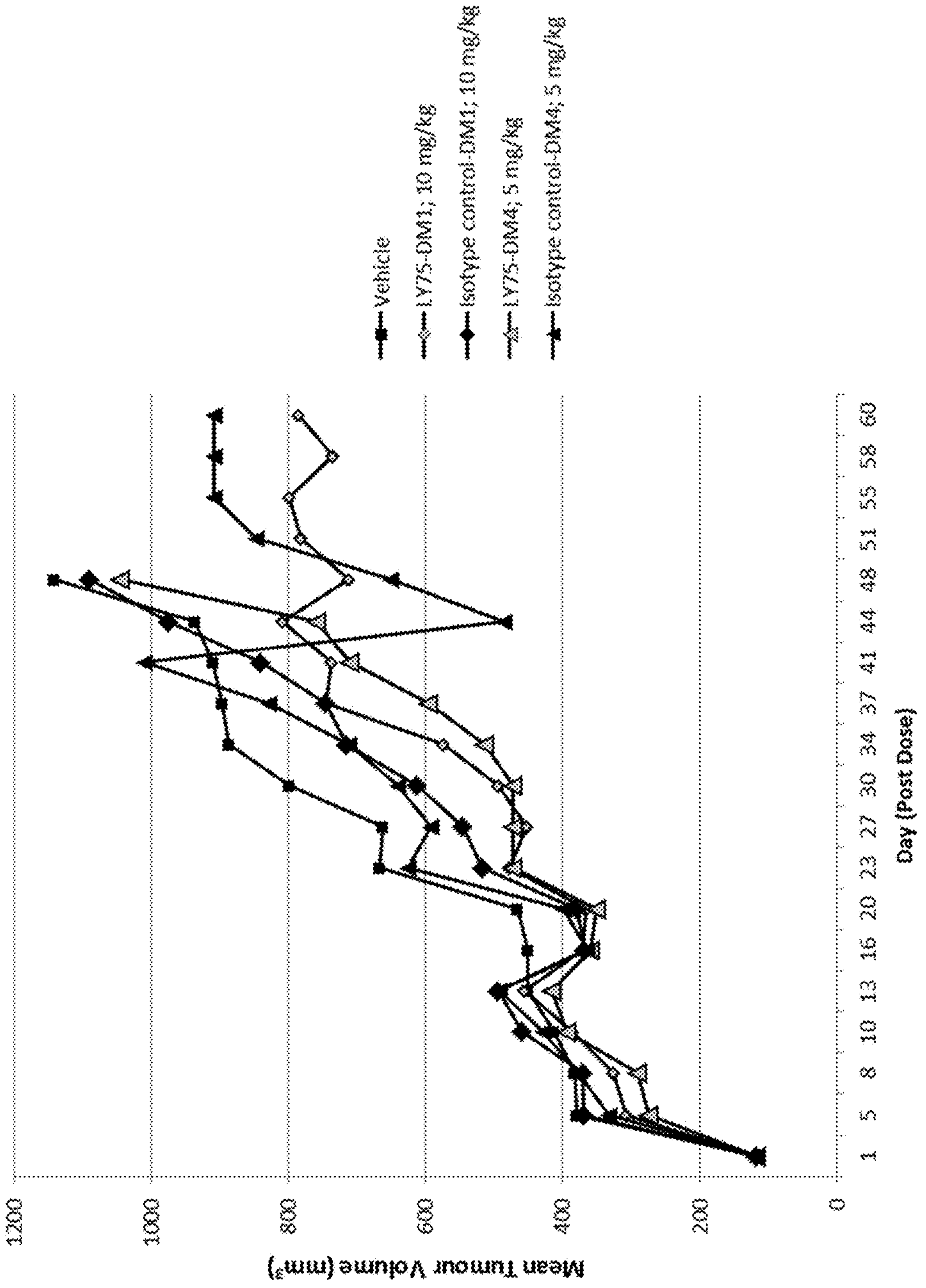
FIG. 4*f* depicts the efficacy of anti-LY75 antibodies conjugated to either DM1 or DM4 in COLO205 colorectal adenocarcinoma athymic nude mouse xenograft model.

FIG. 4*f* shows LY75_DM1 and LY75_DM4 exhibited similar modest anti-tumor activity and survival extension in the COLO205 colorectal adenocarcinoma nude mouse xenograft model compared to controls. All treatments were well-tolerated and no clinical signs of toxicity were observed. These data suggest the potential for ADCs directed towards LY75, for example LY75_DM1 and LY75_DM4, to provide clinical benefit in the treatment of human colorectal cancer patients.

Example 22: Toxicity of DM1-Conjugated and DM4-Conjugated Anti-LY75 Monoclonal Antibodies in Cynomolgus Monkeys Six male monkeys were assigned to the study with 2 monkeys/group. Either vehicle (PBS), LY75_DM4 (cleavable) or LY75_DM1 (non-cleavable) was administered twice (on Day 1 and Day 29) by a 15-minute intravenous infusion at 0 mg/kg/dose (PBS, vehicle), 5 mg/kg/dose (LY75_DM4, cleavable) or 10 mg/kg/dose (LY75_DM1, non-cleavable). Blood samples were collected for toxicokinetic evaluations prior to dose initiation (Day 1), and 1, 2, 3, 7, 14, 21 and 28 days post each dose. Blood samples for clinical pathology analyses were collected prior to dose initiation (Day 1), and 1, 3, 7, 14, 21 and 28 days post each dose (28 days post the 1st dose was also served as the pre-dose time point for the 2nd dose). All study animals were euthanized and necropsied following the final blood collection on Day 57. The plasma separated from each blood draw was isolated, frozen and shipped to Oxford BioTherapeutics, Inc. to be analyzed for ADC concentration by ELISA.

Treatment-related clinical pathology findings included a mild regenerative anemia and transient decreases in the blood leukocyte profile most notably in neutrophils counts. Anemia was observed in both animals treated with 5 mg/kg LY75_DM4 and in one of the two animals treated with 10 mg/kg LY75_DM1. Severe neutropenia with a nadir at one-week post dose and a rapid recovery in counts was observed in all animals; the nadir in absolute neutrophil count was lower in LY75_DM4 treated animals. There were no test article-related effects on the APTT and PT coagulation parameters. Serum chemistry changes included transient increases in AST, CK, LDH (in 1 of 2 animals in each treatment group) and globulin following administration of 5 mg/kg LY75_DM4 and 10 mg/kg LY75_DM1. In addition, a transient increase in the liver specific enzyme ALT was observed only in the LY75_DM4 treated animals. The short duration of and/or the magnitude of the increases in serum chemistry parameters suggest they were not adverse. There were no test-article related urinalysis findings. Upon examination at necropsy following a 4-week recovery period there were no treatment related gross pathology findings or changes in absolute and relative organ weights. Histopathology findings only in the thyroid gland (an alteration in the colloid morphology in follicles) and kidney (dilated tubules in the outer cortex), were graded as minimal severity; not associated with changes in other study parameters; and, not adverse and of minimal toxicological significance. Conclusion: Repeated dose treatment with two doses of 5 mg/kg LY75_DM4 or 10 mg/kg LY75_DM1 was well tolerated in cynomologus monkeys. All treatment-related toxicity findings were reversible following a 4-week recovery period.

Example 23: Epitope Characterisation of LY75 A1 by Competitive Fluorescence Activated Cell Sorting (FACS) Binding Analysis Method COLO205 cells (ATCC, catalog #CCL-222) were detached from tissue culture flasks with Cell Stripper (Cellgro, catalog #MT-25-056CI). Cells were washed and resuspended in FACS buffer (PBS+2% FBS), neutralized with growth media, and counted. Cells were plated at 50,000 cells per well in a V Bottom 96-well plate. Cells were washed once with FACS buffer (PBS (Fisher, catalog #SH30028-03)+2% FBS). An anti-LY75-mAb (Selected from Example 1) or LY75_A1 was added to wells starting at 250 nM and diluted serially 3 fold and applied to the relevant wells for 45 minutes on ice. Test wells that required single or multiple staining steps were left in FACS buffer as appropriate to ensure the final staining was completed simultaneously for all conditions tested. Two wells were left unstained in FACS buffer as controls.

After the incubation with blocking antibody, cells were washed twice in FACS buffer. The cells were resuspended in FACS buffer containing the anti-LY75-mAb conjugated to MCC-DM1 (1 nM) and incubated on ice for 45 minutes. The cells were washed as above and resuspended in FACS buffer plus 1 ug/ml mouse anti-maytansine antibody and incubated in ice for 45 minutes. The cells were washed as above and resuspended in FACS buffer containing 2 ug/ml goat anti-mouse kappa RPE. The cells were incubated on ice for 45 minutes then washed as above. The cells were resuspended in FACS buffer at 200 ul per well. Mean fluorescence intensity of each sample was determined using a Guava EasyCyte Plus HT Flow Cytometer (96 well plate formats) and the raw data was analyzed using the Guava Cytosoft.

Results

Figure 5A:
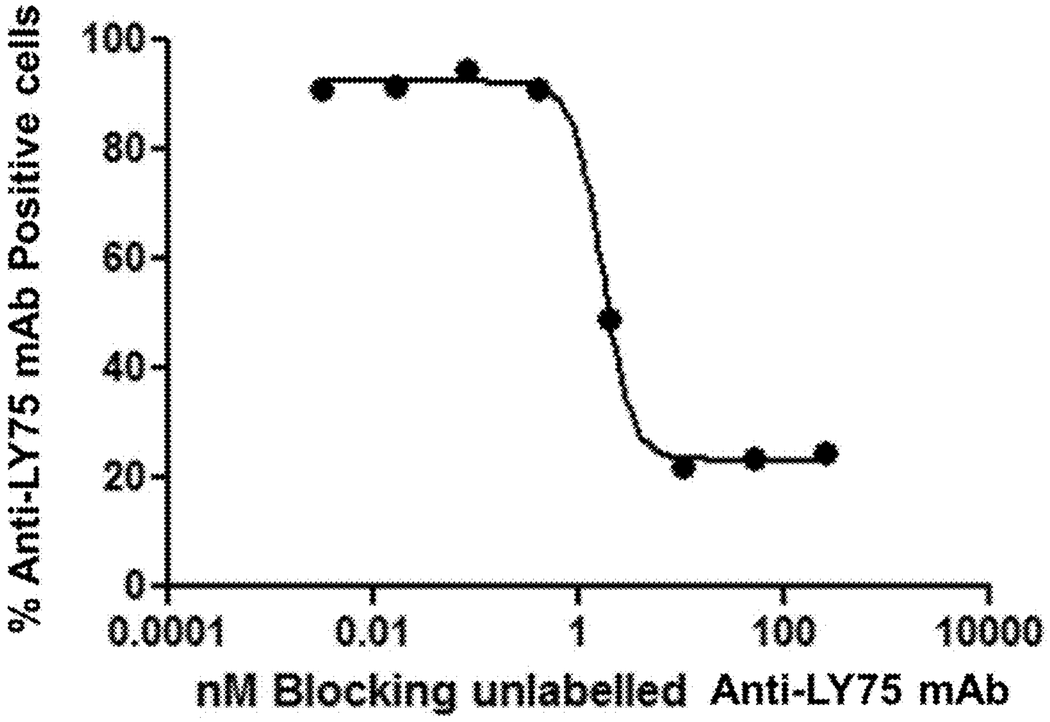
FIG. 5*a* shows competitive binding of anti-LY75-mAb and an anti-LY75-mAb conjugated to MCC-DM1.
Figure 5B:
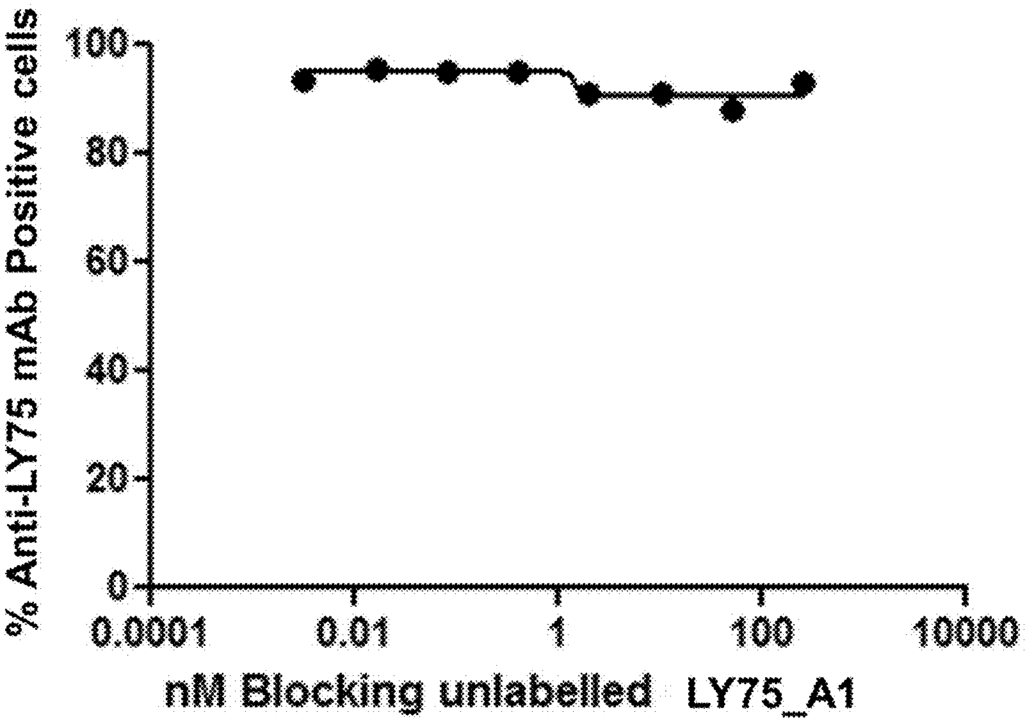
FIG. 5*b* shows non-competitive binding of LY75_A1 and an anti-LY75-mAb conjugated to MCC-DM1.
Figure 6A:
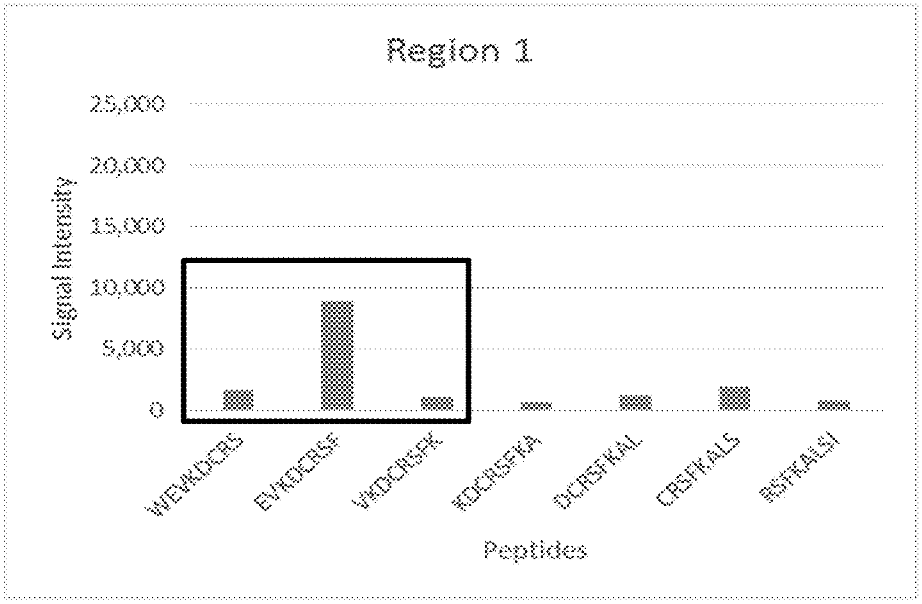
FIG. 6*a*-6*j* show graphical representations of the binding of antibody LY75_A1 to LY75 peptides on a peptide microarray. Figures disclose SEQ ID NOS 53-163, respectively, in order of appearance.
Figure 6B:
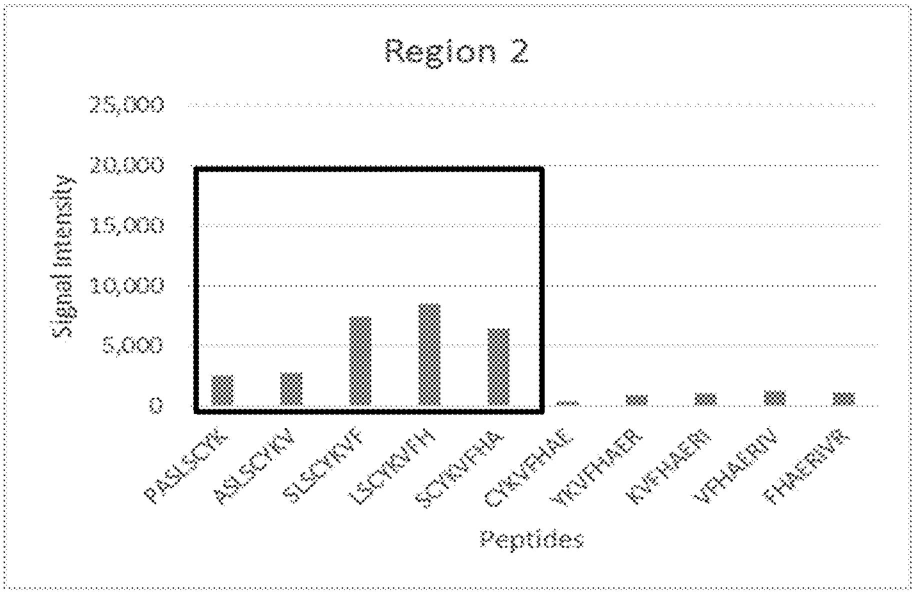
Figure 6C:
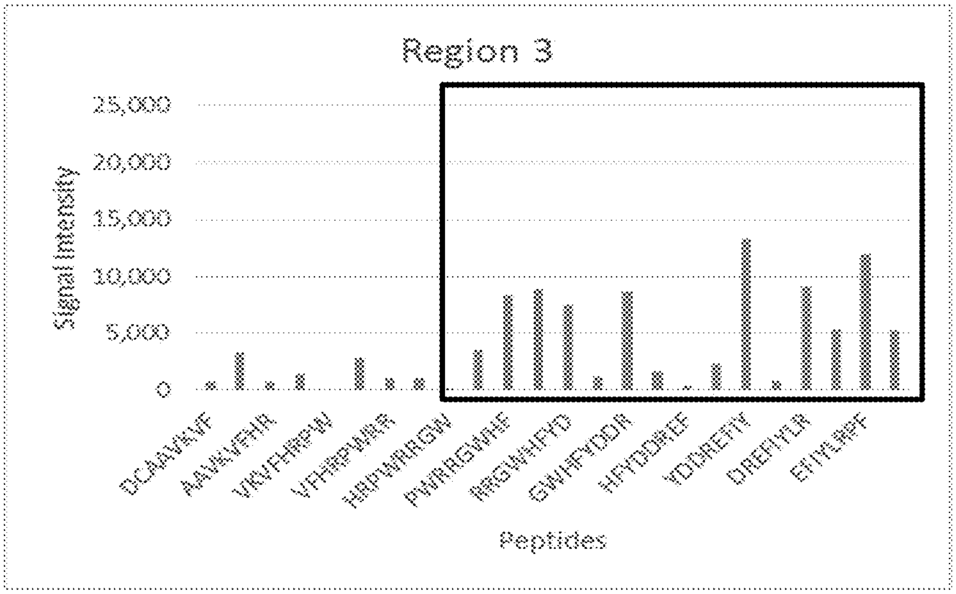
Figure 6D:
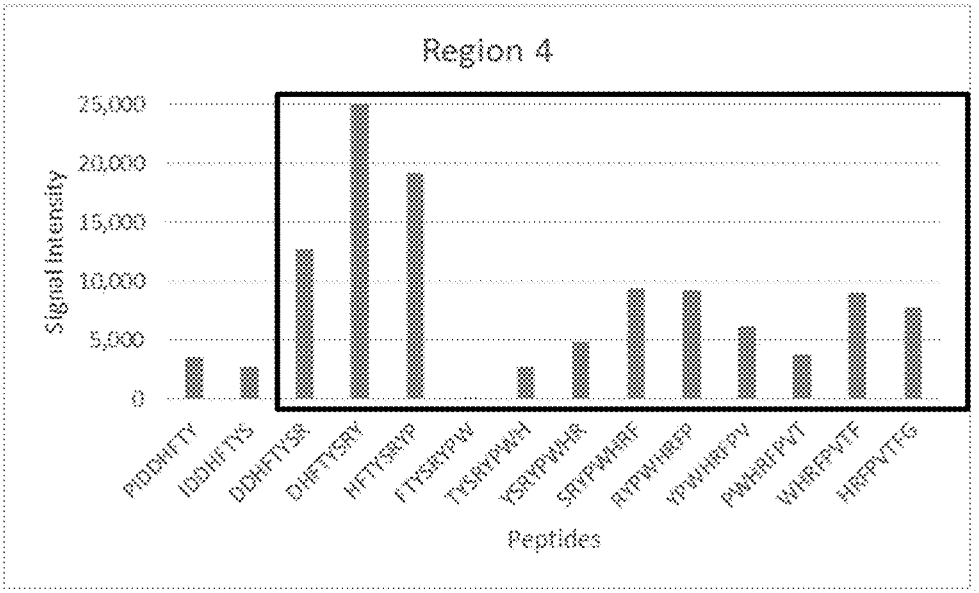
Figure 6E:
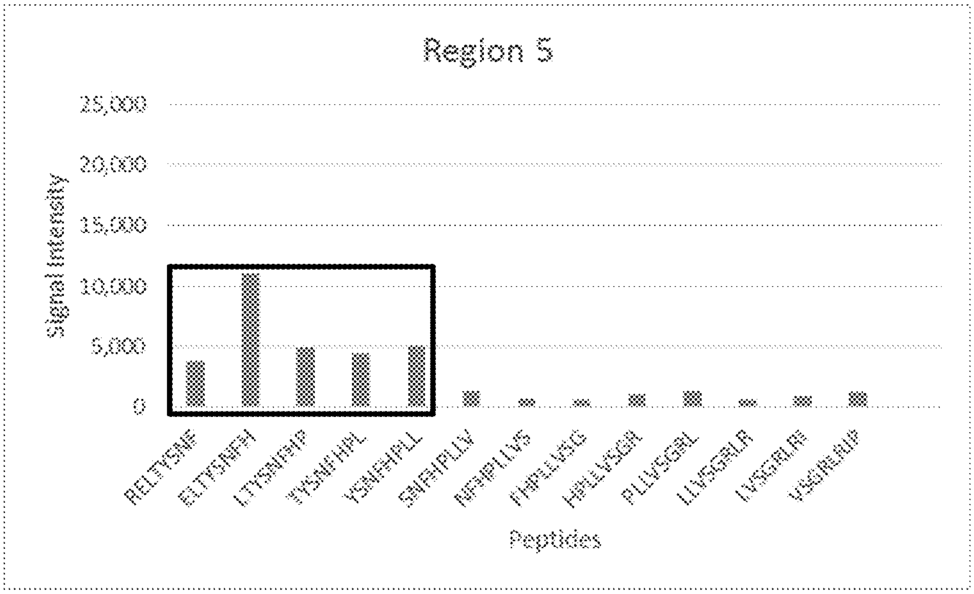
Figure 6F:
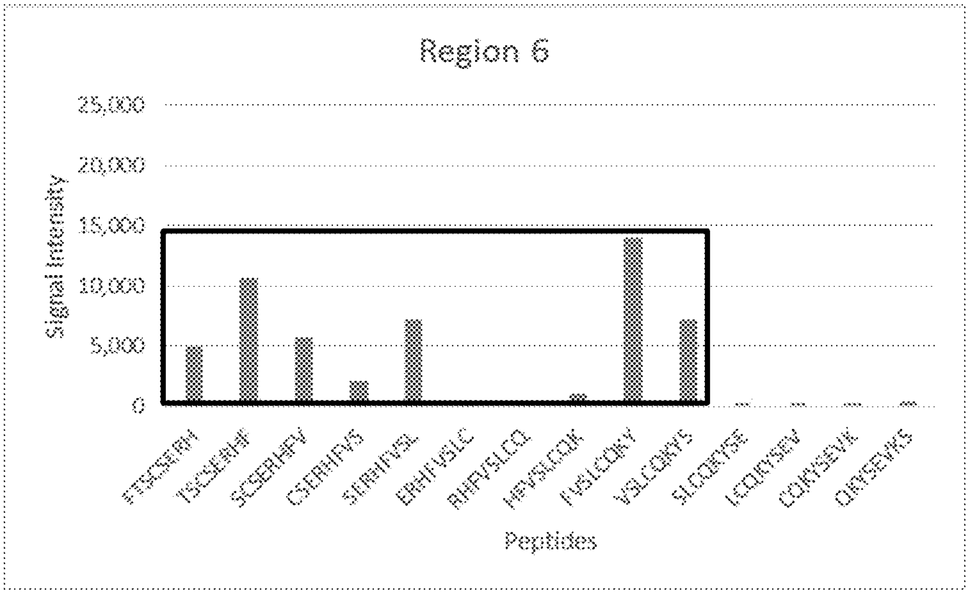
Figure 6G:
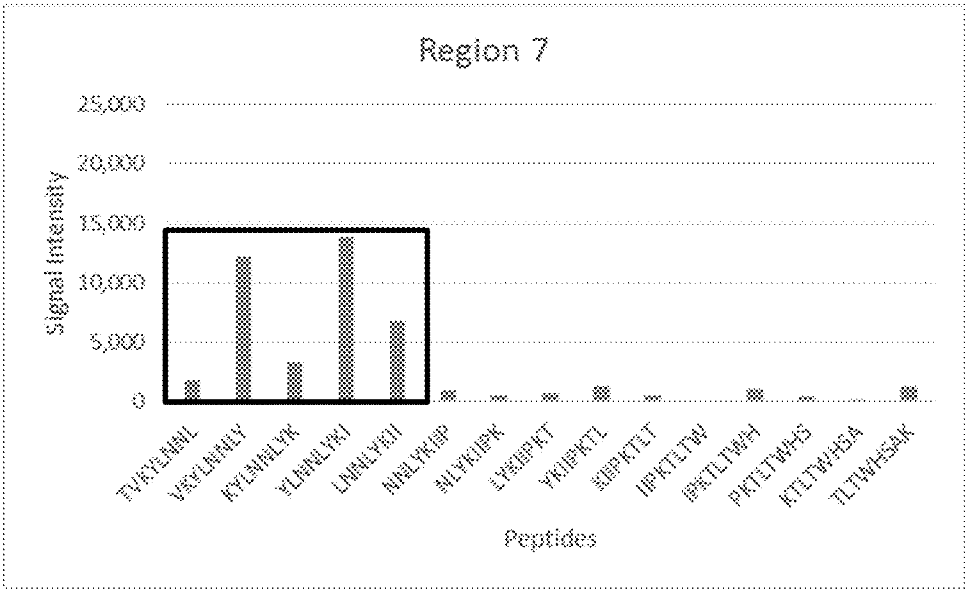
Figure 6H:
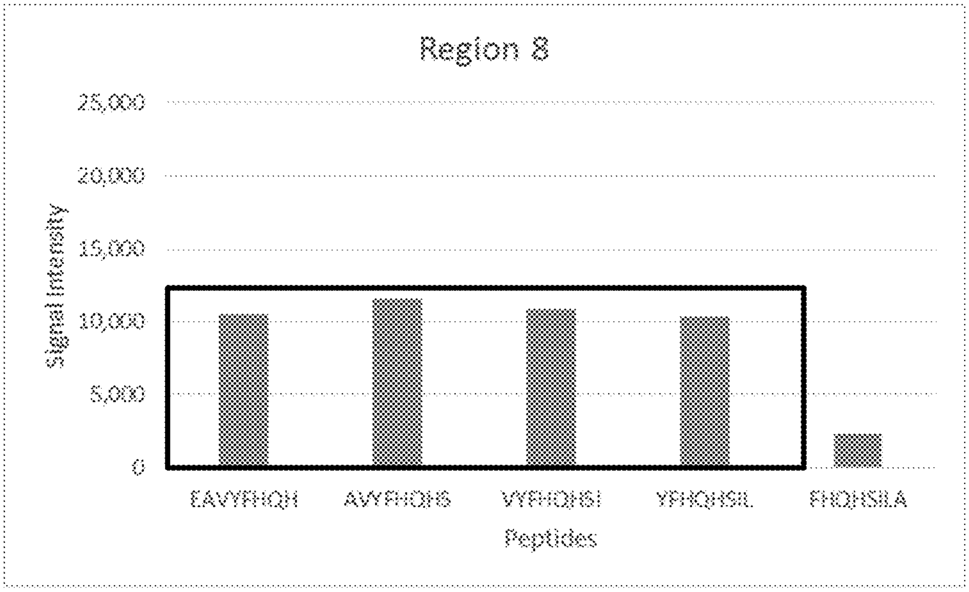
Figure 6I:
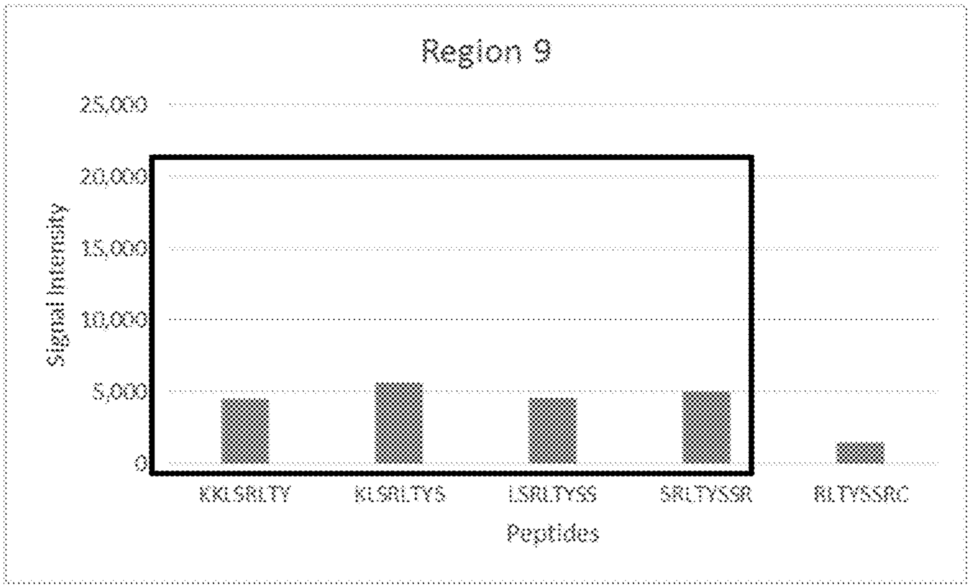
Figure 6J:
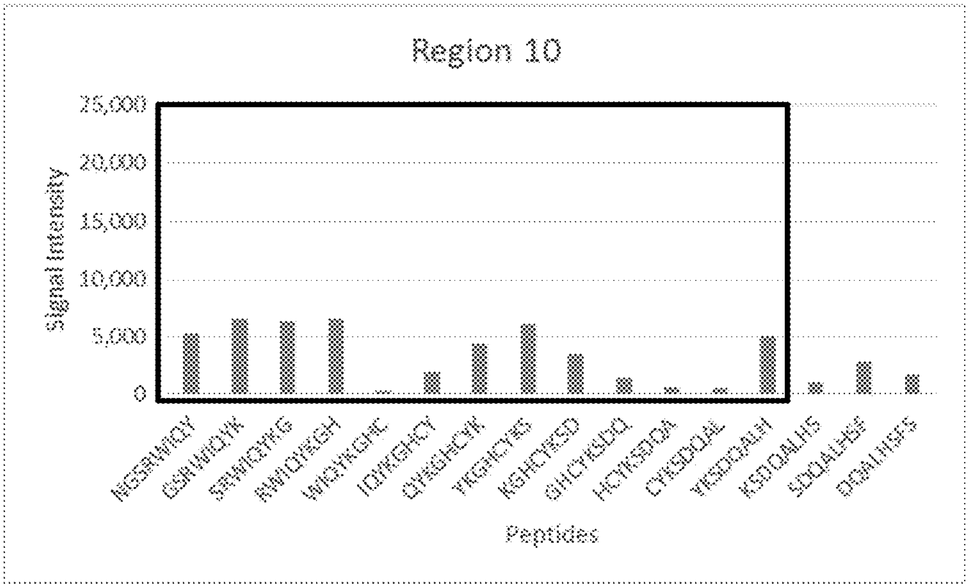

FIG. 5*a* shows blocking with the anti-LY75-mAb-MCC-DM1 reduced the binding of anti-LY75-mAb. Analysis of the binding of LY75_A1 to COLO205 cells showed that LY75_A1 is unable to block binding of anti-LY75-mAb-MCC-DM1 (see FIG. 5*b*). It can therefore be determined that the anti-LY75-mAb and LY75_A1 are non-competing antibodies and LY75_A1 recognizes a different and unique epitope of LY75 to that of other anti-LY75 antibodies.

Example 24: Epitope Characterization of LY75 A1 by Peptide Micro Array Assay Method The peptide microarray analysis was performed by LC Sciences, Houston TX, in brief the method comprised the following steps:—Contiguous 8mer peptides of LY75 protein having one amino acid overlap spanning residues 216 to 1666 of the full length LY75 protein were synthesized and immobilized on a microarray chip. The chip comprised three panels such that the experiment was performed in in triplicate. The microarray was addressed with LY75_A1 to identify the peptides to which the antibody bound. The binding assay was performed under the following conditions:—

The microarray comprising the contiguous peptides in triplicate was washed with 1 mL of binding buffer at 4° C. for 20 min. It was then incubated with 1 μg/mL LY75_A1 in binding buffer (pH 7.0) at 4° C. for 2 hrs. The array was again washed with 0.5 mL of washing buffer at 4° C. for 30 min then incubated with 25 ng/ml anti-human IgG Alexa 647 conjugate in binding buffer (pH 7.0) at 4° C. for 1 hr. The array was again washed with 0.5 mL of washing buffer at 4° C. for 30 min.

The array was then Scanned at 635 nm and PMT 500 and the signal Intensity was recorded. The peptide was classed as detectable if it was present in at least ⅔ legal duplicates. The average signal intensity of the replicates was reported as the final signal intensity.

Results

As can be seen from FIG. 6 antibody LY75_A1 showed specific binding to a number of peptides located on the array. The maximum signal seen for LY75_A1 binding was 25000 (scale 1-65535), with the average signal for all spots on the array being about 885. A signal intensity of 3000 was set as the background cut off point for non-specific binding. Based on the level of antibody binding signal intensity seen potential sequences forming the epitope for LY75_A1 were identified. These regions are shown in FIGS. 6*a*-6*j* and as SEQ ID NOs: 22-31.

Example 25: LY75 A1 Peptide Pull Down Assay

Method 1.1 Pull Down Assay

Recombinant LY75 protein was digested by on-bead tryptic proteolysis (Promega, US). The resulting digest peptides were recovered using a C18 capture column (Thermo Fisher Scientific). Purified peptides were then incubated with 200 μl of protein A beads cross-linked with LY75A1 antibody overnight at 4° C. Next day the unbound peptides were collected and the beads were washed with 1 ml of PBS twice. The antibody bound peptides were eluted from beads by heating them at 90° C. in 100 μl of PBS for 5 minutes. This elution step was repeated.

1.2 Mass Spectrometry

Samples were analysed by liquid chromatography-mass spectrometry using a Waters nanoACQUITY UPLC System fitted with a nanoACQUITY UPLC BEH 130 C18 column, 75 μm×250 mm (186003545) and a LTQ Orbitrap Velos (Thermo Fisher Scientific). Peptides were eluted with a 300 nl/min gradient increasing from 3% to 35% acetonitrile over 120 min. Full-scan mass spectra were acquired at 60000 resolving power between 400-2000 m/z mass range in the Orbitrap. In each cycle, the twenty most intense peptides were selected for CID MS/MS scans in the linear ion trap with nanospray ion source fitted on the instrument.

1.3 Amino Acid Sequence Analysis of Peptide

The raw data generated from the LTQ Orbitrap Velos was processed through the Mascot software (Matrix Science) which uses the Mowse algorithm (Curr Biol. 1993 Jun. 1;3(6):327-3) to infer amino acids sequences from the peak lists by searching against a sequence database consisting of Ensembl (http://www.ensembl.org/index.html), IPI (www.ebi.ac.uk/IPI/IPIhuman.html) and SwissProt (http://www.uniprot.org) along with contaminant protein sequences. Criteria for peptide identification included trypsin digestion, up to 2 missed cleavage sites and various biological and chemical modifications (oxidized methionine, cysteine modification by MMTS or iodoacetamide and phosphorylation of serine, threonine and tyrosine). Peptides ranked 1 with an expectation value of 0.05% or less, an ion score of 28 or higher were loaded into the OGAP database.

1.4 Discrimination of LY75 Associated Peptides

The process to identify LY75 used the peptide sequences obtained experimentally by mass spectrometry, as described above, of naturally occurring human proteins to identify and organize coding exons in the published human genome sequence. These experimentally determined sequences were compared with the OGAP® database which was compiled by processing and integration of peptide masses, peptide signatures, ESTs and Public Domain Genomic Sequence Data as described in International Patent Application WO2009/087462.

Results

The results of the peptide pull down assay using antibody LY75_A1 are shown in Table 1 below and in FIGS. 7A-7D. Peptides which were identified in both peptide elutions 1a and 1b in the pull down assay and in the microarray assay were considered to be the most likely candidates for forming the epitope.

TABLE 1

Comparison of peptide microarray and peptide pull down experiments

| SEQ ID NO: | Peptide Identified by Microarray Assay | Peptide Identified by Pull Down Assay |
|---|---|---|
| | Region 1 (aa609-618) | — |
| | Region 2 (aa651-662) | — |
| 46 | Region 3 (aa761-780) | GWHFYDDR (765-772) |
| 47 | Region 4 (aa883-901) | ISEWPIDDHFTYSR(877 to 890) |
| 48 | | FPVTFGEECLYMSAK(896-910) |
| 49 | Region 5 (aa1029-1040) | ELTYSNFHPLLVSGR(1030-1044) |
| 50 | Region 6 (aa1077-1093) | HFVSLCQK (1084-1091) |
| 51 | Region 7 (aa1107-1118) | QTLQNASETVK (1099-1109) |
| | Region 8 (aa1368-1378) | — |
| | Region 9 (aa1518-1528) | — |
| | Region 10 (aa1535-1554) | — |

Table 1 shows that a number of overlapping LY75 peptide regions were identified in both the Peptide Microarray assay and in both elutions 1a and 1b the Peptide pull down assay. These regions are considered to be the most likely to contain the epitope recognized by antibody LY75_A1 as they are bound by LY75_A1 tested by both techniques employed.

Example 26

A number of activated B-cells Diffuse Large B-cell Lymphoma (ABC-DLBCL) cell lines (i.e. TMD8 and HBL1 cell lines) were exposed for 72 hours to increasing doses of LY75_DM4 (i.e. 0.018-0.037-0.075-0.15-0.3-0.6-1.2 nM) either alone or in combination with increasing doses of Rituximab (2.34-4.68-9.37-18.75-37.5-75-150) or Ibrutinib (15.6-31.2-62.5-125-250-500-1000 nM). This was followed by an MTT [3-(4,5-dimethylthiazolyl-2)-2,5-diphenyltetrazoliumbromide] assay.

The Chou-Talalay combination index (CI) was estimated using the Synergy R package (Preclinical versus Clinical Drugs Combination Studies. Chou TC. Leuk. Lymphoma. 2008;49(11):2059-2080). This provides a quantitative definition for strong synergism (<0.3), synergism (0.3-0.9), additive effect (0.9-1.1) or antagonism/no benefit (>1.1).

Figure 8A:
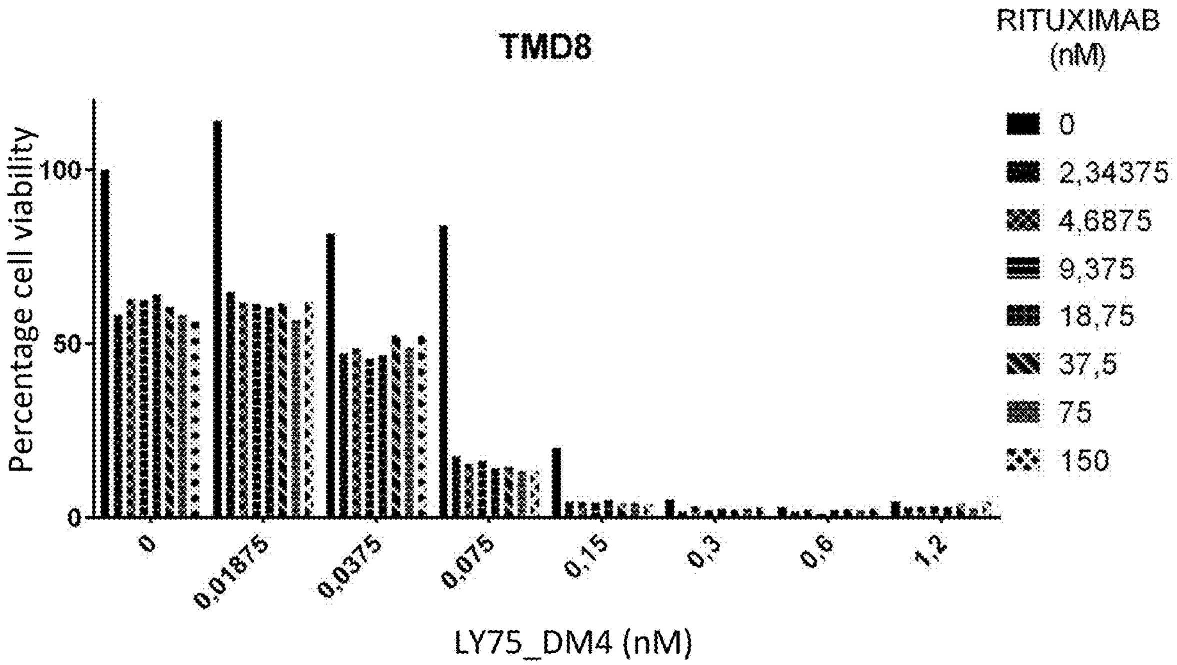
FIGS. 8A and 8B show the anti-proliferative effect of different (nM) doses of LY75_DM4 as a single treatment or in combination with Rituximab on two different ABC-DLBCL cell lines (TMD8 and HBL1). (CI=Chou-Talalay Combination Index).
Figure 8B:
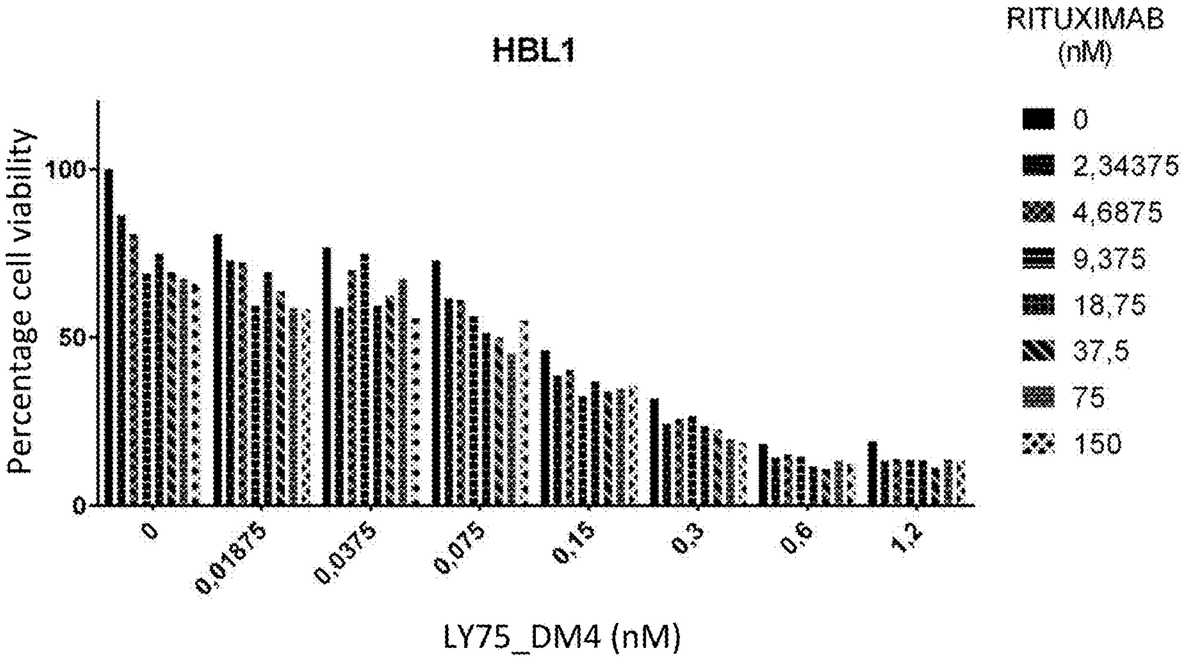
Figure 9:
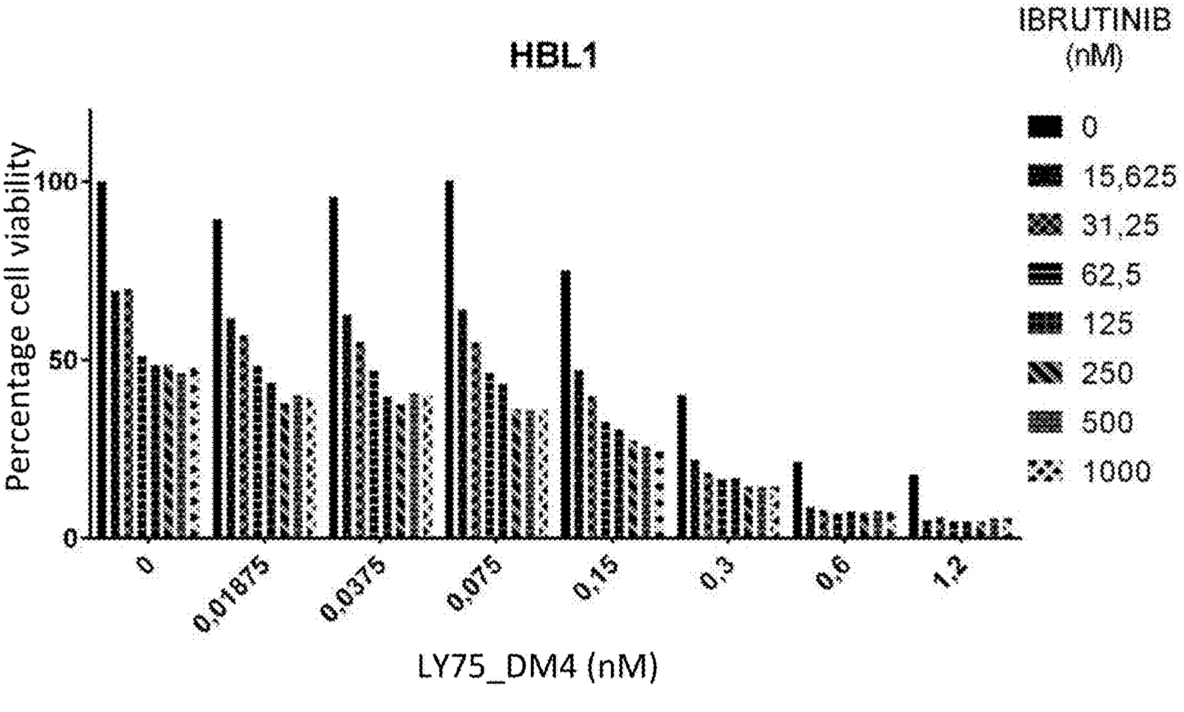
FIG. 9 shows the anti-proliferative effect of different (nM) doses of LY75_DM4 as a single treatment or in combination with Ibrutinib on HBL-1 cell lines (ABC-DLBCL). (CI=Chou-Talalay Combination Index). Median CI=0.24.

FIGS. 8A-B show the synergistic effects seen between LY75_DM4 and Rituximab. FIG. 9 shows the synergistic effects seen between LY75_DM4 and Ibrutinib. Supporting data is shown in Tables 2, 3, and 4 below.

TABLE 2

Chou-Talalay Combination Index (CI) of different doses of LY75 DM4 in combination with Rituximab on three TMD8 ABC-DLBCL cell lines.

| No | Rituximab (nM) | LY75_DM4 (nM) | CI |
|---|---|---|---|
| 1 | 2.3438 | 0.01875 | 17.124 |
| 2 | 2.3438 | 0.075 | 0.225 |
| 3 | 2.3438 | 0.15 | 0.346 |
| 4 | 2.3438 | 0.3 | 0.583 |
| 5 | 2.3438 | 0.6 | 1.165 |
| 6 | 2.3438 | 1.2 | 2.514 |
| 7 | 2.3438 | 0.0375 | 0.145 |
| 8 | 4.6875 | 0.01875 | 1.499 |
| 9 | 4.6875 | 0.0375 | 0.147 |
| 10 | 4.6875 | 0.075 | 0.216 |
| 11 | 4.6875 | 0.15 | 0.346 |
| 12 | 4.6875 | 0.3 | 0.628 |
| 13 | 4.6875 | 0.6 | 1.165 |
| 14 | 4.6875 | 1.2 | 2.514 |
| 15 | 9.375 | 0.01875 | 2.918 |
| 16 | 9.375 | 0.0375 | 0.144 |
| 17 | 9.375 | 0.075 | 0.219 |
| 18 | 9.375 | 0.15 | 0.332 |
| 19 | 9.375 | 0.3 | 0.583 |

TABLE 2-continued

Chou-Talalay Combination Index (CI) of different doses of LY75 DM4 in combination with Rituximab on three TMD8 ABC-DLBCL cell lines.

| No | Rituximab (nM) | LY75_DM4 (nM) | CI |
|---|---|---|---|
| 20 | 9.375 | 0.6 | 1.025 |
| 21 | 9.375 | 1.2 | 2.514 |
| 22 | 18.75 | 0.01875 | 0.8 |
| 23 | 18.75 | 0.0375 | 0.145 |
| 24 | 18.75 | 0.075 | 0.213 |
| 25 | 18.75 | 0.15 | 0.346 |
| 26 | 18.75 | 0.3 | 0.628 |
| 27 | 18.75 | 0.6 | 1.165 |
| 28 | 18.75 | 1.2 | 2.514 |
| 29 | 37.5 | 0.01875 | 11.427 |
| 30 | 37.5 | 0.075 | 0.216 |
| 31 | 37.5 | 0.15 | 0.332 |
| 32 | 37.5 | 0.3 | 0.583 |
| 33 | 37.5 | 0.6 | 1.165 |
| 34 | 37.5 | 1.2 | 2.655 |
| 35 | 37.5 | 0.0375 | 0.151 |
| 36 | 75 | 0.01875 | 0.216 |
| 37 | 75 | 0.0375 | 0.147 |
| 38 | 75 | 0.075 | 0.209 |
| 39 | 75 | 0.15 | 0.332 |
| 40 | 75 | 0.3 | 0.628 |
| 41 | 75 | 0.6 | 1.165 |
| 42 | 75 | 1.2 | 2.514 |
| 43 | 150 | 0.01875 | 45.466 |
| 44 | 150 | 0.0375 | 0.152 |
| 45 | 150 | 0.075 | 0.209 |
| 46 | 150 | 0.15 | 0.332 |
| 47 | 150 | 0.3 | 0.628 |
| 48 | 150 | 0.6 | 1.257 |
| 49 | 150 | 1.2 | 2.770 |

TABLE 3

Chou-Talalay Combination Index (CI) of different doses of LY75 DM4 in combination with Rituximab on three HBL-1 ABC-DLBCL cell lines.

| No | Rituximab (nM) | LY75_DM4 (nM) | CI |
|---|---|---|---|
| 1 | 2.3438 | 0.0188 | 0.534 |
| 2 | 2.3438 | 0.0750 | 0.958 |
| 3 | 2.3438 | 0.1500 | 0.603 |
| 4 | 2.3438 | 0.3000 | 0.509 |
| 5 | 2.3438 | 0.6000 | 0.454 |
| 6 | 2.3438 | 1.2000 | 0.817 |
| 7 | 2.3438 | 0.0375 | 0.413 |
| 8 | 4.6875 | 0.0188 | 0.568 |
| 9 | 4.6875 | 0.0375 | 0.837 |
| 10 | 4.6875 | 0.0750 | 0.919 |
| 11 | 4.6875 | 0.1500 | 0.635 |
| 12 | 4.6875 | 0.3000 | 0.580 |
| 13 | 4.6875 | 0.6000 | 0.501 |
| 14 | 4.6875 | 1.2000 | 0.908 |
| 15 | 9.375 | 0.0188 | 0.249 |
| 16 | 9.375 | 0.0375 | 1.576 |
| 17 | 9.375 | 0.0750 | 0.717 |
| 18 | 9.375 | 0.1500 | 0.439 |
| 19 | 9.375 | 0.3000 | 0.618 |
| 20 | 9.375 | 0.6000 | 0.501 |
| 21 | 9.375 | 1.2000 | 0.908 |
| 22 | 18.75 | 0.0188 | 0.787 |
| 23 | 18.75 | 0.0375 | 0.497 |
| 24 | 18.75 | 0.0750 | 0.562 |
| 25 | 18.75 | 0.1500 | 0.545 |
| 26 | 18.75 | 0.3000 | 0.510 |
| 27 | 18.75 | 0.6000 | 0.366 |
| 28 | 18.75 | 1.2000 | 0.817 |
| 29 | 37.50 | 0.0375 | 0.734 |
| 30 | 37.50 | 0.0750 | 0.548 |
| 31 | 37.50 | 0.0188 | 0.543 |
| 32 | 37.50 | 0.1500 | 0.465 |
| 33 | 37.50 | 0.3000 | 0.476 |
| 34 | 37.50 | 0.6000 | 0.324 |

TABLE 3-continued

Chou-Talalay Combination Index (CI) of different doses of LY75 DM4 in combination with Rituximab on three HBL-1 ABC-DLBCL cell lines.

| No | Rituximab (nM) | LY75_DM4 (nM) | CI |
|---|---|---|---|
| 35 | 37.50 | 1.2000 | 0.648 |
| 36 | 75 | 0.0188 | 0.442 |
| 37 | 75 | 0.0375 | 1.578 |
| 38 | 75 | 0.0750 | 0.432 |
| 39 | 75 | 0.1500 | 0.493 |
| 40 | 75 | 0.3000 | 0.383 |
| 41 | 75 | 0.6000 | 0.409 |
| 42 | 75 | 1.2000 | 0.908 |
| 43 | 150 | 0.0188 | 0.680 |
| 44 | 150 | 0.0375 | 0.640 |
| 45 | 150 | 0.0750 | 0.911 |
| 46 | 150 | 0.1500 | 0.498 |
| 47 | 150 | 0.3000 | 0.355 |
| 48 | 150 | 0.6000 | 0.366 |
| 49 | 150 | 1.2000 | 0.817 |

TABLE 4

Chou-Talalay Combination Index (CI) of different doses of LY75 DM4 in combination with Ibrutinib on three HBL-1 ABC-DLBCL cell lines.

| No | Ibrutinib (nM) | LY75_DM4 (nM) | CI |
|---|---|---|---|
| 1 | 1.5625 | 0.01875 | 0.481 |
| 2 | 1.5625 | 0.0375 | 0.627 |
| 3 | 1.5625 | 0.075 | 0.862 |
| 4 | 1.5625 | 0.15 | 0.360 |
| 5 | 1.5625 | 0.3 | 0.287 |
| 6 | 1.5625 | 0.6 | 0.270 |
| 7 | 1.5625 | 1.2 | 0.343 |
| 8 | 3.125 | 0.01875 | 0.411 |
| 9 | 3.125 | 0.0375 | 0.358 |
| 10 | 3.125 | 0.075 | 0.461 |
| 11 | 3.125 | 0.15 | 0.287 |
| 12 | 3.125 | 0.3 | 0.251 |
| 13 | 3.125 | 0.6 | 0.246 |
| 14 | 3.125 | 1.2 | 0.394 |
| 15 | 6.25 | 0.01875 | 0.204 |
| 16 | 6.25 | 0.0375 | 0.219 |
| 17 | 6.25 | 0.075 | 0.275 |
| 18 | 6.25 | 0.15 | 0.226 |
| 19 | 6.25 | 0.3 | 0.216 |
| 20 | 6.25 | 0.6 | 0.222 |
| 21 | 6.25 | 1.2 | 0.343 |
| 22 | 12.5 | 0.01875 | 0.205 |
| 23 | 12.5 | 0.0375 | 0.152 |
| 24 | 12.5 | 0.075 | 0.287 |
| 25 | 12.5 | 0.15 | 0.217 |
| 26 | 12.5 | 0.3 | 0.228 |
| 27 | 12.5 | 0.6 | 0.222 |
| 28 | 12.5 | 1.2 | 0.343 |
| 29 | 25 | 0.01875 | 0.152 |
| 30 | 25 | 0.0375 | 0.183 |
| 31 | 25 | 0.075 | 0.202 |
| 32 | 25 | 0.15 | 0.199 |
| 33 | 25 | 0.3 | 0.193 |
| 34 | 25 | 0.6 | 0.222 |
| 35 | 25 | 1.2 | 0.343 |
| 36 | 50 | 0.01875 | 0.374 |
| 37 | 50 | 0.0375 | 0.473 |
| 38 | 50 | 0.075 | 0.287 |
| 39 | 50 | 0.15 | 0.192 |
| 40 | 50 | 0.3 | 0.194 |
| 41 | 50 | 0.6 | 0.246 |
| 42 | 50 | 1.2 | 0.394 |
| 43 | 100 | 0.01875 | 0.715 |
| 44 | 100 | 0.0375 | 0.748 |
| 45 | 100 | 0.075 | 0.457 |
| 46 | 100 | 0.15 | 0.187 |
| 47 | 100 | 0.3 | 0.195 |
| 48 | 100 | 0.6 | 0.222 |
| 49 | 100 | 1.2 | 0.394 |

SEQUENCES:

| SEQ ID No | Description | Sequence |
|---|---|---|
| 1 | A1_VH aa | EVQLVESGGGLVKPGGSLRLSCAASGFTYSNAWMSWVRQAPGK GLEWVGRIKSKTDGGTTDYAAPVQGRFTISRDDSKNTLYLQMN SLKTEDTAVYYCTIFGVVSFDYWGQGTLVTVSS |
| 2 | A1_VL aa | DVQMTQSPSSLSASVGDRVTITCRASQSISDYLSWYQQRPGKA PNLLIYAASNLKTGVPSRFSGSGSGTDFTLTISTLQPEDFATY YCQQSYRSPWTFGQGTKVEIKR |
| 3 | A1_VH nt | gaggtgcagctggtggagtctgggggaggcttggtaaagccgg gggggtcccttagactctcctgtgcagcctctggcttcactta cagtaacgcctggatgagctgggtccgccaggctccagggaag gggctggagtgggttggccgtattaaaagcaaaactgatggtg ggacaacagactacgctgcacccgtgcaaggcagattcaccat ctcaagagatgattcaaaaaacacgctgtatctgcaaatgaac agcctgaaaaccgaggacacagccgtgtattactgtacgattt ttggagtggttagctttgactactggggccagggaaccctggt caccgtctcctca |
| 4 | A1_VL nt | gacgtccagatgacccagtctccatcctccctgtctgcatctg ttggagacagagtcaccatcacttgccgggcaagtcagagcat tagcgactatttaagttggtatcagcagagaccagggaaagcc cctaacctcctgatctatgctgcatccaatttaaagactgggg tcccatcaaggttcagtggcagtggatctgggacagatttcac tctcaccatcagcactctgcaacctgaagattttgcaacgtac tactgtcaacagagttacaggtccccgtggacgttcggccaag ggaccaaggtggaaatcaaacga |
| 5 | A1_VH_CDR1 aa | NAWMS |
| 6 | A1_VH_CDR2 aa | RIKSKTDGGTTDYAAPVQG |
| 7 | A1_VH_CDR3 aa | FGVVSFDY |
| 8 | A1_VL_CDR1 aa | RASQSISDYLS |
| 9 | A1_VL_CDR2 aa | AASNLKT |
| 10 | A1_VL_CDR3 aa | QQSYRSPWT |
| 11 | VH3\|3-15/D4\|411 | EVQLVESGGGLVKPGGSLRLSCAASGFTFSNAWMSWVRQAPGK GLEWVGRIKSKTDGGTTDYAAPVKGRFTISRDDSKNTLYLQMN SLKTEDTAVYYCTTTTVT |
| 12 | JH4 | YFDYWGQGTLVTVSS |
| 13 | O12 | DIQMTQSPSSLSASVGDRVTITCRASQSISSYLNWYQQKPGKA PKLLIYAASSLQSGVPSRFSGSGSGTDFTLTISSLQPEDFATY YCQQSYS |
| 14 | JK1 | WTFGQGTKVEIKR |
| 15 | LY75 (DEC-205) | MRTGWATPRRPAGLLMLLFWFFDLAEPSGRAANDPFTIVHGNT GKCIKPVYGWIVADDCDETEDKLWKWVSQHRLFHLHSQKCLGL DITKSVNELRMFSCDSSAMLWWKCEHHSLYGAARYRLALKDGH GTAISNASDVWKKGGSEESLCDQPYHEIYTRDGNSYGRPCEFP FLIDGTWHHDCILDEDHSGPWCATTLNYEYDRKWGICLKPENG CEDNWEKNEQFGSCYQFNTQTALSWKEAYVSCQNQGADLLSIN SAAELTYLKEKEGIAKIFWIGLNQLYSARGWEWSDHKPLNFLN WDPDRPSAPTIGGSSCARMDAESGLWQSFSCEAQLPYVCRKPL NNTVELTDVWTYSDTRCDAGWLPNNGFCYLLVNESNSWDKAHA KCKAFSSDLISIHSLADVEVVTKLHNEDIKEEVWIGLKNINI PTLFQWSDGTEVTLTYWDENEPNVPYNKTPNCVSYLGELGQWK VQSCEEKLKYVCKRKGEKLNDASSDKMCPPDEGWKRHGETCYK IYEDEVPFGTNCNLTITSRFEQEYLNDLMKKYDKSLRKYFWTG LRDVDSCGEYNWATVGGRRRAVTFSNWNFLEPASPGGCVAMST GKSVGKWEVKDCRSFKALSICKKMSGPLGPEEASPKPDDPCPE GWQSFPASLSCYKVFHAERIVRKRNWEEAERFCQALGAHLSSF SHVDEIKEFLHFLTDQFSGQHWLWIGLNKRSPDLQGSWQWSDR TPVSTIIMPNEFQQDYDIRDCAAVKVFHRPWRRGWHFYDDREF IYLRPFACDTKLEWVCQIPKGRTPKTPDVVYNPDRAGIHGPPL IIEGSEYWFVADLHLNYEEAVLYCASNHSFLATITSFVGLKAI KNKIANISGDGQKVWVIRISEWPIDDHFTYSRYPWHRFPVTFG EECLYMSAKTWLIDLGKPTDCSTKLPFICEKYNVSSLEKYSPD SAAKVQCSEQWIPFQNKCFLKIKPVSLTFSQASDTCHSYGGTL PSVLSQIEQDFITSLLPDMEATLWIGLRWTAYEKINKWTDNRE LTYSNFHPLLVSGRLRIPENFFEEESRYHCALILNLQKSPFTG |

-continued

SEQUENCES:

| SEQ ID No | Description | Sequence |
|---|---|---|
| | | TWNFTSCSERHFVSLCQKYSEVKSRQTLQNASETVKYLNNLYK IIPKTLTWHSAKRECLKSNMQLVSITDPYQQAFLSVQALLHNS SLWIGLFSQDDELNFGWSDGKRLHFSRWAETNGQLEDCVVLDT DGFWKTVDCNDNQPGAICYYSGNETEKEVKPVDSVKCPSPVLN TPWIPFQNCCYNFIITKNRHMATTQDEVHTKCQKLNPKSHILS IRDEKENNFVLEQLLYFNYMASWVMLGITYRNKSLMWFDKTPL SYTHWRAGRPTIKNEKFLAGLSTDGFWDIQTFKVIEEAVYFHQ HSILACKIEMVDYKEEYNTTLPQFMPYEDGIYSVIQKKVTWYE ALNMCSQSGGHLASVHNQNGQLFLEDIVKRDGFPLWVGLSSHD GSESSFEWSDGSTFDYIPWKGQTSPGNCVLLDPKGTWKHEKCN SVKDGAICYKPTKSKKLSRLTYSSRCPAAKENGSRWIQYKGHC YKSDQALHSFSEAKKLCSKHDHSATIVSIKDEDENKFVSRLMR ENNNITMRVWLGLSQHSVDQSWSWLDGSEVTFVKWENKSKSGV GRCSMLIASNETWKKVECEHGFGRVVCKVPLGPDYTAIAIIVA TLSILVLMGGLIWFLFQRHRLHLAGFSSVRYAQGVNEDEIMLP SFHD |
| 16 | A1_VH_FR1 | EVQLVESGGGLVKPGGSLRLSCAASGFTYS |
| 17 | A1_VH_FR2 | WVRQAPGKGLEWVG |
| 18 | A1_VH_FR3 | RFTISRDDSKNTLYLQMNSLKTEDTAVYYCTI |
| 19 | A1_VH_FR4 | WGQGTLVTVSS |
| 20 | A1_VL_FR1 | DVQMTQSPSSLSASVGDRVTITC |
| 21 | A1_VL_FR2 | WYQQRPGKAPNLLIY |
| 22 | A1_VL_FR3 | GVPSRFSGSGSGTDFTLTISTLQPEDFATYYC |
| 23 | A1_VL_FR4 | FGQGTKVEIKR |
| 24 | LY75 609-618 | WEVKDCRSFK |
| 25 | LY75 651-662 | PASLSCYKVFHA |
| 26 | LY75 761-780 | PWRRGWHFYDDREFIYLRPF |
| 27 | LY75 883-901 | DDHFTYSRYPWHRFPVTFG |
| 28 | LY75 1029-1040 | RELTYSNFHPLL |
| 29 | LY75 1077-1093 | FTSCSERHFVSLCQKYS |
| 30 | LY75 1107-1118 | TVKYLNNLYKII |
| 31 | LY75 1368-1378 | EAVYFHQHSIL |
| 32 | LY75 1518-1528 | KKLSRLTYSSC |
| 33 | LY75 1535-1554 | NGSRWIQYKGHCYKSDQALH |
| 34 | LY75 877-901 | ISEWPIDDHFTYSRYPWHRFPVTFG |
| 35 | LY75 1099-1118 | QTLQNASETVKYLNNLYKII |
| 36 | LY75 883-892 | DDHFTYSRYP |
| 37 | LY75 1077-1091 | FTSCSERHFVSLCQK |
| 38 | Rituximab VH | QVQLQQPGAELVKPGASVKMSCKASGYTFTSYNMHWVKQTPGR GLEWIGAIYPGNGDTSYNQKFKGKATLTADKSSSTAYMQLSSL TSEDSAVYYCARSTYYGGDWYFNVWGAGTTVTVSAASTKGPSV FPLAPSSKSTSGGTAALGCLVKDYFPEPVTVSWNSGALTSGVH TFPAVLQSSGLYSLSSVVTVPSSSLGTQTYICNVNHKPSNTKV DKKAEPKSCDKTHTCPPCPAPELLGGPSVFLFPPKPKDTLMIS RTPEVTCVVVDVSHEDPEVKFNWYVDGVEVHNAKTKPREEQYN STYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSCS VMHEALHNHYTQKSLSLSPGK |

-continued

SEQUENCES:

| SEQ ID No | Description | Sequence |
|---|---|---|
| 39 | Rituximab VL | QIVLSQSPAILSASPGEKVTMTCRASSSVSYIHWFQQKPGSSP KPWIYATSNLASGVPVRFSGSGSGTSYSLTISRVEAEDAATYY CQQWTSNPPTFGGGTKLEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| 40 | Rituximab VH_CDR1 | SYNMH |
| 41 | Rituximab VH_CDR2 | AIYPGNGDTSYNQKFKG |
| 42 | Rituximab VH_CDR3 | STYYGGDWYFNV |
| 43 | Rituximab VL_CDR1 | RASSSVSYIH |
| 44 | Rituximab VL_CDR2 | ATSNLAS |
| 45 | Rituximab VL_CDR3 | QQWTSNPPTF |
| 46 | (765-772) | GWHFYDDR |
| 47 | (877 to 890) | ISEWPIDDHFTYSR |
| 48 | (896-910) | FPVTFGEECLYMSAK |
| 49 | (1030-1044) | ELTYSNFHPLLVSGR |
| 50 | (1084-1091) | HFVSLCQK |
| 51 | (1099-1109) | QTLQNASETVK |
| 52 | Linker | Gly-Phe-Leu-Gly |

Sequence Listing Free Text

SEQ ID NO: 38 <223> Rituximab VH sequence
SEQ ID NO: 39 <223> Rituximab VL sequence
SEQ ID NO: 40 <223> Rituximab VH_CDR1
SEQ ID NO: 41 <223> Rituximab VH_CDR2
SEQ ID NO: 42 <223> Rituximab VH_CDR3
SEQ ID NO: 43 <223> Rituximab VL_CDR1
SEQ ID NO: 44 <223> Rituximab VL_CDR2
SEQ ID NO: 45 <223> Rituximab VL_CDR3
SEQ ID NO: 52 <223> Linker
SEQ ID NOs: 53-163 <223> Peptide
SEQ ID NOs: 165-207 <223> Peptide

The invention claimed is:

1. A method of treating cancer in a subject comprising simultaneously, sequentially or separately administering to the subject in need thereof therapeutically-effective amounts of components (A) and (B) of a pharmaceutical combination comprising: (A) an anti-LY75 antibody, or an antigen-binding portion thereof, said antibody or portion thereof comprising: a) a heavy chain variable region comprising: i) a first vhCDR comprising SEQ ID NO:5; ii) a second vhCDR comprising SEQ ID NO: 6; and iii) a third vhCDR comprising SEQ ID NO: 7; and b) a light chain variable region comprising: i) a first vlCDR comprising SEQ ID NO:8; ii) a second vlCDR comprising SEQ ID NO: 9; and iii) a third vlCDR comprising SEQ ID NO: 10; wherein the anti-LY75 antibody or antigen-binding portion thereof further comprises a covalently-attached drug, and wherein said drug is a maytansinoid or a derivative thereof and (B) ibrutinib or a pharmaceutically-acceptable salt thereof.

2. The method of claim 1, wherein the anti-LY75 antibody or antigen-binding portion thereof is internalized by a cell expressing LY75.

3. The method of claim 1, wherein the maytansinoid is DM4 or DM1.

4. The method of claim 1, wherein the cancer is diffuse large B-cell lymphoma (DLBCL) or Non-Hodgkin's lymphoma.

5. The method of claim 1, wherein the anti-LY75 antibody or an antigen-binding portion thereof comprises a heavy chain variable region comprising SEQ ID NO: 1 and a light chain variable region comprising SEQ ID NO: 2.

6. The method of claim 1, wherein the anti-LY75 antibody is a human IgG1 monoclonal antibody.

7. The method of claim 1, wherein (A) and/or (B) additionally comprise one or more pharmaceutically-acceptable diluents, excipients or carriers.

* * * * *

SEQUENCE LISTING

```
Sequence total quantity: 208
SEQ ID NO: 1           moltype = AA  length = 119
FEATURE                Location/Qualifiers
source                 1..119
                       mol_type = protein
                       organism = Homo sapiens
SEQUENCE: 1
EVQLVESGGG LVKPGGSLRL SCAASGFTYS NAWMSWVRQA PGKGLEWVGR IKSKTDGGTT  60
DYAAPVQGRF TISRDDSKNT LYLQMNSLKT EDTAVYYCTI FGVVSFDYWG QGTLVTVSS   119

SEQ ID NO: 2           moltype = AA  length = 108
FEATURE                Location/Qualifiers
source                 1..108
                       mol_type = protein
                       organism = Homo sapiens
SEQUENCE: 2
DVQMTQSPSS LSASVGDRVT ITCRASQSIS DYLSWYQQRP GKAPNLLIYA ASNLKTGVPS  60
RFSGSGSGTD FTLTISTLQP EDFATYYCQQ SYRSPWTFGQ GTKVEIKR               108

SEQ ID NO: 3           moltype = DNA  length = 357
```

-continued

```
FEATURE                 Location/Qualifiers
source                  1..357
                        mol_type = unassigned DNA
                        organism = Homo sapiens
SEQUENCE: 3
gaggtgcagc tggtggagtc tgggggaggc ttggtaaagc cggggggtc ccttagactc  60
tcctgtgcag cctctggctt cacttacagt aacgcctgga tgagctgggt ccgccaggct  120
ccagggaagg ggctggagtg ggttggccgt attaaaagca aaactgatgg tgggacaaca  180
gactacgctg cacccgtgca aggcagattc accatctcaa gagatgattc aaaaaacacg  240
ctgtatctgc aaatgaacag cctgaaaacc gaggacacag ccgtgtatta ctgtacgatt  300
tttggagtgg ttagctttga ctactggggc cagggaaccc tggtcaccgt ctcctca     357

SEQ ID NO: 4            moltype = DNA  length = 324
FEATURE                 Location/Qualifiers
source                  1..324
                        mol_type = unassigned DNA
                        organism = Homo sapiens
SEQUENCE: 4
gacgtccaga tgacccagtc tccatcctcc ctgtctgcat ctgttggaga cagagtcacc  60
atcacttgcc gggcaagtca gagcattagc gactatttaa gttggtatca gcagagacca  120
gggaaagccc ctaacctcct gatctatgct gcatccaatt taaagactgg ggtcccatca  180
aggttcagtg gcagtggatc tgggacagat ttcactctca ccatcagcac tctgcaacct  240
gaagattttg caacgtacta ctgtcaacag agttacaggt ccccgtggac gttcggccaa  300
gggaccaagg tggaaatcaa acga                                          324

SEQ ID NO: 5            moltype = AA  length = 5
FEATURE                 Location/Qualifiers
source                  1..5
                        mol_type = protein
                        organism = Homo sapiens
SEQUENCE: 5
NAWMS                                                               5

SEQ ID NO: 6            moltype = AA  length = 19
FEATURE                 Location/Qualifiers
source                  1..19
                        mol_type = protein
                        organism = Homo sapiens
SEQUENCE: 6
RIKSKTDGGT TDYAAPVQG                                                19

SEQ ID NO: 7            moltype = AA  length = 8
FEATURE                 Location/Qualifiers
source                  1..8
                        mol_type = protein
                        organism = Homo sapiens
SEQUENCE: 7
FGVVSFDY                                                            8

SEQ ID NO: 8            moltype = AA  length = 11
FEATURE                 Location/Qualifiers
source                  1..11
                        mol_type = protein
                        organism = Homo sapiens
SEQUENCE: 8
RASQSISDYL S                                                        11

SEQ ID NO: 9            moltype = AA  length = 7
FEATURE                 Location/Qualifiers
source                  1..7
                        mol_type = protein
                        organism = Homo sapiens
SEQUENCE: 9
AASNLKT                                                             7

SEQ ID NO: 10           moltype = AA  length = 9
FEATURE                 Location/Qualifiers
source                  1..9
                        mol_type = protein
                        organism = Homo sapiens
SEQUENCE: 10
QQSYRSPWT                                                           9

SEQ ID NO: 11           moltype = AA  length = 104
FEATURE                 Location/Qualifiers
source                  1..104
                        mol_type = protein
                        organism = Homo sapiens
SEQUENCE: 11
```

-continued

```
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT TTVT                 104

SEQ ID NO: 12          moltype = AA  length = 15
FEATURE                Location/Qualifiers
source                 1..15
                       mol_type = protein
                       organism = Homo sapiens
SEQUENCE: 12
YFDYWGQGTL VTVSS                                                 15

SEQ ID NO: 13          moltype = AA  length = 93
FEATURE                Location/Qualifiers
source                 1..93
                       mol_type = protein
                       organism = Homo sapiens
SEQUENCE: 13
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYS                             93

SEQ ID NO: 14          moltype = AA  length = 13
FEATURE                Location/Qualifiers
source                 1..13
                       mol_type = protein
                       organism = Homo sapiens
SEQUENCE: 14
WTFGQGTKVE IKR                                                   13

SEQ ID NO: 15          moltype = AA  length = 1722
FEATURE                Location/Qualifiers
source                 1..1722
                       mol_type = protein
                       organism = Homo sapiens
SEQUENCE: 15
MRTGWATPRR PAGLLMLLFW FFDLAEPSGR AANDPFTIVH GNTGKCIKPV YGWIVADDCD  60
ETEDKLWKWV SQHRLFHLHS QKCLGLDITK SVNELRMFSC DSSAMLWWKC EHHSLYGAAR  120
YRLALKDGHG TAISNASDVW KKGGSEESLC DQPYHEIYTR DGNSYGRPCE FPFLIDGTWH  180
HDCILDEDHS GPWCATTLNY EYDRKWGICL KPENGCEDNW EKNEQFGSCY QFNTQTALSW  240
KEAYVSCQNQ GADLLSINSA AELTYLKEKE GIAKIFWIGL NQLYSARGWE WSDHKPLNFL  300
NWDPDRPSAP TIGGSSCARM DAESGLWQSF SCEAQLPYVC RKPLNNTVEL TDVWTYSDTR  360
CDAGWLPNNG FCYLLVNESN SWDKAHAKCK AFSSDLISIH SLADVEVVVT KLHNEDIKEE  420
VWIGLKNINI PTLFQWSDGT EVTLTYWDEN EPNVPYNKTP NCVSYLGELG QWKVQSCEEK  480
LKYVCKRKGE KLNDASSDKM CPPDEGWKRH GETCYKIYED EVPFGTNCNL TITSRFEQEY  540
LNDLMKKYDK SLRKYFWTGL RDVDSCGEYN WATVGGRRRA VTFSNWNFLE PASPGGCVAM  600
STGKSVGKWE VKDCRSFKAL SICKKMSGPL GPEEASPKPD DPCPEGWQSF PASLSCYKVF  660
HAERIVRKRN WEEAERFCQA LGAHLSSFSH VDEIKEFLHF LTDQFSGQHW LWIGLNKRSP  720
DLQGSWQWSD RTPVSTIIMP NEFQQDYDIR DCAAVKVFHR PWRRGWHFYD DREFIYLRPF  780
ACDTKLEWVC QIPKGRTPKT PDWYNPDRAG IHGPPLIIEG SEYWFVADLH LNYEEAVLYC  840
ASNHSFLATI TSFVGLKAIK NKIANISGDG QKWWIRISEW PIDDHFTYSR YPWHRFPVTF  900
GEECLYMSAK TWLIDLGKPT DCSTKLPFIC EKYNVSSLEK YSPDSAAKVQ CSEQWIPFQN  960
KCFLKIKPVS LTFSQASDTC HSYGGTLPSV LSQIEQDFIT SLLPDMEATL WIGLRWTAYE  1020
KINKWTDNRE LTYSNFHPLL VSGRLRIPEN FFEEESRYHC ALILNLQKSP FTGTWNFTSC  1080
SERHFVSLCQ KYSEVKSRQT LQNASETVKY LNNLYKIIPK TLTWHSAKRE CLKSNMQLVS  1140
ITDPYQQAFL SVQALLHNSS LWIGLFSQDD ELNFGWSDGK RLHFSRWAET NGQLEDCVVL  1200
DTDGFWKTVD CNDNQPGAIC YYSGNETEKE VKPVDSVKCP SPVLNTPWIP FQNCCYNFII  1260
TKNRHMATTQ DEVHTKCQKL NPKSHILSIR DEKENNFVLE QLLYFNYMAS WVMLGITYRN  1320
KSLMWFDKTP LSYTHWRAGR PTIKNEKFLA GLSTDGFWDI QTFKVIEEAV YFHQHSILAC  1380
KIEMVDYKEE YNTTLPQFMP YEDGIYSVIQ KKVTWYEALN MCSQSGGHLA SVHNQNGQLF  1440
LEDIVKRDGF PLWVGLSSHD GSESSFEWSD GSTFDYIPWK GQTSPGNCVL LDPKGTWKHE  1500
KCNSVKDGAI CYKPTKSKKL SRLTYSSRCP AAKENGSRWI QYKGHCYKSD QALHSFSEAK  1560
KLCSKHDHSA TIVSIKDEDE NKFVSRLMRE NNNITMRVWL GLSQHSVDQS WSWLDGSEVT  1620
FVKWENKSKS GVGRCSMLIA SNETWKKVEC EHGFGRVVCK VPLGPDYTAI AIIVATLSIL  1680
VLMGGLIWFL FQRHRLHLAG FSSVRYAQGV NEDEIMLPSF HD                   1722

SEQ ID NO: 16          moltype = AA  length = 30
FEATURE                Location/Qualifiers
source                 1..30
                       mol_type = protein
                       organism = Homo sapiens
SEQUENCE: 16
EVQLVESGGG LVKPGGSLRL SCAASGFTYS                                 30

SEQ ID NO: 17          moltype = AA  length = 14
FEATURE                Location/Qualifiers
source                 1..14
                       mol_type = protein
                       organism = Homo sapiens
SEQUENCE: 17
WVRQAPGKGL EWVG                                                  14
```

```
SEQ ID NO: 18          moltype = AA  length = 32
FEATURE                Location/Qualifiers
source                 1..32
                       mol_type = protein
                       organism = Homo sapiens
SEQUENCE: 18
RFTISRDDSK NTLYLQMNSL KTEDTAVYYC TI                                    32

SEQ ID NO: 19          moltype = AA  length = 11
FEATURE                Location/Qualifiers
source                 1..11
                       mol_type = protein
                       organism = Homo sapiens
SEQUENCE: 19
WGQGTLVTVS S                                                           11

SEQ ID NO: 20          moltype = AA  length = 23
FEATURE                Location/Qualifiers
source                 1..23
                       mol_type = protein
                       organism = Homo sapiens
SEQUENCE: 20
DVQMTQSPSS LSASVGDRVT ITC                                              23

SEQ ID NO: 21          moltype = AA  length = 15
FEATURE                Location/Qualifiers
source                 1..15
                       mol_type = protein
                       organism = Homo sapiens
SEQUENCE: 21
WYQQRPGKAP NLLIY                                                       15

SEQ ID NO: 22          moltype = AA  length = 32
FEATURE                Location/Qualifiers
source                 1..32
                       mol_type = protein
                       organism = Homo sapiens
SEQUENCE: 22
GVPSRFSGSG SGTDFTLTIS TLQPEDFATY YC                                    32

SEQ ID NO: 23          moltype = AA  length = 11
FEATURE                Location/Qualifiers
source                 1..11
                       mol_type = protein
                       organism = Homo sapiens
SEQUENCE: 23
FGQGTKVEIK R                                                           11

SEQ ID NO: 24          moltype = AA  length = 10
FEATURE                Location/Qualifiers
source                 1..10
                       mol_type = protein
                       organism = Homo sapiens
SEQUENCE: 24
WEVKDCRSFK                                                             10

SEQ ID NO: 25          moltype = AA  length = 12
FEATURE                Location/Qualifiers
source                 1..12
                       mol_type = protein
                       organism = Homo sapiens
SEQUENCE: 25
PASLSCYKVF HA                                                          12

SEQ ID NO: 26          moltype = AA  length = 20
FEATURE                Location/Qualifiers
source                 1..20
                       mol_type = protein
                       organism = Homo sapiens
SEQUENCE: 26
PWRRGWHFYD DREFIYLRPF                                                  20

SEQ ID NO: 27          moltype = AA  length = 19
FEATURE                Location/Qualifiers
source                 1..19
                       mol_type = protein
                       organism = Homo sapiens
SEQUENCE: 27
```

-continued

```
DDHFTYSRYP WHRFPVTFG                                              19

SEQ ID NO: 28          moltype = AA  length = 12
FEATURE                Location/Qualifiers
source                 1..12
                       mol_type = protein
                       organism = Homo sapiens
SEQUENCE: 28
RELTYSNFHP LL                                                     12

SEQ ID NO: 29          moltype = AA  length = 17
FEATURE                Location/Qualifiers
source                 1..17
                       mol_type = protein
                       organism = Homo sapiens
SEQUENCE: 29
FTSCSERHFV SLCQKYS                                                17

SEQ ID NO: 30          moltype = AA  length = 12
FEATURE                Location/Qualifiers
source                 1..12
                       mol_type = protein
                       organism = Homo sapiens
SEQUENCE: 30
TVKYLNNLYK II                                                     12

SEQ ID NO: 31          moltype = AA  length = 11
FEATURE                Location/Qualifiers
source                 1..11
                       mol_type = protein
                       organism = Homo sapiens
SEQUENCE: 31
EAVYFHQHSI L                                                      11

SEQ ID NO: 32          moltype = AA  length = 11
FEATURE                Location/Qualifiers
source                 1..11
                       mol_type = protein
                       organism = Homo sapiens
SEQUENCE: 32
KKLSRLTYSS C                                                      11

SEQ ID NO: 33          moltype = AA  length = 20
FEATURE                Location/Qualifiers
source                 1..20
                       mol_type = protein
                       organism = Homo sapiens
SEQUENCE: 33
NGSRWIQYKG HCYKSDQALH                                             20

SEQ ID NO: 34          moltype = AA  length = 25
FEATURE                Location/Qualifiers
source                 1..25
                       mol_type = protein
                       organism = Homo sapiens
SEQUENCE: 34
ISEWPIDDHF TYSRYPWHRF PVTFG                                       25

SEQ ID NO: 35          moltype = AA  length = 20
FEATURE                Location/Qualifiers
source                 1..20
                       mol_type = protein
                       organism = Homo sapiens
SEQUENCE: 35
QTLQNASETV KYLNNLYKII                                             20

SEQ ID NO: 36          moltype = AA  length = 10
FEATURE                Location/Qualifiers
source                 1..10
                       mol_type = protein
                       organism = Homo sapiens
SEQUENCE: 36
DDHFTYSRYP                                                        10

SEQ ID NO: 37          moltype = AA  length = 15
FEATURE                Location/Qualifiers
source                 1..15
                       mol_type = protein
                       organism = Homo sapiens
```

-continued

```
SEQUENCE: 37
FTSCSERHFV SLCQK                                                  15

SEQ ID NO: 38          moltype = AA  length = 451
FEATURE                Location/Qualifiers
REGION                 1..451
                       note = Rituximab VH sequence
source                 1..451
                       mol_type = protein
                       organism = synthetic construct
SEQUENCE: 38
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKAE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 39          moltype = AA  length = 213
FEATURE                Location/Qualifiers
REGION                 1..213
                       note = Rituximab VL sequence
source                 1..213
                       mol_type = protein
                       organism = synthetic construct
SEQUENCE: 39
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 40          moltype = AA  length = 5
FEATURE                Location/Qualifiers
REGION                 1..5
                       note = Rituximab VH_CDR1
source                 1..5
                       mol_type = protein
                       organism = synthetic construct
SEQUENCE: 40
SYNMH                                                             5

SEQ ID NO: 41          moltype = AA  length = 17
FEATURE                Location/Qualifiers
REGION                 1..17
                       note = Rituximab VH_CDR2
source                 1..17
                       mol_type = protein
                       organism = synthetic construct
SEQUENCE: 41
AIYPGNGDTS YNQKFKG                                                17

SEQ ID NO: 42          moltype = AA  length = 12
FEATURE                Location/Qualifiers
REGION                 1..12
                       note = Rituximab VH_CDR3
source                 1..12
                       mol_type = protein
                       organism = synthetic construct
SEQUENCE: 42
STYYGGDWYF NV                                                     12

SEQ ID NO: 43          moltype = AA  length = 10
FEATURE                Location/Qualifiers
REGION                 1..10
                       note = Rituximab VL_CDR1
source                 1..10
                       mol_type = protein
                       organism = synthetic construct
SEQUENCE: 43
RASSSVSYIH                                                        10

SEQ ID NO: 44          moltype = AA  length = 7
FEATURE                Location/Qualifiers
REGION                 1..7
                       note = Rituximab VL_CDR2
source                 1..7
                       mol_type = protein
```

-continued

```
                         organism = synthetic construct
SEQUENCE: 44
ATSNLAS                                                                    7

SEQ ID NO: 45            moltype = AA  length = 10
FEATURE                  Location/Qualifiers
REGION                   1..10
                         note = Rituximab VL_CDR3
source                   1..10
                         mol_type = protein
                         organism = synthetic construct
SEQUENCE: 45
QQWTSNPPTF                                                                 10

SEQ ID NO: 46            moltype = AA  length = 8
FEATURE                  Location/Qualifiers
source                   1..8
                         mol_type = protein
                         organism = Homo sapiens
SEQUENCE: 46
GWHFYDDR                                                                   8

SEQ ID NO: 47            moltype = AA  length = 14
FEATURE                  Location/Qualifiers
source                   1..14
                         mol_type = protein
                         organism = Homo sapiens
SEQUENCE: 47
ISEWPIDDHF TYSR                                                            14

SEQ ID NO: 48            moltype = AA  length = 15
FEATURE                  Location/Qualifiers
source                   1..15
                         mol_type = protein
                         organism = Homo sapiens
SEQUENCE: 48
FPVTFGEECL YMSAK                                                           15

SEQ ID NO: 49            moltype = AA  length = 15
FEATURE                  Location/Qualifiers
source                   1..15
                         mol_type = protein
                         organism = Homo sapiens
SEQUENCE: 49
ELTYSNFHPL LVSGR                                                           15

SEQ ID NO: 50            moltype = AA  length = 8
FEATURE                  Location/Qualifiers
source                   1..8
                         mol_type = protein
                         organism = Homo sapiens
SEQUENCE: 50
HFVSLCQK                                                                   8

SEQ ID NO: 51            moltype = AA  length = 11
FEATURE                  Location/Qualifiers
source                   1..11
                         mol_type = protein
                         organism = Homo sapiens
SEQUENCE: 51
QTLQNASETV K                                                               11

SEQ ID NO: 52            moltype = AA  length = 4
FEATURE                  Location/Qualifiers
REGION                   1..4
                         note = Linker
source                   1..4
                         mol_type = protein
                         organism = synthetic construct
SEQUENCE: 52
GFLG                                                                       4

SEQ ID NO: 53            moltype = AA  length = 8
FEATURE                  Location/Qualifiers
REGION                   1..8
                         note = Peptide
source                   1..8
                         mol_type = protein
                         organism = synthetic construct
```

```
SEQUENCE: 53
WEVKDCRS                                                        8

SEQ ID NO: 54           moltype = AA  length = 8
FEATURE                 Location/Qualifiers
REGION                  1..8
                        note = Peptide
source                  1..8
                        mol_type = protein
                        organism = synthetic construct
SEQUENCE: 54
EVKDCRSF                                                        8

SEQ ID NO: 55           moltype = AA  length = 8
FEATURE                 Location/Qualifiers
REGION                  1..8
                        note = Peptide
source                  1..8
                        mol_type = protein
                        organism = synthetic construct
SEQUENCE: 55
VKDCRSFK                                                        8

SEQ ID NO: 56           moltype = AA  length = 8
FEATURE                 Location/Qualifiers
REGION                  1..8
                        note = Peptide
source                  1..8
                        mol_type = protein
                        organism = synthetic construct
SEQUENCE: 56
KDCRSFKA                                                        8

SEQ ID NO: 57           moltype = AA  length = 8
FEATURE                 Location/Qualifiers
REGION                  1..8
                        note = Peptide
source                  1..8
                        mol_type = protein
                        organism = synthetic construct
SEQUENCE: 57
DCRSFKAL                                                        8

SEQ ID NO: 58           moltype = AA  length = 8
FEATURE                 Location/Qualifiers
REGION                  1..8
                        note = Peptide
source                  1..8
                        mol_type = protein
                        organism = synthetic construct
SEQUENCE: 58
CRSFKALS                                                        8

SEQ ID NO: 59           moltype = AA  length = 8
FEATURE                 Location/Qualifiers
REGION                  1..8
                        note = Peptide
source                  1..8
                        mol_type = protein
                        organism = synthetic construct
SEQUENCE: 59
RSFKALSI                                                        8

SEQ ID NO: 60           moltype = AA  length = 8
FEATURE                 Location/Qualifiers
REGION                  1..8
                        note = Peptide
source                  1..8
                        mol_type = protein
                        organism = synthetic construct
SEQUENCE: 60
PASLSCYK                                                        8

SEQ ID NO: 61           moltype = AA  length = 8
FEATURE                 Location/Qualifiers
REGION                  1..8
                        note = Peptide
source                  1..8
                        mol_type = protein
```

-continued

```
                       organism = synthetic construct
SEQUENCE: 61
ASLSCYKV                                                                   8

SEQ ID NO: 62          moltype = AA  length = 8
FEATURE                Location/Qualifiers
REGION                 1..8
                       note = Peptide
source                 1..8
                       mol_type = protein
                       organism = synthetic construct
SEQUENCE: 62
SLSCYKVF                                                                   8

SEQ ID NO: 63          moltype = AA  length = 8
FEATURE                Location/Qualifiers
REGION                 1..8
                       note = Peptide
source                 1..8
                       mol_type = protein
                       organism = synthetic construct
SEQUENCE: 63
LSCYKVFH                                                                   8

SEQ ID NO: 64          moltype = AA  length = 8
FEATURE                Location/Qualifiers
REGION                 1..8
                       note = Peptide
source                 1..8
                       mol_type = protein
                       organism = synthetic construct
SEQUENCE: 64
SCYKVFHA                                                                   8

SEQ ID NO: 65          moltype = AA  length = 8
FEATURE                Location/Qualifiers
REGION                 1..8
                       note = Peptide
source                 1..8
                       mol_type = protein
                       organism = synthetic construct
SEQUENCE: 65
CYKVFHAE                                                                   8

SEQ ID NO: 66          moltype = AA  length = 8
FEATURE                Location/Qualifiers
REGION                 1..8
                       note = Peptide
source                 1..8
                       mol_type = protein
                       organism = synthetic construct
SEQUENCE: 66
YKVFHAER                                                                   8

SEQ ID NO: 67          moltype = AA  length = 8
FEATURE                Location/Qualifiers
REGION                 1..8
                       note = Peptide
source                 1..8
                       mol_type = protein
                       organism = synthetic construct
SEQUENCE: 67
KVFHAERI                                                                   8

SEQ ID NO: 68          moltype = AA  length = 8
FEATURE                Location/Qualifiers
REGION                 1..8
                       note = Peptide
source                 1..8
                       mol_type = protein
                       organism = synthetic construct
SEQUENCE: 68
VFHAERIV                                                                   8

SEQ ID NO: 69          moltype = AA  length = 8
FEATURE                Location/Qualifiers
REGION                 1..8
                       note = Peptide
source                 1..8
```

```
                        mol_type = protein
                        organism = synthetic construct
SEQUENCE: 69
FHAERIVR                                                     8

SEQ ID NO: 70           moltype = AA  length = 8
FEATURE                 Location/Qualifiers
REGION                  1..8
                        note = Peptide
source                  1..8
                        mol_type = protein
                        organism = synthetic construct
SEQUENCE: 70
DCAAVKVF                                                     8

SEQ ID NO: 71           moltype = AA  length = 8
FEATURE                 Location/Qualifiers
REGION                  1..8
                        note = Peptide
source                  1..8
                        mol_type = protein
                        organism = synthetic construct
SEQUENCE: 71
AAVKVFHR                                                     8

SEQ ID NO: 72           moltype = AA  length = 8
FEATURE                 Location/Qualifiers
REGION                  1..8
                        note = Peptide
source                  1..8
                        mol_type = protein
                        organism = synthetic construct
SEQUENCE: 72
VKVFHRPW                                                     8

SEQ ID NO: 73           moltype = AA  length = 8
FEATURE                 Location/Qualifiers
REGION                  1..8
                        note = Peptide
source                  1..8
                        mol_type = protein
                        organism = synthetic construct
SEQUENCE: 73
VFHRPWRR                                                     8

SEQ ID NO: 74           moltype = AA  length = 8
FEATURE                 Location/Qualifiers
REGION                  1..8
                        note = Peptide
source                  1..8
                        mol_type = protein
                        organism = synthetic construct
SEQUENCE: 74
HRPWRRGW                                                     8

SEQ ID NO: 75           moltype = AA  length = 8
FEATURE                 Location/Qualifiers
REGION                  1..8
                        note = Peptide
source                  1..8
                        mol_type = protein
                        organism = synthetic construct
SEQUENCE: 75
PWRRGWHF                                                     8

SEQ ID NO: 76           moltype = AA  length = 8
FEATURE                 Location/Qualifiers
REGION                  1..8
                        note = Peptide
source                  1..8
                        mol_type = protein
                        organism = synthetic construct
SEQUENCE: 76
RRGWHFYD                                                     8

SEQ ID NO: 77           moltype = AA  length = 8
FEATURE                 Location/Qualifiers
REGION                  1..8
                        note = Peptide
```

```
source                   1..8
                         mol_type = protein
                         organism = synthetic construct
SEQUENCE: 77
GWHFYDDR                                                                   8

SEQ ID NO: 78            moltype = AA  length = 8
FEATURE                  Location/Qualifiers
REGION                   1..8
                         note = Peptide
source                   1..8
                         mol_type = protein
                         organism = synthetic construct
SEQUENCE: 78
HFYDDREF                                                                   8

SEQ ID NO: 79            moltype = AA  length = 8
FEATURE                  Location/Qualifiers
REGION                   1..8
                         note = Peptide
source                   1..8
                         mol_type = protein
                         organism = synthetic construct
SEQUENCE: 79
YDDREFIY                                                                   8

SEQ ID NO: 80            moltype = AA  length = 8
FEATURE                  Location/Qualifiers
REGION                   1..8
                         note = Peptide
source                   1..8
                         mol_type = protein
                         organism = synthetic construct
SEQUENCE: 80
DREFIYLR                                                                   8

SEQ ID NO: 81            moltype = AA  length = 8
FEATURE                  Location/Qualifiers
REGION                   1..8
                         note = Peptide
source                   1..8
                         mol_type = protein
                         organism = synthetic construct
SEQUENCE: 81
EFIYLRPF                                                                   8

SEQ ID NO: 82            moltype = AA  length = 8
FEATURE                  Location/Qualifiers
REGION                   1..8
                         note = Peptide
source                   1..8
                         mol_type = protein
                         organism = synthetic construct
SEQUENCE: 82
PIDDHFTY                                                                   8

SEQ ID NO: 83            moltype = AA  length = 8
FEATURE                  Location/Qualifiers
REGION                   1..8
                         note = Peptide
source                   1..8
                         mol_type = protein
                         organism = synthetic construct
SEQUENCE: 83
IDDHFTYS                                                                   8

SEQ ID NO: 84            moltype = AA  length = 8
FEATURE                  Location/Qualifiers
REGION                   1..8
                         note = Peptide
source                   1..8
                         mol_type = protein
                         organism = synthetic construct
SEQUENCE: 84
DDHFTYSR                                                                   8

SEQ ID NO: 85            moltype = AA  length = 8
FEATURE                  Location/Qualifiers
REGION                   1..8
```

```
                        note = Peptide
source                  1..8
                        mol_type = protein
                        organism = synthetic construct
SEQUENCE: 85
DHFTYSRY                                                        8

SEQ ID NO: 86           moltype = AA  length = 8
FEATURE                 Location/Qualifiers
REGION                  1..8
                        note = Peptide
source                  1..8
                        mol_type = protein
                        organism = synthetic construct
SEQUENCE: 86
HFTYSRYP                                                        8

SEQ ID NO: 87           moltype = AA  length = 8
FEATURE                 Location/Qualifiers
REGION                  1..8
                        note = Peptide
source                  1..8
                        mol_type = protein
                        organism = synthetic construct
SEQUENCE: 87
FTYSRYPW                                                        8

SEQ ID NO: 88           moltype = AA  length = 8
FEATURE                 Location/Qualifiers
REGION                  1..8
                        note = Peptide
source                  1..8
                        mol_type = protein
                        organism = synthetic construct
SEQUENCE: 88
TYSRYPWH                                                        8

SEQ ID NO: 89           moltype = AA  length = 8
FEATURE                 Location/Qualifiers
REGION                  1..8
                        note = Peptide
source                  1..8
                        mol_type = protein
                        organism = synthetic construct
SEQUENCE: 89
YSRYPWHR                                                        8

SEQ ID NO: 90           moltype = AA  length = 8
FEATURE                 Location/Qualifiers
REGION                  1..8
                        note = Peptide
source                  1..8
                        mol_type = protein
                        organism = synthetic construct
SEQUENCE: 90
SRYPWHRF                                                        8

SEQ ID NO: 91           moltype = AA  length = 8
FEATURE                 Location/Qualifiers
REGION                  1..8
                        note = Peptide
source                  1..8
                        mol_type = protein
                        organism = synthetic construct
SEQUENCE: 91
RYPWHRFP                                                        8

SEQ ID NO: 92           moltype = AA  length = 8
FEATURE                 Location/Qualifiers
REGION                  1..8
                        note = Peptide
source                  1..8
                        mol_type = protein
                        organism = synthetic construct
SEQUENCE: 92
YPWHRFPV                                                        8

SEQ ID NO: 93           moltype = AA  length = 8
FEATURE                 Location/Qualifiers
```

-continued

```
REGION                  1..8
                        note = Peptide
source                  1..8
                        mol_type = protein
                        organism = synthetic construct
SEQUENCE: 93
PWHRFPVT                                                                    8

SEQ ID NO: 94           moltype = AA  length = 8
FEATURE                 Location/Qualifiers
REGION                  1..8
                        note = Peptide
source                  1..8
                        mol_type = protein
                        organism = synthetic construct
SEQUENCE: 94
WHRFPVTF                                                                    8

SEQ ID NO: 95           moltype = AA  length = 8
FEATURE                 Location/Qualifiers
REGION                  1..8
                        note = Peptide
source                  1..8
                        mol_type = protein
                        organism = synthetic construct
SEQUENCE: 95
HRFPVTFG                                                                    8

SEQ ID NO: 96           moltype = AA  length = 8
FEATURE                 Location/Qualifiers
REGION                  1..8
                        note = Peptide
source                  1..8
                        mol_type = protein
                        organism = synthetic construct
SEQUENCE: 96
RELTYSNF                                                                    8

SEQ ID NO: 97           moltype = AA  length = 8
FEATURE                 Location/Qualifiers
REGION                  1..8
                        note = Peptide
source                  1..8
                        mol_type = protein
                        organism = synthetic construct
SEQUENCE: 97
ELTYSNFH                                                                    8

SEQ ID NO: 98           moltype = AA  length = 8
FEATURE                 Location/Qualifiers
REGION                  1..8
                        note = Peptide
source                  1..8
                        mol_type = protein
                        organism = synthetic construct
SEQUENCE: 98
LTYSNFHP                                                                    8

SEQ ID NO: 99           moltype = AA  length = 8
FEATURE                 Location/Qualifiers
REGION                  1..8
                        note = Peptide
source                  1..8
                        mol_type = protein
                        organism = synthetic construct
SEQUENCE: 99
TYSNFHPL                                                                    8

SEQ ID NO: 100          moltype = AA  length = 8
FEATURE                 Location/Qualifiers
REGION                  1..8
                        note = Peptide
source                  1..8
                        mol_type = protein
                        organism = synthetic construct
SEQUENCE: 100
YSNFHPLL                                                                    8

SEQ ID NO: 101          moltype = AA  length = 8
```

-continued

```
FEATURE                 Location/Qualifiers
REGION                  1..8
                        note = Peptide
source                  1..8
                        mol_type = protein
                        organism = synthetic construct
SEQUENCE: 101
SNFHPLLV                                                                  8

SEQ ID NO: 102          moltype = AA  length = 8
FEATURE                 Location/Qualifiers
REGION                  1..8
                        note = Peptide
source                  1..8
                        mol_type = protein
                        organism = synthetic construct
SEQUENCE: 102
NFHPLLVS                                                                  8

SEQ ID NO: 103          moltype = AA  length = 8
FEATURE                 Location/Qualifiers
REGION                  1..8
                        note = Peptide
source                  1..8
                        mol_type = protein
                        organism = synthetic construct
SEQUENCE: 103
FHPLLVSG                                                                  8

SEQ ID NO: 104          moltype = AA  length = 8
FEATURE                 Location/Qualifiers
REGION                  1..8
                        note = Peptide
source                  1..8
                        mol_type = protein
                        organism = synthetic construct
SEQUENCE: 104
HPLLVSGR                                                                  8

SEQ ID NO: 105          moltype = AA  length = 8
FEATURE                 Location/Qualifiers
REGION                  1..8
                        note = Peptide
source                  1..8
                        mol_type = protein
                        organism = synthetic construct
SEQUENCE: 105
PLLVSGRL                                                                  8

SEQ ID NO: 106          moltype = AA  length = 8
FEATURE                 Location/Qualifiers
REGION                  1..8
                        note = Peptide
source                  1..8
                        mol_type = protein
                        organism = synthetic construct
SEQUENCE: 106
LLVSGRLR                                                                  8

SEQ ID NO: 107          moltype = AA  length = 8
FEATURE                 Location/Qualifiers
REGION                  1..8
                        note = Peptide
source                  1..8
                        mol_type = protein
                        organism = synthetic construct
SEQUENCE: 107
LVSGRLRI                                                                  8

SEQ ID NO: 108          moltype = AA  length = 8
FEATURE                 Location/Qualifiers
REGION                  1..8
                        note = Peptide
source                  1..8
                        mol_type = protein
                        organism = synthetic construct
SEQUENCE: 108
VSGRLRIP                                                                  8
```

-continued

```
SEQ ID NO: 109          moltype = AA  length = 8
FEATURE                 Location/Qualifiers
REGION                  1..8
                        note = Peptide
source                  1..8
                        mol_type = protein
                        organism = synthetic construct
SEQUENCE: 109
FTSCSERH                                                              8

SEQ ID NO: 110          moltype = AA  length = 8
FEATURE                 Location/Qualifiers
REGION                  1..8
                        note = Peptide
source                  1..8
                        mol_type = protein
                        organism = synthetic construct
SEQUENCE: 110
TSCSERHF                                                              8

SEQ ID NO: 111          moltype = AA  length = 8
FEATURE                 Location/Qualifiers
REGION                  1..8
                        note = Peptide
source                  1..8
                        mol_type = protein
                        organism = synthetic construct
SEQUENCE: 111
SCSERHFV                                                              8

SEQ ID NO: 112          moltype = AA  length = 8
FEATURE                 Location/Qualifiers
REGION                  1..8
                        note = Peptide
source                  1..8
                        mol_type = protein
                        organism = synthetic construct
SEQUENCE: 112
CSERHFVS                                                              8

SEQ ID NO: 113          moltype = AA  length = 8
FEATURE                 Location/Qualifiers
REGION                  1..8
                        note = Peptide
source                  1..8
                        mol_type = protein
                        organism = synthetic construct
SEQUENCE: 113
SERHFVSL                                                              8

SEQ ID NO: 114          moltype = AA  length = 8
FEATURE                 Location/Qualifiers
REGION                  1..8
                        note = Peptide
source                  1..8
                        mol_type = protein
                        organism = synthetic construct
SEQUENCE: 114
ERHFVSLC                                                              8

SEQ ID NO: 115          moltype = AA  length = 8
FEATURE                 Location/Qualifiers
REGION                  1..8
                        note = Peptide
source                  1..8
                        mol_type = protein
                        organism = synthetic construct
SEQUENCE: 115
RHFVSLCQ                                                              8

SEQ ID NO: 116          moltype = AA  length = 8
FEATURE                 Location/Qualifiers
REGION                  1..8
                        note = Peptide
source                  1..8
                        mol_type = protein
                        organism = synthetic construct
SEQUENCE: 116
HFVSLCQK                                                              8
```

```
SEQ ID NO: 117          moltype = AA  length = 8
FEATURE                 Location/Qualifiers
REGION                  1..8
                        note = Peptide
source                  1..8
                        mol_type = protein
                        organism = synthetic construct
SEQUENCE: 117
FVSLCQKY                                                            8

SEQ ID NO: 118          moltype = AA  length = 8
FEATURE                 Location/Qualifiers
REGION                  1..8
                        note = Peptide
source                  1..8
                        mol_type = protein
                        organism = synthetic construct
SEQUENCE: 118
VSLCQKYS                                                            8

SEQ ID NO: 119          moltype = AA  length = 8
FEATURE                 Location/Qualifiers
REGION                  1..8
                        note = Peptide
source                  1..8
                        mol_type = protein
                        organism = synthetic construct
SEQUENCE: 119
SLCQKYSE                                                            8

SEQ ID NO: 120          moltype = AA  length = 8
FEATURE                 Location/Qualifiers
REGION                  1..8
                        note = Peptide
source                  1..8
                        mol_type = protein
                        organism = synthetic construct
SEQUENCE: 120
LCQKYSEV                                                            8

SEQ ID NO: 121          moltype = AA  length = 8
FEATURE                 Location/Qualifiers
REGION                  1..8
                        note = Peptide
source                  1..8
                        mol_type = protein
                        organism = synthetic construct
SEQUENCE: 121
CQKYSEVK                                                            8

SEQ ID NO: 122          moltype = AA  length = 8
FEATURE                 Location/Qualifiers
REGION                  1..8
                        note = Peptide
source                  1..8
                        mol_type = protein
                        organism = synthetic construct
SEQUENCE: 122
QKYSEVKS                                                            8

SEQ ID NO: 123          moltype = AA  length = 8
FEATURE                 Location/Qualifiers
REGION                  1..8
                        note = Peptide
source                  1..8
                        mol_type = protein
                        organism = synthetic construct
SEQUENCE: 123
TVKYLNNL                                                            8

SEQ ID NO: 124          moltype = AA  length = 8
FEATURE                 Location/Qualifiers
REGION                  1..8
                        note = Peptide
source                  1..8
                        mol_type = protein
                        organism = synthetic construct
SEQUENCE: 124
```

-continued

```
VKYLNNLY                                                        8

SEQ ID NO: 125          moltype = AA  length = 8
FEATURE                 Location/Qualifiers
REGION                  1..8
                        note = Peptide
source                  1..8
                        mol_type = protein
                        organism = synthetic construct
SEQUENCE: 125
KYLNNLYK                                                        8

SEQ ID NO: 126          moltype = AA  length = 8
FEATURE                 Location/Qualifiers
REGION                  1..8
                        note = Peptide
source                  1..8
                        mol_type = protein
                        organism = synthetic construct
SEQUENCE: 126
YLNNLYKI                                                        8

SEQ ID NO: 127          moltype = AA  length = 8
FEATURE                 Location/Qualifiers
REGION                  1..8
                        note = Peptide
source                  1..8
                        mol_type = protein
                        organism = synthetic construct
SEQUENCE: 127
LNNLYKII                                                        8

SEQ ID NO: 128          moltype = AA  length = 8
FEATURE                 Location/Qualifiers
REGION                  1..8
                        note = Peptide
source                  1..8
                        mol_type = protein
                        organism = synthetic construct
SEQUENCE: 128
NNLYKIIP                                                        8

SEQ ID NO: 129          moltype = AA  length = 8
FEATURE                 Location/Qualifiers
REGION                  1..8
                        note = Peptide
source                  1..8
                        mol_type = protein
                        organism = synthetic construct
SEQUENCE: 129
NLYKIIPK                                                        8

SEQ ID NO: 130          moltype = AA  length = 8
FEATURE                 Location/Qualifiers
REGION                  1..8
                        note = Peptide
source                  1..8
                        mol_type = protein
                        organism = synthetic construct
SEQUENCE: 130
LYKIIPKT                                                        8

SEQ ID NO: 131          moltype = AA  length = 8
FEATURE                 Location/Qualifiers
REGION                  1..8
                        note = Peptide
source                  1..8
                        mol_type = protein
                        organism = synthetic construct
SEQUENCE: 131
YKIIPKTL                                                        8

SEQ ID NO: 132          moltype = AA  length = 8
FEATURE                 Location/Qualifiers
REGION                  1..8
                        note = Peptide
source                  1..8
                        mol_type = protein
                        organism = synthetic construct
```

```
SEQUENCE: 132
KIIPKTLT                                                                   8

SEQ ID NO: 133          moltype = AA  length = 8
FEATURE                 Location/Qualifiers
REGION                  1..8
                        note = Peptide
source                  1..8
                        mol_type = protein
                        organism = synthetic construct
SEQUENCE: 133
IIPKTLTW                                                                   8

SEQ ID NO: 134          moltype = AA  length = 8
FEATURE                 Location/Qualifiers
REGION                  1..8
                        note = Peptide
source                  1..8
                        mol_type = protein
                        organism = synthetic construct
SEQUENCE: 134
IPKTLTWH                                                                   8

SEQ ID NO: 135          moltype = AA  length = 8
FEATURE                 Location/Qualifiers
REGION                  1..8
                        note = Peptide
source                  1..8
                        mol_type = protein
                        organism = synthetic construct
SEQUENCE: 135
PKTLTWHS                                                                   8

SEQ ID NO: 136          moltype = AA  length = 8
FEATURE                 Location/Qualifiers
REGION                  1..8
                        note = Peptide
source                  1..8
                        mol_type = protein
                        organism = synthetic construct
SEQUENCE: 136
KTLTWHSA                                                                   8

SEQ ID NO: 137          moltype = AA  length = 8
FEATURE                 Location/Qualifiers
REGION                  1..8
                        note = Peptide
source                  1..8
                        mol_type = protein
                        organism = synthetic construct
SEQUENCE: 137
TLTWHSAK                                                                   8

SEQ ID NO: 138          moltype = AA  length = 8
FEATURE                 Location/Qualifiers
REGION                  1..8
                        note = Peptide
source                  1..8
                        mol_type = protein
                        organism = synthetic construct
SEQUENCE: 138
EAVYFHQH                                                                   8

SEQ ID NO: 139          moltype = AA  length = 8
FEATURE                 Location/Qualifiers
REGION                  1..8
                        note = Peptide
source                  1..8
                        mol_type = protein
                        organism = synthetic construct
SEQUENCE: 139
AVYFHQHS                                                                   8

SEQ ID NO: 140          moltype = AA  length = 8
FEATURE                 Location/Qualifiers
REGION                  1..8
                        note = Peptide
source                  1..8
                        mol_type = protein
```

```
                        organism = synthetic construct
SEQUENCE: 140
VYFHQHSI                                                                    8

SEQ ID NO: 141          moltype = AA  length = 8
FEATURE                 Location/Qualifiers
REGION                  1..8
                        note = Peptide
source                  1..8
                        mol_type = protein
                        organism = synthetic construct
SEQUENCE: 141
YFHQHSIL                                                                    8

SEQ ID NO: 142          moltype = AA  length = 8
FEATURE                 Location/Qualifiers
REGION                  1..8
                        note = Peptide
source                  1..8
                        mol_type = protein
                        organism = synthetic construct
SEQUENCE: 142
FHQHSILA                                                                    8

SEQ ID NO: 143          moltype = AA  length = 8
FEATURE                 Location/Qualifiers
REGION                  1..8
                        note = Peptide
source                  1..8
                        mol_type = protein
                        organism = synthetic construct
SEQUENCE: 143
KKLSRLTY                                                                    8

SEQ ID NO: 144          moltype = AA  length = 8
FEATURE                 Location/Qualifiers
REGION                  1..8
                        note = Peptide
source                  1..8
                        mol_type = protein
                        organism = synthetic construct
SEQUENCE: 144
KLSRLTYS                                                                    8

SEQ ID NO: 145          moltype = AA  length = 8
FEATURE                 Location/Qualifiers
REGION                  1..8
                        note = Peptide
source                  1..8
                        mol_type = protein
                        organism = synthetic construct
SEQUENCE: 145
LSRLTYSS                                                                    8

SEQ ID NO: 146          moltype = AA  length = 8
FEATURE                 Location/Qualifiers
REGION                  1..8
                        note = Peptide
source                  1..8
                        mol_type = protein
                        organism = synthetic construct
SEQUENCE: 146
SRLTYSSR                                                                    8

SEQ ID NO: 147          moltype = AA  length = 8
FEATURE                 Location/Qualifiers
REGION                  1..8
                        note = Peptide
source                  1..8
                        mol_type = protein
                        organism = synthetic construct
SEQUENCE: 147
RLTYSSRC                                                                    8

SEQ ID NO: 148          moltype = AA  length = 8
FEATURE                 Location/Qualifiers
REGION                  1..8
                        note = Peptide
source                  1..8
```

-continued

```
                        mol_type = protein
                        organism = synthetic construct
SEQUENCE: 148
NGSRWIQY                                                                     8

SEQ ID NO: 149          moltype = AA  length = 8
FEATURE                 Location/Qualifiers
REGION                  1..8
                        note = Peptide
source                  1..8
                        mol_type = protein
                        organism = synthetic construct
SEQUENCE: 149
GSRWIQYK                                                                     8

SEQ ID NO: 150          moltype = AA  length = 8
FEATURE                 Location/Qualifiers
REGION                  1..8
                        note = Peptide
source                  1..8
                        mol_type = protein
                        organism = synthetic construct
SEQUENCE: 150
SRWIQYKG                                                                     8

SEQ ID NO: 151          moltype = AA  length = 8
FEATURE                 Location/Qualifiers
REGION                  1..8
                        note = Peptide
source                  1..8
                        mol_type = protein
                        organism = synthetic construct
SEQUENCE: 151
RWIQYKGH                                                                     8

SEQ ID NO: 152          moltype = AA  length = 8
FEATURE                 Location/Qualifiers
REGION                  1..8
                        note = Peptide
source                  1..8
                        mol_type = protein
                        organism = synthetic construct
SEQUENCE: 152
WIQYKGHC                                                                     8

SEQ ID NO: 153          moltype = AA  length = 8
FEATURE                 Location/Qualifiers
REGION                  1..8
                        note = Peptide
source                  1..8
                        mol_type = protein
                        organism = synthetic construct
SEQUENCE: 153
IQYKGHCY                                                                     8

SEQ ID NO: 154          moltype = AA  length = 8
FEATURE                 Location/Qualifiers
REGION                  1..8
                        note = Peptide
source                  1..8
                        mol_type = protein
                        organism = synthetic construct
SEQUENCE: 154
QYKGHCYK                                                                     8

SEQ ID NO: 155          moltype = AA  length = 8
FEATURE                 Location/Qualifiers
REGION                  1..8
                        note = Peptide
source                  1..8
                        mol_type = protein
                        organism = synthetic construct
SEQUENCE: 155
YKGHCYKS                                                                     8

SEQ ID NO: 156          moltype = AA  length = 8
FEATURE                 Location/Qualifiers
REGION                  1..8
                        note = Peptide
```

```
source                 1..8
                       mol_type = protein
                       organism = synthetic construct
SEQUENCE: 156
KGHCYKSD                                                                  8

SEQ ID NO: 157         moltype = AA  length = 8
FEATURE                Location/Qualifiers
REGION                 1..8
                       note = Peptide
source                 1..8
                       mol_type = protein
                       organism = synthetic construct
SEQUENCE: 157
GHCYKSDQ                                                                  8

SEQ ID NO: 158         moltype = AA  length = 8
FEATURE                Location/Qualifiers
REGION                 1..8
                       note = Peptide
source                 1..8
                       mol_type = protein
                       organism = synthetic construct
SEQUENCE: 158
HCYKSDQA                                                                  8

SEQ ID NO: 159         moltype = AA  length = 8
FEATURE                Location/Qualifiers
REGION                 1..8
                       note = Peptide
source                 1..8
                       mol_type = protein
                       organism = synthetic construct
SEQUENCE: 159
CYKSDQAL                                                                  8

SEQ ID NO: 160         moltype = AA  length = 8
FEATURE                Location/Qualifiers
REGION                 1..8
                       note = Peptide
source                 1..8
                       mol_type = protein
                       organism = synthetic construct
SEQUENCE: 160
YKSDQALH                                                                  8

SEQ ID NO: 161         moltype = AA  length = 8
FEATURE                Location/Qualifiers
REGION                 1..8
                       note = Peptide
source                 1..8
                       mol_type = protein
                       organism = synthetic construct
SEQUENCE: 161
KSDQALHS                                                                  8

SEQ ID NO: 162         moltype = AA  length = 8
FEATURE                Location/Qualifiers
REGION                 1..8
                       note = Peptide
source                 1..8
                       mol_type = protein
                       organism = synthetic construct
SEQUENCE: 162
SDQALHSF                                                                  8

SEQ ID NO: 163         moltype = AA  length = 8
FEATURE                Location/Qualifiers
REGION                 1..8
                       note = Peptide
source                 1..8
                       mol_type = protein
                       organism = synthetic construct
SEQUENCE: 163
DQALHSFS                                                                  8

SEQ ID NO: 164         moltype = AA  length = 1722
FEATURE                Location/Qualifiers
source                 1..1722
```

```
                         mol_type = protein
                         organism = Homo sapiens
SEQUENCE: 164
MRTGWATPRR PAGLLMLLFW FFDLAEPSGR AANDPFTIVH GNTGKCIKPV YGWIVADDCD  60
ETEDKLWKWV SQHRLFHLHS QKCLGLDITK SVNELRMFSC DSSAMLWWKC EHHSLYGAAR  120
YRLALKDGHG TAISNASDVW KKGGSEESLC DQPYHEIYTR DGNSYGRPCE FPFLIDGTWH  180
HDCILDEDHS GPWCATTLNY EYDRKWGICL KPENGCEDNW EKNEQFGSCY QFNTQTALSW  240
KEAYVSCQNQ GADLLSINSA AELTYLKEKE GIAKIFWIGL NQLYSARGWE WSDHKPLNFL  300
NWDPDRPSAP TIGGSSCARM DAESGLWQSF SCEAQLPYVC RKPLNNTVEL TDVWTYSDTR  360
CDAGWLPNNG FCYLLVNESN SWDKAHAKCK AFSSDLISIH SLADVEVVVT KLHNEDIKEE  420
VWIGLKNINI PTLFQWSDGT EVTLTYWDEN EPNVPYNKTP NCVSYLGELG QWKVQSCEEK  480
LKYVCKRKGE KLNDASSDKM CPPDEGWKRH GETCYKIYED EVPFGTNCNL TITSRFEQEY  540
LNDLMKKYDK SLRKYFWTGL RDVDSCGEYN WATVGGRRRA VTFSNWNFLE PASPGGCVAM  600
STGKSVGKWE VKDCRSFKAL SICKKMSGPL GPEEASPKPD DPCPEGWQSF PASLSCYKVF  660
HAERIVRKRN WEEAERFCQA LGAHLSSFSH VDEIKEFLHF LTDQFSGQHW LWIGLNKRSP  720
DLQGSWQWSD RTPVSTIIMP NEFQQDYDIR DCAAVKVFHR PWRRGWHFYD DREFIYLRPF  780
ACDTKLEWVC QIPKGRTPKT PDWYNPDRAG IHGPPLIIEG SEYWFVADLH LNYEEAVLYC  840
ASNHSFLATI TSFVGLKAIK NKIANISGDG QKWWIRISEW PIDDHFTYSR YPWHRFPVTF  900
GEECLYMSAK TWLIDLGKPT DCSTKLPFIC EKYNVSSLEK YSPDSAAKVQ CSEQWIPFQN  960
KCFLKIKPVS LTFSQASDTC HSYGGTLPSV LSQIEQDFIT SLLPDMEATL WIGLRWTAYE  1020
KINKWTDNRE LTYSNFHPLL VSGRLRIPEN FFEEESRYHC ALILNLQKSP FTGTWNFTSC  1080
SERHFVSLCQ KYSEVKSRQT LQNASETVKY LNNLYKIIPK TLTWHSAKRE CLKSNMQLVS  1140
ITDPYQQAFL SVQALLHNSS LWIGLFSQDD ELNFGWSDGK RLHFSRWAET NGQLEDCVVL  1200
DTDGFWKTVD CNDNQPGAIC YYSGNETEKE VKPVDSVKCP SPVLNTPWIP FQNCCYNFII  1260
TKNRHMATTQ DEVHTKCQKL NPKSHILSIR DEKENNFVLE QLLYFNYMAS WVMLGITYRN  1320
KSLMWFDKTP LSYTHWRAGR PTIKNEKFLA GLSTDGFWDI QTFKVIEEAV YFHQHSILAC  1380
KIEMVDYKEE YNTTLPQFMP YEDGIYSVIQ KKVTWYEALN MCSQSGGHLA SVHNQNGQLF  1440
LEDIVKRDGF PLWVGLSSHD GSESSFEWSD GSTFDYIPWK GQTSPGNCVL LDPKGTWKHE  1500
KCNSVKDGAI CYKPTKSKKL SRLTYSSRCP AAKENGSRWI QYKGHCYKSD QALHSFSEAK  1560
KLCSKHDHSA TIVSIKDEDE NKFVSRLMRE NNNITMRVWL GLSQHSVDQS WSWLDGSEVT  1620
FVKWENKSKS GVGRCSMLIA SNETWKKVEC EHGFGRVVCK VPLGPDYTAI AIIVATLSIL  1680
VLMGGLIWFL FQRHRLHLAG FSSVRYAQGV NEDEIMLPSF HD                    1722

SEQ ID NO: 165         moltype = AA  length = 23
FEATURE                Location/Qualifiers
REGION                 1..23
                       note = Peptide
source                 1..23
                       mol_type = protein
                       organism = synthetic construct
SEQUENCE: 165
CIKPVYGWIV ADDCDETEDK LWK                                         23

SEQ ID NO: 166         moltype = AA  length = 11
FEATURE                Location/Qualifiers
REGION                 1..11
                       note = Peptide
source                 1..11
                       mol_type = protein
                       organism = synthetic construct
SEQUENCE: 166
CEHHSLYGAA R                                                      11

SEQ ID NO: 167         moltype = AA  length = 34
FEATURE                Location/Qualifiers
REGION                 1..34
                       note = Peptide
source                 1..34
                       mol_type = protein
                       organism = synthetic construct
SEQUENCE: 167
DGHGTAISNA SDVWKKGGSE ESLCDQPYHE IYTR                             34

SEQ ID NO: 168         moltype = AA  length = 19
FEATURE                Location/Qualifiers
REGION                 1..19
                       note = Peptide
source                 1..19
                       mol_type = protein
                       organism = synthetic construct
SEQUENCE: 168
KGGSEESLCD QPYHEIYTR                                              19

SEQ ID NO: 169         moltype = AA  length = 18
FEATURE                Location/Qualifiers
REGION                 1..18
                       note = Peptide
source                 1..18
                       mol_type = protein
```

```
                       organism = synthetic construct
SEQUENCE: 169
GGSEESLCDQ PYHEIYTR                                                          18

SEQ ID NO: 170         moltype = AA  length = 15
FEATURE                Location/Qualifiers
REGION                 1..15
                       note = Peptide
source                 1..15
                       mol_type = protein
                       organism = synthetic construct
SEQUENCE: 170
DGHGTAISNA SDVWK                                                             15

SEQ ID NO: 171         moltype = AA  length = 17
FEATURE                Location/Qualifiers
REGION                 1..17
                       note = Peptide
source                 1..17
                       mol_type = protein
                       organism = synthetic construct
SEQUENCE: 171
WGICLKPENG CEDNWEK                                                           17

SEQ ID NO: 172         moltype = AA  length = 13
FEATURE                Location/Qualifiers
REGION                 1..13
                       note = Peptide
source                 1..13
                       mol_type = protein
                       organism = synthetic construct
SEQUENCE: 172
IFWIGLNQLY SAR                                                               13

SEQ ID NO: 173         moltype = AA  length = 15
FEATURE                Location/Qualifiers
REGION                 1..15
                       note = Peptide
source                 1..15
                       mol_type = protein
                       organism = synthetic construct
SEQUENCE: 173
LHNEDIKEEV WIGLK                                                             15

SEQ ID NO: 174         moltype = AA  length = 15
FEATURE                Location/Qualifiers
REGION                 1..15
                       note = Peptide
source                 1..15
                       mol_type = protein
                       organism = synthetic construct
SEQUENCE: 174
TPNCVSYLGE LGQWK                                                             15

SEQ ID NO: 175         moltype = AA  length = 23
FEATURE                Location/Qualifiers
REGION                 1..23
                       note = Peptide
source                 1..23
                       mol_type = protein
                       organism = synthetic construct
SEQUENCE: 175
YFWTGLRDVD SCGEYNWATV GGR                                                    23

SEQ ID NO: 176         moltype = AA  length = 11
FEATURE                Location/Qualifiers
REGION                 1..11
                       note = Peptide
source                 1..11
                       mol_type = protein
                       organism = synthetic construct
SEQUENCE: 176
SVGKWEVKDC R                                                                 11

SEQ ID NO: 177         moltype = AA  length = 10
FEATURE                Location/Qualifiers
REGION                 1..10
                       note = Peptide
source                 1..10
```

```
                        mol_type = protein
                        organism = synthetic construct
SEQUENCE: 177
WEVKDCRSFK                                                         10

SEQ ID NO: 178          moltype = AA  length = 7
FEATURE                 Location/Qualifiers
REGION                  1..7
                        note = Peptide
source                  1..7
                        mol_type = protein
                        organism = synthetic construct
SEQUENCE: 178
ALSICKK                                                            7

SEQ ID NO: 179          moltype = AA  length = 12
FEATURE                 Location/Qualifiers
REGION                  1..12
                        note = Peptide
source                  1..12
                        mol_type = protein
                        organism = synthetic construct
SEQUENCE: 179
PASLSCYKVF HA                                                      12

SEQ ID NO: 180          moltype = AA  length = 8
FEATURE                 Location/Qualifiers
REGION                  1..8
                        note = Peptide
source                  1..8
                        mol_type = protein
                        organism = synthetic construct
SEQUENCE: 180
RNWEEAER                                                           8

SEQ ID NO: 181          moltype = AA  length = 33
FEATURE                 Location/Qualifiers
REGION                  1..33
                        note = Peptide
source                  1..33
                        mol_type = protein
                        organism = synthetic construct
SEQUENCE: 181
RSPDLQGSWQ WSDRTPVSTI IMPNEFQQDY DIR                               33

SEQ ID NO: 182          moltype = AA  length = 19
FEATURE                 Location/Qualifiers
REGION                  1..19
                        note = Peptide
source                  1..19
                        mol_type = protein
                        organism = synthetic construct
SEQUENCE: 182
TPVSTIIMPN EFQQDYDIR                                               19

SEQ ID NO: 183          moltype = AA  length = 20
FEATURE                 Location/Qualifiers
REGION                  1..20
                        note = Peptide
source                  1..20
                        mol_type = protein
                        organism = synthetic construct
SEQUENCE: 183
PWRRGWHFYD DREFIYLRPF                                              20

SEQ ID NO: 184          moltype = AA  length = 8
FEATURE                 Location/Qualifiers
REGION                  1..8
                        note = Peptide
source                  1..8
                        mol_type = protein
                        organism = synthetic construct
SEQUENCE: 184
GWHFYDDR                                                           8

SEQ ID NO: 185          moltype = AA  length = 14
FEATURE                 Location/Qualifiers
REGION                  1..14
                        note = Peptide
```

-continued

```
source                 1..14
                       mol_type = protein
                       organism = synthetic construct
SEQUENCE: 185
ISEWPIDDHF TYSR                                                14

SEQ ID NO: 186         moltype = AA  length = 19
FEATURE                Location/Qualifiers
REGION                 1..19
                       note = Peptide
source                 1..19
                       mol_type = protein
                       organism = synthetic construct
SEQUENCE: 186
DDHFTYSRYP WHRFPVTFG                                           19

SEQ ID NO: 187         moltype = AA  length = 30
FEATURE                Location/Qualifiers
REGION                 1..30
                       note = Peptide
source                 1..30
                       mol_type = protein
                       organism = synthetic construct
SEQUENCE: 187
FPVTFGEECL YMSAKTWLID LGKPTDCSTK                               30

SEQ ID NO: 188         moltype = AA  length = 15
FEATURE                Location/Qualifiers
REGION                 1..15
                       note = Peptide
source                 1..15
                       mol_type = protein
                       organism = synthetic construct
SEQUENCE: 188
TWLIDLGKPT DCSTK                                               15

SEQ ID NO: 189         moltype = AA  length = 8
FEATURE                Location/Qualifiers
REGION                 1..8
                       note = Peptide
source                 1..8
                       mol_type = protein
                       organism = synthetic construct
SEQUENCE: 189
YNVSSLEK                                                       8

SEQ ID NO: 190         moltype = AA  length = 12
FEATURE                Location/Qualifiers
REGION                 1..12
                       note = Peptide
source                 1..12
                       mol_type = protein
                       organism = synthetic construct
SEQUENCE: 190
VQCSEQWIPF QN                                                  12

SEQ ID NO: 191         moltype = AA  length = 12
FEATURE                Location/Qualifiers
REGION                 1..12
                       note = Peptide
source                 1..12
                       mol_type = protein
                       organism = synthetic construct
SEQUENCE: 191
RELTYSNFHP LL                                                  12

SEQ ID NO: 192         moltype = AA  length = 39
FEATURE                Location/Qualifiers
REGION                 1..39
                       note = Peptide
source                 1..39
                       mol_type = protein
                       organism = synthetic construct
SEQUENCE: 192
ELTYSNFHPL LVSGRLRIPE NFFEEESRYH CALILNLQK                     39

SEQ ID NO: 193         moltype = AA  length = 11
FEATURE                Location/Qualifiers
REGION                 1..11
```

```
                          note = Peptide
source                    1..11
                          mol_type = protein
                          organism = synthetic construct
SEQUENCE: 193
YHCALILNLQ K                                                         11

SEQ ID NO: 194            moltype = AA  length = 17
FEATURE                   Location/Qualifiers
REGION                    1..17
                          note = Peptide
source                    1..17
                          mol_type = protein
                          organism = synthetic construct
SEQUENCE: 194
FTSCSERHFV SLCQKYS                                                   17

SEQ ID NO: 195            moltype = AA  length = 8
FEATURE                   Location/Qualifiers
REGION                    1..8
                          note = Peptide
source                    1..8
                          mol_type = protein
                          organism = synthetic construct
SEQUENCE: 195
HFVSLCQK                                                             8

SEQ ID NO: 196            moltype = AA  length = 11
FEATURE                   Location/Qualifiers
REGION                    1..11
                          note = Peptide
source                    1..11
                          mol_type = protein
                          organism = synthetic construct
SEQUENCE: 196
QTLQNASETV K                                                         11

SEQ ID NO: 197            moltype = AA  length = 12
FEATURE                   Location/Qualifiers
REGION                    1..12
                          note = Peptide
source                    1..12
                          mol_type = protein
                          organism = synthetic construct
SEQUENCE: 197
TVKYLNNLYK II                                                        12

SEQ ID NO: 198            moltype = AA  length = 8
FEATURE                   Location/Qualifiers
REGION                    1..8
                          note = Peptide
source                    1..8
                          mol_type = protein
                          organism = synthetic construct
SEQUENCE: 198
TLTWHSAK                                                             8

SEQ ID NO: 199            moltype = AA  length = 14
FEATURE                   Location/Qualifiers
REGION                    1..14
                          note = Peptide
source                    1..14
                          mol_type = protein
                          organism = synthetic construct
SEQUENCE: 199
NRHMATTQDE VHTK                                                      14

SEQ ID NO: 200            moltype = AA  length = 7
FEATURE                   Location/Qualifiers
REGION                    1..7
                          note = Peptide
source                    1..7
                          mol_type = protein
                          organism = synthetic construct
SEQUENCE: 200
SHILSIR                                                              7

SEQ ID NO: 201            moltype = AA  length = 16
FEATURE                   Location/Qualifiers
```

-continued

```
REGION              1..16
                    note = Peptide
source              1..16
                    mol_type = protein
                    organism = synthetic construct
SEQUENCE: 201
SLMWFDKTPL SYTHWR                                              16

SEQ ID NO: 202      moltype = AA  length = 7
FEATURE             Location/Qualifiers
REGION              1..7
                    note = Peptide
source              1..7
                    mol_type = protein
                    organism = synthetic construct
SEQUENCE: 202
SLMWFDK                                                        7

SEQ ID NO: 203      moltype = AA  length = 11
FEATURE             Location/Qualifiers
REGION              1..11
                    note = Peptide
source              1..11
                    mol_type = protein
                    organism = synthetic construct
SEQUENCE: 203
EAVYFHQHSI L                                                   11

SEQ ID NO: 204      moltype = AA  length = 10
FEATURE             Location/Qualifiers
REGION              1..10
                    note = Peptide
source              1..10
                    mol_type = protein
                    organism = synthetic construct
SEQUENCE: 204
KKLSRLTYSS                                                     10

SEQ ID NO: 205      moltype = AA  length = 20
FEATURE             Location/Qualifiers
REGION              1..20
                    note = Peptide
source              1..20
                    mol_type = protein
                    organism = synthetic construct
SEQUENCE: 205
NGSRWIQYKG HCYKSDQALH                                          20

SEQ ID NO: 206      moltype = AA  length = 21
FEATURE             Location/Qualifiers
REGION              1..21
                    note = Peptide
source              1..21
                    mol_type = protein
                    organism = synthetic construct
SEQUENCE: 206
HDHSATIVSI KDEDENKFVS R                                        21

SEQ ID NO: 207      moltype = AA  length = 9
FEATURE             Location/Qualifiers
REGION              1..9
                    note = Peptide
source              1..9
                    mol_type = protein
                    organism = synthetic construct
SEQUENCE: 207
VECEHGFGR                                                      9

SEQ ID NO: 208      moltype = AA  length = 15
FEATURE             Location/Qualifiers
source              1..15
                    mol_type = protein
                    organism = synthetic construct
SEQUENCE: 208
GGGGSGGGGS GGGGS                                               15
```